US008623645B2

(12) United States Patent
D'Amour et al.

(10) Patent No.: US 8,623,645 B2
(45) Date of Patent: *Jan. 7, 2014

(54) DEFINITIVE ENDODERM

(75) Inventors: Kevin Allen D'Amour, San Diego, CA (US); Alan D. Agulnick, San Diego, CA (US); Emmanuel E. Baetge, Encinitas, CA (US)

(73) Assignee: Viacyte, Inc., San Diego, CA (US)

( * ) Notice: Subject to any disclaimer, the term of this patent is extended or adjusted under 35 U.S.C. 154(b) by 580 days.

This patent is subject to a terminal disclaimer.

(21) Appl. No.: 12/414,482

(22) Filed: Mar. 30, 2009

(65) Prior Publication Data

US 2009/0253202 A1 Oct. 8, 2009

Related U.S. Application Data

(63) Continuation of application No. 11/021,618, filed on Dec. 23, 2004, now Pat. No. 7,510,876.

(60) Provisional application No. 60/587,942, filed on Jul. 14, 2004, provisional application No. 60/586,566, filed on Jul. 9, 2004, provisional application No. 60/532,004, filed on Dec. 23, 2003.

(51) Int. Cl.
*C12N 5/02* (2006.01)
*C12N 5/071* (2010.01)

(52) U.S. Cl.
USPC .......................................... 435/366; 435/325

(58) Field of Classification Search
USPC .................................. 435/325, 366
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,816,567 A | 3/1989 | Cabilly et al. | |
| 5,453,357 A | 9/1995 | Hogan | |
| 5,670,372 A | 9/1997 | Hogan | |
| 5,690,926 A | 11/1997 | Hogan | |
| 5,817,637 A | 10/1998 | Weiner et al. | |
| 5,830,876 A | 11/1998 | Weiner et al. | |
| 5,843,780 A | 12/1998 | Thomson | |
| 5,866,366 A | 2/1999 | Kallender | |
| 5,869,620 A | 2/1999 | Whitlow et al. | |
| 6,015,671 A | 1/2000 | Field | |
| 6,090,592 A | 7/2000 | Adams et al. | |
| 6,090,622 A | 7/2000 | Gearhart et al. | |
| 6,117,635 A | 9/2000 | Nazarenko et al. | |
| 6,117,986 A | 9/2000 | Nardone et al. | |
| 6,165,993 A | 12/2000 | Herrmann et al. | |
| 6,200,806 B1 | 3/2001 | Thomson | |
| 6,251,671 B1 | 6/2001 | Hogan et al. | |
| 6,261,281 B1 | 7/2001 | Mathiesen et al. | |
| 6,458,589 B1 | 10/2002 | Rambhatla et al. | |
| 6,506,574 B1 | 1/2003 | Rambhatla et al. | |
| 6,872,389 B1 | 3/2005 | Faris | |
| 6,921,811 B2 | 7/2005 | Zamora et al. | |
| 7,033,831 B2 | 4/2006 | Fisk et al. | |
| 7,153,684 B1 | 12/2006 | Hogan | |
| 7,256,042 B2 | 8/2007 | Rambhatla et al. | |
| 7,326,572 B2 | 2/2008 | Fisk et al. | |
| 7,510,876 B2 | 3/2009 | D'Amour et al. | |
| 7,534,608 B2 | 5/2009 | Martinson et al. | |
| 7,541,185 B2 | 6/2009 | D'Amour et al. | |
| 2002/0072117 A1 | 6/2002 | Xu et al. | |
| 2002/0090723 A1 | 7/2002 | Carpenter et al. | |
| 2003/0138948 A1 | 7/2003 | Fisk et al. | |
| 2003/0138949 A1 | 7/2003 | Bhushan et al. | |
| 2003/0175956 A1 | 9/2003 | Bodnar et al. | |
| 2003/0190748 A1 | 10/2003 | Thomson | |
| 2003/0224411 A1 | 12/2003 | Stanton et al. | |
| 2004/0127406 A1 | 7/2004 | Presnell et al. | |
| 2004/0229350 A1 | 11/2004 | Strelchenko et al. | |
| 2005/0079159 A1 | 4/2005 | Shastri et al. | |
| 2005/0158853 A1 | 7/2005 | D'Amour et al. | |
| 2006/0003446 A1 | 1/2006 | Keller et al. | |
| 2006/0019387 A1 | 1/2006 | Faris | |
| 2006/0040385 A1 | 2/2006 | Itskovitz-Eldor et al. | |
| 2006/0040387 A1 | 2/2006 | Fisk et al. | |
| 2006/0128017 A1 | 6/2006 | Geffard et al. | |
| 2006/0148081 A1 | 7/2006 | Kelly et al. | |
| 2006/0276420 A1 | 12/2006 | Keller et al. | |
| 2007/0154984 A1 | 7/2007 | D'Amour et al. | |
| 2007/0281355 A1 | 12/2007 | Dalton et al. | |
| 2009/0253202 A1 | 10/2009 | D'Amour et al. | |

FOREIGN PATENT DOCUMENTS

| | | |
|---|---|---|
| EP | 0 543 942 | 6/1993 |
| EP | 1298201 A | 4/2003 |
| EP | 1 627 912 | 2/2006 |
| JP | 2007/516728 A | 6/2008 |

(Continued)

OTHER PUBLICATIONS

Shamblott et al., Human embryonic germ cell derivatives express a broad range of developmentally distinct markers and proliferate extensively in vitro, Proc Natl Acad Sci U S A. 98(1):113-8, 2001.*
Itskovitz-Eldor, et al., Differentiation of Human Embryonic Stem Cells into Embryoid Bodies Comprising the Three Embryonic Germ Layers, Molecular Medicine, 6, 88-95, 2000.
Willett, et al., Wnt Proteins are lipid-modified and can act as stem cell growth factors, Nature, 423, 448-452, 2003.
Ang et al., "HNF-3beta is essential for node and notochord formation in mouse development," *Cell*, (1994) 78:561-574.
Arnold et al., "Brachyury is a target gene of the Wnt/beta-catenin signaling pathway," *Mech. Dev.*, (2000) 91:249-258.

(Continued)

*Primary Examiner* — Peter Paras, Jr.
*Assistant Examiner* — David A Montanari
(74) *Attorney, Agent, or Firm* — Kilpatrick Townsend & Stockton LLP

(57) ABSTRACT

Disclosed herein are cell cultures comprising definitive endoderm cells and methods of producing the same. Also disclosed herein are cell populations comprising substantially purified definitive endoderm cells as well as methods for enriching, isolating and purifying definitive endoderm cells from other cell types.

17 Claims, 40 Drawing Sheets

(56) References Cited

FOREIGN PATENT DOCUMENTS

| | | |
|---|---|---|
| WO | WO 98/18943 | 5/1998 |
| WO | WO 98/30679 | 7/1998 |
| WO | WO 99/13915 | 3/1999 |
| WO | WO 00/29442 | 5/2000 |
| WO | WO 02/10347 | 2/2002 |
| WO | WO 02/34880 | 5/2002 |
| WO | WO 02/059278 | 8/2002 |
| WO | WO 03/050249 A2 | 6/2003 |
| WO | WO 03/050249 A3 | 6/2003 |
| WO | WO 03/100026 | 12/2003 |
| WO | WO 2004/098490 | 11/2004 |
| WO | WO 2005/017131 | 2/2005 |
| WO | WO 2005/033294 | 4/2005 |
| WO | WO 2005/045001 | 5/2005 |
| WO | WO 2005/063971 | 7/2005 |
| WO | WO 2005/097977 | 10/2005 |
| WO | WO 2005/097980 A2 | 10/2005 |
| WO | WO 2005/116073 | 12/2005 |
| WO | WO 2006/016999 | 2/2006 |
| WO | WO 2006/017134 | 2/2006 |
| WO | WO 2006/020919 A2 | 2/2006 |
| WO | WO 2006/034873 | 4/2006 |
| WO | WO 2006/083782 | 8/2006 |
| WO | WO 2007/002210 | 1/2007 |
| WO | WO 2007/002210 A2 | 1/2007 |
| WO | WO 2007/088372 | 8/2007 |

OTHER PUBLICATIONS

Bachiller et al., "The organizer factors chordin and noggin are required for mouse forebrain development," *Nature*, (2000) 403:658-661.

Barbacci, et al. "Variant Hepatocyte Nuclear Factor 1 Is Required for Visceral Endoderm Specification" (1999) Development 126:4795-4805.

Barringer et al., "Blunt-end and single-strand ligations by *Escherichia coli* ligase: influence on an in vitro amplification schemem," *Gene*, (1990) 89(1):117-22.

Battle et al., "The transcription factor snail is a repressor of E-cadherin gene expression in epithelial tumour cells,"*Nat. Cell. Biol.*, (2000) 2:84-89.

Blum et al., "Gastrulation in the mouse: the role of the homebox gene goosecoid," *Cell*, (1992) 69:1097-1106.

Bordonaro et al., "Cell type—a promoter—dependent modulation of the Wnt signaling pathway by sodium butyrate," *Int. J. Cancer* (2002) 97(1):42-51.

Brennan et al., "*Nodal* signalling in the epiblast patterns the early mouse embryo," *Nature*, (2001) 411:965-969.

Brunt, "Amplifying genes: PCR and its alternatives," *Biotechnology*, (1990) 8(4):291-4.

Candia et al., "Differential localization of mox-1 and mox-2 proteins indicates distinct roles during development," *Int. J. Dev. Biol.* (1996), 40:1179-1184.

Candia et al., "*Mox-1* and *Mox-2* define a novel homeobox gene subfamily and are differentially expressed during early mesodermal patterning in mouse embryos,"*Development* (1992), 116:1123-1136.

Cereghini, et al. "Expression Patterns of vHNF1 and HNF1 Homeoproteins in Early Postimplantation Embryos Suggest Distinct and Sequential Developmental Roles" (1992) Development 116:783-797.

Chen et al., "Retinoic acid signaling is essential for pancreas development and promotes endocrine at the expense of exocrine cell differentiation in *xenopus*," *Developmental Biology*, (2004) 271:144-160.

Chen et al., "Suppression of ES cell differentiation by retinol (vitamin A) via the overexpression of Nanog," *Differentiation* (2007) 75(8):682-93.

Chin et al., "Induced pluripotent stem cells and embyronic stem cells are distinguished by gene expression signatures," *Cell Stem Cell* (2009) 5(1):111-23.

Ciani et al., "WNTs in the vertebrate nervous system: from patterning to neuronal connectivity," *Nat. Rev. Neurosci.* (2005) 6(5):351-62.

Ciruna et al., "Chimeric analysis of *fibroblast growth factor receptor-1 (Fgfr1)* Function: a role for FGFR1 in morphogenetic movement through the primitive streak," *Development*, (1997) 124:2829-2841.

Ciruna et al., "FGF signaling regulates mesoderm cell fate specification and morphogenetic movement at the primitive streak," *Development*, (1997) 124:2829-2841.

Clackson et al., "Making antibody fragments using phage display libraries," *Nature*, (1991) 352(6336):624-8.

Collombat et al., "Specifying pancreatic endocrine cell fates," *Mech. Dev.* (2006) 123(7):501-12.

Dang et al., "Controlled, scalable embryonic stem cell differentiation culture," *Stem Cells*, (2004) 22:275-282.

Database UniProt, "1-acyl-sn-glycerol-3-phosphate acyltransferase gmma (EC 2.3.1.51) (1-AGP acyltransferase 3) (1-AGPAT 3) (Lyspohosphatidic acid acyltransfearse gamma) (LPAAT-gamma) (1-acylglycerol-3-phosphate 0-acyltransfearse 3)" retrieved from EBI accession No. UNIPROT: Q9NRZ7 on Oct. 1, 2000.

de Caestecker, "The transforming growth factor-beta superfamily of receptors," *Cytokine Growth Factor* (2004) Rev 15:1-11.

Dudas et al., "The homeobox transcription factor Prox1 is highly conserved in embryonic hepatoblasts and in adult and transformed hepatocytes, but is absent from bile duct epithelium," *Ant. Embryol. (Berl.)* (2004).

Elghanian et al., "Selective Colorimetric Detection of Polynucleotides Based on the Distance-Dependent Optical Properties of Gold Nanoparticles," *Science*, (1997) 277(5329):1078-1081.

Elms et al., "Overlapping and distinct expression domain of *Zic2* and *Zic3* during mouse gastrulation," *Gene Expression Patterns*, (2004) 4:505-511.

Gardner, "Stem cells and regenerative medicine: principles, prospects and problems," *C.R. Biol.* (2007) 330(6-7):465-73.

Guatelli et al., "Isothermal, in vitro amplification of nucleic acids by a multienzyme reaction modeled after retroviral replication," *Proc. Natl. Acad. Sci. USA*, (1990) 87(5):1874-8.

Gupta et al., "Pharmacological evidence for complex and multiple site interaction of CXCR4 with SDF-1alpha: implications for development of selective CXCR4 antagonists", Immunol. Lett., (2001), 78(1):29-34.

Haegel, et al., "Lack of β-catenin Affects Mouse Development at Gastrulation" *Development* (1995) 121: 3529-3537.

Hallonet, et al., "Maintenance of the Specification of the Anterior Definitive Endoderm and Forebrain Depends on the Axial Mesendoderm: A Study Using *HNF3β/Foxa2* Conditional Mutants" *Dev Biol* (2002) 243: 20-33.

Hansson, et al. "Artifactual Insulin Release from Differentiated Embryonic Stem Cells" (2004) Diabetes 53:2603-2609.

Harrison et al., "Pancreas Dorsal Lobe Agenesis and Abnormal Islets of Langerhans in *Hlxb9*-deficient Mice" *Nature Genetics* (1999) 23: 71-75.

Haumaitre, et al. "Functions of HNF1 Family Members in Differentiation of the Visceral Endoderm Cell Lineage" (2003) J. Biol. Chem. 278 (42): 40933-40942.

Henry, et al., "*Mixer*, a Homeobox Gene Required for Endoderm Development" *Science* (1998) 281: 91-96.

Herrmann, et al., "Cloning of the *T* Gene Required in Mesoderm Formation in the Mouse" *Nature* (1990) 343: 617-622.

Holland et al., "Experimental control of pancreatic development and maintenance," Proc Natl Acad Sci USA (2002) 99(19):12 236-12 241.

Houard, N., et al. "HNF-6-Independent Differentiation of Mouse Embryonic Stem Cells into Insulin-Producing Cells" (2003) Diabetologia 46:378-385.

Houde et al., "Intestinal epithelial cell differentiation involves activation of p38 mitogen-activated protein kinase that regulates the homeobox transcription factor CDX2," *J. Biol. Chem.* (2005) 276(24):21885-94.

Huelsken, et al., "Requirement for β-Catenin in Anterior-Posterior Axis Formation in Mice" *J Cell Biol* (2000) 148: 567-578.

(56) References Cited

OTHER PUBLICATIONS

Johannesson et al., "FGF4 and retionic acid direct differentiation of hESCs into PDX-1 expressing foregut endoderm in a time and concentration-dependent manner," *PLoS One* (2009) 4(3):e4794.

Jonsson, J., et al., "Insulin-promoter-factor 1 is required for pancreas development in mice", Nature, vol. 371. pp. 606-609, (1994).

Kalinichenko, et al., "The Forkhead Box F1 Transcription Factor is Expressed in Brain and Head Mesenchyme During Mouse Embryonic Development" Gene Expr Patterns (2003) 3: 153-158.

Kawahira, et al., "Hedghog Signaling Regulates Expansion of Pancreatic Epithelial Cells" *Developmental Biology* (2005) 280: 111-121.

Kawaji, et al., "Exploration of Novel Motifs Derived from Mouse cDNA Sequences" *Genome Research* (2002) 12: 367-378.

Khoo, et al., "Growth and Differentiation of Embryoid Bodies Derived from Human Embryonic Stem Cells: Effect of Glucose and Basic Fibroblast Growth Factor", Biology of Reproduction (2005) 73: 1147-1156.

Kimmel et al., "Preparation of cDNA and the generation of cDNA libraries: overview," *Methods Enzymol.*, (1987) 152:307-16.

Kinder, et al., "The Organizer of the Mouse Gastrula is Composed of a Dynamic Population of Progenitor Cells for the Axial Mesoderm" Development (2001) 128: 3623-3634.

Köhler et al., "Continuous cultures of fused cells secreting antibody of predefined specificity," *Nature*, (1975) 256(5517):495-7.

Kuo et al., "Roles of histone acetyltransferases and deacetylases in gene regulation", *BioEssays*, (1998) 20:615-626.

Kwoh et al., "Transcription-based amplification system and detection of amplified human immunodeficiency virus type 1 with a bead-based sandwich hybridization format," *Proc. Natl. Acad. Sci. USA*, (1989) 86(4):1173-7.

Landegren et al., "A ligase-mediated gene detection technique," *Science*, (1988) 241(4869):1077-80.

Lawson, et al., "Bmp4 is Required for the Generation of Primordial Germ Cells in the Mouse Embryo" Genes Dev (1999) 13: 424-436.

Liu, et al., "Requirement for Wnt3 in Vertebrate Axis Formation" Nat Genet (1999) 22: 361-365.

Lomell et al., "Quantitative assays based on the use of replicatable hybridization probes," *J. Clin. Chem.*, (1989) 35(9):1826-31.

Lowe et al., "Genetic dissection of *nodal* function in patterning the mouse embryo," *Development*, (2001) 128:1831-1843.

Mark et al., "Function of retinoid nuclear receptors: lessons from genetic and pharmacological dissections of the retinoic acid signaling pathway during mouse embryogenesis," *Annu. Rev. Pharmacol. Toxicol.* (2006) 46:451-80.

Martin, et al., "Dorsal Pancreas Agenesis in Retinoic Acid-Deficient Raldh2 Mutant Mice" Developmental Biology (2005) 284: 399-411.

Maruoka, et al., "Comparison of the Expression of Three Highly Related Genes, Fgf8, Fgf17 and Fgf18, in the Mouse Embryo" Mech Dev (1998) 74: 175-177.

Milne, et al. "Generation of Insulin-Expressing Cells from Mouse Embryonic Stem Cells" (2005) Biochemical and Biophysical Research Communications 328:399-403.

Molotkov, et al., "Retinoic Acid Generated by Raldh2 in Mesoderm Is Required for Mouse Dorsal Endodermal Pancreas Development" Development Dynamics (2005) 232: 950-957.

Nagai, et al., "The Expression of the Mouse Zic1, Zic2, and Zic3 Gene Suggests an Essential Role for Zic Genes in Body Pattern Formation" Dev Biol (1997) 182: 299-313.

Nakagawa, et al., "Recruitment and Activation of Rac1 by the Formation of E-cadherin-mediated Cell-cell Adhesion Sites" J. Cell Science (2001) 114(10): 1829-1838.

Nieto, et al., "Cloning and Developmental Expression of Sna, a Murine Homologue of the *Drosophila* snail Gene" Development (1992) 116: 227-237.

Nieto, M.A., The Snail Superfamily of Zinc-Finger Transcription Factors Nat Rev Mol Cell Biol (2002) 3: 155-166.

Niimi, et al. "SOX7 and SOX17 Regulate the Parietal Endoderm-Specific Enhancer Activity of Mouse Laminin Alpha1 Gene." (2004) J. Biol. Chem. 279 (36): 38055-38061.

Niswander, L. & Martin, G.R., "Fgf-4 Expression During Gastrulation, Myogenesis, Limb and Tooth Development in the Mouse" Development (1992) 114: 755-768.

Offield, et al., "PDX-1 is Required for Pancreatic Outgrowth and Differentiation of the Rostral Duodenum" Development (1996) 122: 983-995.

Ohlsson et al., "Embryonic stem cells express growth hormone receptors: regulation by retenoic acid," *Endocrinology* (1993) 133(6):2897-2903.

Ormestad, et al., "Differences in the Embryonic Expression Patterns of Mouse Foxf1 and -2 Match Their Distinct Mutant Phenotypes" Developmental Dynamics (2004) 229: 328-333.

Pearce, J.J. & Evans, M.J., "Mml, a Mouse Mix-like Gene Expressed in the Primitive Streak" Mech Dev (1999) 87: 189-192.

Pera, et al., "Regulation of Human Embryonic Stem Cell Differentiation by BMP-2 and its Antagonist Noggin" J Cell Sci (2004) 117: 1269-1280.

Perea-Gomez, et al., "Initiation of Gastrulation in the Mouse Embryo is Preceded by an Apparent Shift in the Orientation of the Anterior-Posterior Axis" Curr Biol (2004) 14: 197-207.

Pesce, M. & Scholer, H.R., "Oct. 4: Gatekeeper in the Beginnings of Mammalian Development" Stem Cells (2001) 19: 271-278.

Pevny, et al., "A Role for SOX1 in Neural Determination" Development (1998) 125: 1967-1978.

Price et al., "Serum-free media for neural cell cultures," *Protocols for Neural Cell Culture, 3rd Ed.*, Fedoroff and Richardson (Eds.) Humana Press, Totowa, New Jersey 255-264, 2001.

Rajagopal, et al. "Insulin Staining of ES Cell Progeny from Insulin Uptake" (2003) Science 299:363.

Ramiya et al., "Reversal of insulin-dependent diabetes using islets generated in vitro from pancreatic stem cells," *Nature Medicine* (2000) 6:278-282.

Reue, "mRNA quantitation techniques: considerations for experimental design and application," *The Journal of Nutrition*, (1998) 128(11):2038-2044.

Robb, L. & Tam, P.P., "Gastrula Organiser and Embryonic Patterning in the Mouse" Seminars in Cell & Dev. Biol. (2004) 15: 543-554.

Robertson, "Teratocarcinomas and embryonic stem cells: A practical approach," IRL Press 1987.

Rossant, J. & Tam, P.P., "Emerging Asymmetry and Embryonic Patterning in Early Mouse Development" Dev Cell (2004) 7: 155-164.

Saarma et al., "GDNF—a stranger in the TGF—superfamily?" Eur. J. Biochem. (2000) 267(24):6968-71.

Sasaki et al., "Differential expression of multiple fork head related genes during gastrulation and axial pattern formation in the mouse embryo", *Development*, (1993) 118:47-59.

Schwartz, et al. "Defined Conditions for Development of Functional Hepatic Cells from Human Embryonic Stem Cells" Stem Cells and Development (2005) 14(6): 643-655.

Shalaby, et al., "Failure of Blood-Island Formation and Vasculogenesis in Flk-1-deficient Mice" Nature (1995) 376: 62-66.

Shirahashi, et al., "Differentiation of Human and Mouse Embryonic Stem Cells Along a Hepatocyte Lineage" Cell Transplantation (2004) 13: 197-211.

Shiraki, "TGF-beta signaling potentiates differentiation of embryonic stem cells to PDx-1 expressing endodermal cells," *Genes to Cells* (2005) 21:405-412.

Shook, D. & Keller, R., "Mechanisms, Mechanics and Function of Epithelial-Mesenchymal Transitions in Early Development" Mech Dev (2003) 120: 1351-1383.

Sinner, et al., "Sox17 and β-Catenin Cooperate to Regulate the Transcription of Endodermal Genes" Development (2004) 131: 3069-3080.

Sooknanan et al., "NASBA: a detection and amplification system uniquely suited for RNA," *Nature Biotechnology*, (1995) 13:563-564.

Stafford, et al., "A Conserved Role for Retinoid Signaling in Verterbrate Pancreas Development" Dev Genes Evol. (2004) 214: 432-441.

Stainier, D.Y.R., "A Glimpse into the Molecular Entrails of Endoderm Formation" Genes Dev (2002) 16: 893-907.

(56) References Cited

OTHER PUBLICATIONS

Stemmler, et al., "Analysis of Regulatory Elements of E-Cadherin with Reporter Gene Constructs in Transgenic Mouse Embryos" Developmental Dynamics (2003) 227: 238-245.

Stoffers, et al., "Early-onset Type-II Diabetes Mellitus (MODY4) Linked to IPF1" Nature Genetics (1997) 17: 138-139.

Stoffers, et al., "Pancreatic Agenesis Attributable to a Single Nucleotide Deletion in the Human IPF1 Gene Coding Sequence" Nature Genetics (1997) 15: 106-110.

Sun et al., "Conditional inactivation of Fgf4 reveals complexity of signaling during limb bud development," *Nat. Genet.*, (2000) 25:83-86.

Sun, et al., "Targeted Disruption of Fgf8 Causes Failure of Cell Migration in the Gastrulating Mouse Embryo" Genes Dev (1999) 13: 1834-1846.

Tada, et al. "Characterization of Mesendoderm: A Diverging Point of the Definitive Endoderm and Mesoderm in Embryonic Stem Cell Differentiation Culture." (2005) Development 132: 4363-4374.

Takahashi et al., "Induction of pluripotent stem cells from adult human fibroblasts by defined factors," *Cell* (2007) 131(5):861-72.

Terskikh et al., ""Peptabody": a new type of high avidity binding protein," *Proc. Natl. Acad. Sci. USA*, (1997) 94(5):1663-8.

Thelwell et al., "Mode of action and application of Scorpion primers to mutation detection," *Nucleic Acids Res.*, (2000) 28(19):3752-61.

Thisse et al., "Antivin, a novel and divergent member of the TGF—superfamily, negatively regulates mesoderm induction," *Development* (1999) 126(2):229-40.

Thomas, et al., "The Murine Gene, Traube, Is Essential for the Growth of Preimplantation Embryos" Dev Biol (2000) 227: 324-342.

Trueba et al., "PAX8, TITF1, and FOXE1 gene expression patterns during human development: new insights into human thyroid deevlopment and thyroid dysgenesis-associated malformations," *J. Clin. Endocrinol. Metab.* (2005) 90(1):455-62.

Tyagi et al., "Molecular beacons: probes that fluoresce upon hybridization," *Nat. Biotechnol.*, (1996) 14(3):303-8.

Valdimarsdottir et al., "Functions of the TFGb superfamily in human embryonic stem cells," *APMIS* (2005) 113(11-12):773-89.

Weinstein, D.C. et al. The winged-helix transcription factor HNF-3 beta is required for notochord development in the mouse embryo. Cell 78, 575-588 (1994).

Wilding et al., "The role of pdxl and HNF6 in proliferation and differentiation of endorine precursors," (2005) Diabetes Metab Res Rev. 20(2):114-23.

Wilson et al., "Streptozotocin interactions with pancreatic beta cells and the induction of insulin-dependent diabetes," *Current Topics Microbiol. Immunol.* (1990) 158:27-54.

Wu et al., "The ligation amplification reaction (LAR)—amplification of specific DNA sequences using sequential rounds of template-dependent ligation.," *Genomics*, (1989): 4(4):560-9.

Xu et al., "Feeder-free growth of undifferentiated human embryonic stem cells," *Nat. Biotechnol.* (2001) 19(10):971.

Yamaguchi, et al., "flk-1, an flt-related Receptor Tyrosine Kinase is an Early Marker for Endothelial Cell Precursors" Development (1993) 118: 489-498.

Yamaguchi, et al., "T (Brachyury) is a Direct Target of Wnt3a During Paraxial Mesoderm Specification" Genes Dev (1999) 13: 3185-3190.

Yang, et al., "Disabled-2 is Essential for Endodermal Cell Positioning and Structure Formation During Mouse Embryogenesis" Dev Biol (2002) 251: 27-44.

Yu et al., "Human induced pluripotent stem cells free of vector and transgene sequences," *Science* (2007) 324: 797-801.

Zhang et al., "Highly efficient differentiation of human ES cells and IPS cells into mature pancreatic insulin-producing cells," *Cell Research* (2009): 429-438.

Activin A, Product Information from SIGMA-Aldrich, 2010.

Kim, et al., Pancreas development is promoted by cyclopamine, a Hedgehog signaling inhibitor, Proc. Natl. Acad. Sci. USA vol. 95, pp. 13036-13041, Oct. 1998.

Wiles and Johansson, "Embryonic Stem Cell Development in a Chemically Defined Medium," Experimental Cell Research (1999) 247:241-248.

Abe, et al., "Endoderm-Specific Gene Expression in Embryonic Stem Cells Differentiated to Embryoid Bodies." Experimental Cell Research. (1996) 229(1): 27-34.

Alexander, et al., "Casanova Plays an Early and Essential Role in Endoderm Formation in Zebrafish" Dev Biol (1999) 215: 343-357.

Alexander, J., and Stainier, D. Y., "A Molecular Pathway Leading to Endoderm Formation in Zebrafish" Curr Biol (1999) 9: 1147-1157.

Ang, et al. "The Formation and Maintenance of the Definitive Endoderm Lineage in the Mouse: Involvement of HNF3/Forkhead Proteins" Development (1993) 119: 1301-1315.

Aoki, et al., "Regulation of Nodal Signalling and Mesendoderm Formation by TARAM-A, A Tgfbeta-Related Type I Receptor" Dev Biol (2002) 241: 273-288.

Assady et al. "Insulin Production by Human Embryonic Stem Cells" Diabetes (2001) 50(8): 1691-1697.

Bain, et al., "Embryonic Stem Cells Express Neuronal Properties in Vitro." Developmental Biology (1995) 168: 342-357.

Barry, et al., "The Production of Monoclonal Antibodies by Genetic Immunization" Biotechniques (1994) 16: 616-620.

Beck, et al., "Extra-Embryonic Proteases Regulate Nodal Signalling During Gastrulation" Nat Cell Biol (2002) 4: 981-985.

Beddington, et al. "Brachyury—A Gene Affecting Mouse Gastrulation and Early Organogenesis" Dev Suppl, (1992) 157-165.

Bendall, et al. "IGF and FGF Cooperatively Establish Regulatory Stem Cell Niche of Pluripotent Human Cells In Vitro." Nature (2007), 448; 1015-1021.

Bongso, et al., "Isolation and Culture of Inner Cell Mass Cells From Human Blastocysts" Hum Reprod (1994) 9: 2110-2117.

Bost, et al., "Retinoic Acid Activation of the ERK Pathway is Required for Embryonic Stem Cell Commitment into the Adipocyte Lineage." Biochem. J. (2002) 361: 621-627.

Chang, et al., "Genetic Analysis of the Mammalian Transforming Growth Factor-Beta Superfamily" Endocr Rev (2002) 23: 787-823.

Conley et al. "BMPs Regulate Differentiation of a Putative Visceral Endoderm Layer Within Human Embryonic Stem-Cell-Derived Embryoid Bodies" (2007) Biochem Cell Biol 85: 121-132.

Conlon, et al., "A primary requirement for nodal in the formation and maintenance of the primitive streak in the mouse" Development (1994) 120: 1919-1928.

Costaglia, et al., "Genetic Immunization Against the Human Thyrotropin Receptor Causes Thyroiditis and Allows Production of Monoclonal Antibodies Recognizing the Native Receptor" J. Immunol. (1998) 160: 1458-1465.

Czyz et al. "Embryonic Stem Cell Differentiation: The Role of Extracellular Factors" Differentiation (2001) 68(4-5): 167-174.

Daheron et al. "LIF/STAT3 Signaling Fails to Maintain Self-Renewal of Human Embryonic Stem Cells" Stem Cells (2004) 22: 770-778.

D'Amour et al. "Production of pancreatic hormone-expressing endocrine cells from human embryonic stem cells" (Nov. 1, 2006) Nature Biotechnology 24, 1392-1401.

D'Amour, et al., "Efficient Differentiation of Human Embryonic Stem Cells to Definitive Endoderm" Nature Biotechnology (2005) 23(12): 1534-1541.

Dani, et al., "Differentiation of Embryonic Stem Cells into Adipocytes in Vitro." J. Cell Science (1997) 110: 1279-1285.

Defelice Mario, et al., "TTF-1 Phosphorylation is Required for Peripheral Lung Morphogenesis, Perinatal Survival, and Tissue-Specific Gene Expression" J. Biological Chemistry (2003) 278(37): 35574-35583.

Dougan, et al., "The Role of the Zebrafish Nodal-Related Genes Squint and Cyclops in Patterning of Mesendoderm" Development (2003) 130: 1837-1851.

Edlund, H., "Factors Controlling Pancreatic Cell Differentiation and Function," Diabetologia (2001) 44(9): 1071-1079.

Falasca, et al., "Retinoic Acid Treatment Induces Apoptosis or Expression of a More Differentiated Phenotype on Different Fractions of Cultured Fetal Rat Hepatocytes" Hepatology (1998) 28(3): 727-737.

(56) References Cited

OTHER PUBLICATIONS

Fehling, et al., "Development and Disease: Tracking Mesoderm Induction and its Specification to the Hemangioblast during Embryonic Stem Cell Differentiation" Development (2003) 130: 4217-4227.
Feldman, et al., "Zebrafish Organizer Development and Germ-Layer Formation Require Nodal-Related Signals" Nature (1998) 395: 181-185.
Feng, et al., "HIV-1 Entry Cofactor: Functional Cdna Cloning of a Seven-Transmembrane, G Protein-Coupled Receptor" Science (1996) 272: 872-877.
Freund, et al. "Insulin Redirect Differentiation from Cardiogenic Mesoderm and Endoderm to Neuroectoderm in Differentiating Human Embryonic Stem Cells." Stem Cells (2007), published online Dec. 20, 2007.
Futaki, et al., "Molecular Basis of Constitutive Production of Basement Membrane Components: Gene Expression Profiles of Engelbreth-Holm-Swarm Tumor and F9 Embryonal Carcinoma Cells" J Biol Chem. (2003) 278(50): 50691-50701.
Goumans, et al., "Mouse Embryonic Stem Cells with Aberrant Transforming Growth Factor B signaling Exhibit Impaired Differentiation in Vitro and In Vivo" Differentiation (1998) 63: 103-113.
Grapin-Botton, A., and Melton, D. A., "Endoderm Development: From Patterning to Organogenesis" Trends Genet (2000) 16: 124-130.
Hamazaki, et al., "Hepatic Maturation in Differentiating Embryonic Stem Cells in Vitro" FEBS Letter (2001) 497(1): 15-19.
Harris, T. M., and Childs, G., "Global Gene Expression Patterns During Differentiation of F9 Embryonal Carcinoma Cells Into Parietal Endoderm" Funct Integr Genomics (2002) 2: 105-119.
Hogan, B. L., "Bone Morphogenetic Proteins in Development" Curr Opin Genet Dev (1996) 6: 432-438.
Howe, et al., "Expression of SPARC/Osteonectin Transcript in Murine Embryos and Gonads" Differentiation (1998) 37: 20-25.
Hudson, et al., "Xsox17alpha and -beta Mediate Endoderm Formation in Xenopus" Cell (1997) 91: 397-405.
Humphrey, et al. "Maintenance of Pluripotency in Human Embryonic Stem Cells is STAT3 Independent" Stem Cells (2004) 22: 522-530.
Imada, et al., "Fetomodulin: Marker Surface Protein of Fetal Development Which Is Modulatable by Cyclic AMP" Dev Biol (1987)122: 483-491.
Jain, et al., "Glucose Control and Long-Term Survival in Breeding/Worcester Rats After Intraperitoneal Implantation of Hydrophilic Macrobeads containing Porcine Islets without Immunosuppression" Transplantation (1999) 68(11): 1693-1700.
Jones, et al., "Differences Between Human and Mouse Alpha-Fetoprotein Expression During Early Development" J. Anat. (2001) 198: 555-559.
Kahan, et al., "Pancreatic Precursors and Differentiated Islet Cell Types from Murine Embryonic Stem Cells: An In Vitro Model to Study Islet Differentiation" Diabetes (2003) 52(8): 2016-2024.
Kanai-Azuma, et al., "Depletion of Definitive Gut Endoderm in Sox17-Null Mutant Mice" Development (2002) 129: 2367-2379.
Katoh, M., "Expression of Human SOX7 in Normal Tissues and Tumors" Int J Mol Med (2002) 9: 363-368.
Keller, G.M., "In Vitro Differentiation of Embryonic Stem Cells" Curr Op Cell Biol (1995) 7: 862-896.
Kieffer, T.J., and J.F. Habener, "The Glucagon-Like Peptides" Endocrinology Reviews (1999) 20(6): 876-913.
Kikuchi, et al., "Casanova Encodes a Novel Sox-Related Protein Necessary and Sufficient for Early Endoderm Formation in Zebrafish" Genes Dev (2001) 15: 1493-1505.
Kilpatrick, et al., "Gene Gun Delivered DNA-Based Immunizations Mediate Rapid Production of Murine Monoclonal Antibodies to the Flt-3 Receptor" Hybridoma (1998) 17: 569-576.
Kim, C. H., and Broxmeyer, H. E., "Chemokines: Signal Lamps for Trafficking of T and B Cells for Development and Effector Function" J Leukoc Biol (1999) 65: 6-15.

Kimelman, D., and Griffin, K. J., "Vertebrate Mesendoderm Induction and Patterning" Curr Opin Genet Dev (2000)10: 350-356.
Krasemann, et al., "Generation of Monoclonal Antibodies Against Proteins With an Unconventional Nucleic Acid-Based Immunization Strategy" J. Biotechnol. (1999) 73: 119-129.
Kubo, et al., "Development of definitive endoderm from embryonic stem cells in culture" Development (2004)131: 1651-1662.
Kumar, et al., "Nodal Signaling Uses Activin and Transforming Growth Factor-Beta Receptor-Regulated Regulated Smads" J Biol Chem (2001) 276: 656-661.
Labosky, et al., "Embryonic Germ Cell Lines and Their Derivation From Mouse Primordial Germ Cells" Ciba Found Symp (1994) 182: 157-168; discussion: 168-178.
Labosky, et al., "Mouse Embryonic Germ (EG) Cell Lines: Transmission Through the Germline and Differences in the Methylation Imprint of Insulin-Like Growth Factor 2 Receptor (Igf2r) Gene Compared With Embryonic Stem (ES) Cell Lines" Development (1994) 120: 3197-3204.
Latif, et al., "A Simple Method of Staining Fresh and Cultured Islets," Transplantation (1998) 45(4): 827-830.
Lickert, et al., "Formation of Multiple Hearts in Mice Following Deletion of Beta-Catenin in the Embryonic Endoderm" Dev Cell (2002) 3: 171-181.
Loebel et al., "A gut feeling," Nat. Biotechnol., (2005) 23(12):1491-2.
Lu, et al., "From Fertilization to Gastrulation: Axis Formation in the Mouse Embryo" Curr Opin Genet Dev (2001) 11: 384-392.
Lumelsky, et al., "Differentiation of Embryonic Stem Cells to Insulin-Secreting Structures Similar to Pancreatic Islets" Science (2001) 292: 1389-1394.
Ma, et al., "The chemokine receptor CXCR4 is required for the retention of B lineage and granulocytic precursors within the bone marrow microenvironment" Immunity (1999)10: 463-471.
Matsuda, et al., "STAT3 Activation is Sufficient to Maintain an Undifferentiated State of Mouse Embryonic Stem Cells" EMBO J (1999) 18(15): 4261-4269.
McGrath et al., "Embryonic expression and function of the chemoskine SDF-1 and its receptor, CXCR4," Dev. Biol. 213:442-456, 1999.
McGrath et al. "Expression of Homeobox Genes, Including and Insulin Promoting Factor, in the Murine Yolk Sac at the Time of Hematopoietic Initiation" (1997) Mol Reprod Dev 48: 145-153.
McLean et al. "Activin A Efficiently Specifies Definitive Endoderm from Human Embryonic Stem Cells Only When Phosphtidylinositol 3-Kinase Signaling is Suppressed" (2007) Stem Cells 25: 29-38.
Micallef, et al., "Retinoic Acid Induces Pdx1-positive Endoderm in Differentiating Mouse Embryonic Stem Cells" Diabetes (2005) 54(2): 301-305.
Millonig, et al., "Molecular Analysis of the Distal Enhancer of the Mouse Alpha-Fetoprotein Gene" Mol. Cell Biol. (1995) 15: 3848-3856.
Miyazono, et al., "Divergence and Convergence of TGF-beta/BMP Signaling" J Cell Physiol (2001)187: 265-276.
Mizusawa, et al., "Differentiation Phenotypes of Pancreatic Islet Beta- and Alpha-Cells are Closely Related with Homeotic Genes and a Group of Defferentially Expressed Genes" Gene: An Int. Journal on Genes and Genomes (2004) 331: 53-63.
Moriya, et al., "In Vitro Pancreas Formation from Xenopus Ectoderm Treated with Activin and Retinoic Acid" Develop. Growth Differ. (2000) 42: 593-602.
Nagasawa, et al., "Defects of B-cell Lymphopoiesis and Bone-Marrow Myelopoiesis in Mice Lacking the CXC Chemokine PBSF/SDF-1" Nature (1996) 382: 635-638.
Niwa, H., "Molecular mechanism to maintain stem cell renewal of ES cells" Cell Struct Funct (2001) 26: 137-148.
Ogura, et al., "Behavioral abnormalities of Zic1 and Zic2 mutant mice: implications as models for human neurological disorders" Behav Genet (2001) 31: 317-324.
O'Hare, et al., "Conditional Immortilization of Freshly Isolated Human Mammary Fibroblast and Endothelial Cells" Proc. Nat. Acad. Sci. (2001) 98: 646-651.

(56) References Cited

OTHER PUBLICATIONS

Phillips, et al., "Differentiation of Embryonic Stem Cells for Pharmacological Studies on Adipose Cells" Pharmacological Research (2003) 47:263-268.
Rambhatla, et al. "Generation of Hepatocyte-Like Cells From Human Embryonic Stem Cells." Cell Transplantation (2003), vol. 12, pp. 1-11.
Reubinoff, et al., "Embryonic Stem Cell Lines From Human Blastocysts: Somatic Differentiation In Vitro" Nat Biotechnol (2000) 18: 399-404.
Roche et al. "Ectodermal commitment of insulin-producing cells derived from mouse embryonic stem cells" Faseb J (2005) 19: 1341-3.
Rodaway, A., and Patient, R., "Mesendoderm: An Ancient Germ Layer?" Cell (2001) 105: 169-172.
Rodaway, et al., "Induction of the Mesendoderm in the Zebrafish Germ Ring by Yolk Cell-Derived Tgf-Beta Family Signals and Discrimination of Mesoderm and Endoderm by FGF" Development (1999) 126: 3067-3078.
Rohr, et al. "Zebrafish Zic1 Expression in Brain and Somites is Affected by BMP and Hedgehog Signalling" Mech Dev (1999) 85: 147-159.
Sander, M. and M.S. German, "The Beta Cell Transcription Factors and Development of the Pancreas" J. Molecular Medicine (1997) 75(5): 327-340.
Schier, A. F., "Nodal Signaling in Vertebrate Development" Annu Rev Cell Dev Biol (2003) 19: 589-621.
Schmolke, et al., "Identification of Hepatitis G Virus Particles in Human Serum by E2-Specific Monoclonal Antibodies Generated by DNA Immunization" J. Virol. (1998) 72: 4541-4545.
Schoenwolf, G. C., and Smith, J. L., "Gastrulation and Early Mesodermal Patterning in Vertebrates" Methods Mol Biol (2000) 135: 113-125.
Schuldiner, et al., "Effects of Eight Growth Factors on the Differentiation of Cell Derived from Human Embryonic Stem Cells" Proc. Natl. Sci. (2000) 97: 11307-11312.
Segev, Hanna et al. "Differentiation of Human Embryonic Stem Cells into Insulin-Producing Clusters." Stem Cells (2004), vol. 22, pp. 265-274.
Shamblott, et al., "Derivation of Pluripotent Stem Cells From Cultured Human Primordial Germ Cells" Proc Natl Acad Sci USA (1998) 95: 13726-13731.
Shapiro, et al., "Could fewer islet cells be transplanted in type 1 diabetes? Insulin independence should be a dominant force in islet transplantation," *Bmj* 322:861, 2001.
Shapiro, et al., "Islet Transplantation in Seven Patients With Type 1 Diabetes Mellitus Using a Glucocorticoid-Free Immunosuppressive Regimen" N Engl J Med (2000) 343: 230-238.
Shapiro, et al., "Pancreatic Islet Transplantation in the Treatment of Diabetes Mellitus" Best Pract Res Clin Endocrinol Metab (2000) 15: 241-264.
Shi, Yan, et al. "Inducing Embryonic Stem Cells to Differentiate into Pancreatic β Cells by a Novel Three-Step Approach with Activin A and All-Trans Retinoic Acid." Stem Cells (2005), vol. 23, pp. 656-662.
Shiozawa, et al., "Cloning and Characterization of *Xenopus laevis* xSox7 cDNA" Biochim Biophys Acta (1996)1309: 73-76.
Skoudy, et al. "Transforming Growth Factor (TGF) beta, Fibroblast Growth Factor (FGF) and Retinoid Signaling Pathways Promote Pancreatic Exocrine Gene Expression in Mouse Embryonic Stem Cells" Biochemical J. (2004) 379(Pt 3): 749-756.
Smith, et al., "Upstream and Downstream From Brachyury, A Gene Required for Vertebrate Mesoderm Formation" Cold Spring Harb Symp Quant Biol (1997) 62: 337-346.
Smith, J., "Brachyury and the T-box Genes" Curr Opin Genet Dev (1997) 7: 474-480.
Soon-Shiong, P., "Treatment of Type I Diabetes using Encapsulated Islets" Advanced Drug Delivery Reviews (1999) 35: 259-270.
Soria, et al., "Insulin-Secreting Cells Derived from Embryonic Stem Cells Normalize Glycemia in Streptozotocin-Induced Diabetic Mice" Diabetes (2000) 49(2): 157-162.
Stafford et al., "Pancreatic development, proliferation and stem cells," *Meeting Abstract*, Oct. 18-19, National Institutes of Health, 2001.
Stafford, D. and Prince, V., "Retinoic Acid Signaling is Required for a Critical Early Step in Zebrafish Pancreatic Development" Current Biology (2002) 12: 1215-1220.
Suzuki, et al., "Cloned Cells Develop Renal Cortical Collecting Tubles" Nephron. (1994) 68: 118-124.
Takash, et al., "SOX7 Transcription Factor: Sequence, Chromosomal Localisation, Expression, Transactivation and Interference With Wnt Signalling" Nucleic Acids Res (2001) 29: 4274-4283.
Tam et al., "Early endoderm development in vertebrates: lineage differentiation and morphogenetic function," *Current Opinion Genet. Dev.*, (2003) 13(4):393-400.
Tam et al., "Gene function in mouse embryogenesis: get set for gastrulation," *Nat. Rev. Genet.*, (2007) 8(5):368-81.
Taniguchi, et al., "Isolation and Characterization of a Mouse SRY-related cDNA, mSox7" Biochim Biophys Acta (1999) 1445: 225-231.
Technau, U. "Brachyury, the Blastopore and the Evolution of the Mesoderm" Bioessays (2001) 23: 788-794.
Thomson, et al., "Embryonic Stem Cell Lines Derived from Human Blastocysts" Science (1998) 282: 1145-1147.
Tiedemann, et al., "Pluripotent cells (stem cells) and Their Determination and Differentiation in Early Vertebrate Embryogenesis" Develop. Growth Differ. (2001) 43: 469-502.
Tremblay, et al., "Formation of the definitive endoderm in mouse is a Smad2-dependent process" Development (2000) 127: 3079-3090.
Ulivieri, et al., "Generation of a Monoclonal Antibody to a Defined Portion of the *Heliobacter pylori* Vacuolating Cytotoxin by DNA Immunization" J. Biotechnol. (1996) 51: 191-194.
Urbach, et al., "Modeling Lesch-Nyhan Disease by Gene Targeting in Human Embryonic Stem Cells" Stem Cells (2004) 22: 635-641.
Vallier et al. "Nodal Inhibits Differentiation of Human Embryonic Stem Cells Along the Neuroectodermal Default Pathway" (2004) Developmental Biology 275, 403-421.
Vallier, et al. "Activin/Nodal and FGF Pathways Cooperate to Maintain Pluripotency of Human Embryonic Stem Cells" J Cell Sci. (2005) 118: 4495-509.
Vandesompele, et al., "Accurate Normalization of Real-Time Quantitative RT-PCR Data by Geometric Averaging of Multiple Internal Control Genes" Genome Biol (2002) 3(7): 1-12.
Varlet, et al., "Nodal Expression in the Primitive Endoderm is Required for Specification of the Anterior Axis During Mouse Gastrulation" Development (1997) 124: 1033-1044.
Vincent, et al., "Cell Fate Decisions Within the Mouse Organizer are Governed by Graded Nodal Signals" Genes Dev (2003) 17: 1646-1662.
Vogel, G. "Stem Cells are Coaxed to Produce Insulin" Science (2001) 292: 615-616.
Wang, et al. "Self-Renewal of Human embryonic Stem Cells Requires Insulin-Like Growth Factor-1 Receptor and ERBB2 Receptor Signaling." Blood (2007), 110; 4110-4119.
Wei, et al., "Transcriptome Profiling of Human and Murine ESCs Identifies Divergent Paths Required to Maintain the Stem Cell State" Stem Cells (2005) 23: 166-185.
Weiler-Guettler, et al., "Developmentally Regulated Gene Expression of Thrombomodulin in Postimplantation Mouse Embryos" Development (1996) 122: 2271-2281.
Weiler-Guettler, et al., "Thrombomodulin Gene Regulation by cAMP and Retinoic Acid in F9 Embryonal Carcinoma Cells" PNAS (1992) 89: 2155-2159.
Wells, J. M., and Melton, D. A. "Early Mouse Endoderm is Patterned by Soluble Factors From Adjacent Germ Layers" Development (2000) 127: 1563-1572.
Wells, J. M., and Melton, D. A., "Vertebrate Endoderm Development" Annu Rev Cell Dev Biol (1999) 15: 393-410.
Willison, K., "The Mouse Brachyury Gene and Mesoderm Formation" Trends Genet (1990) 6: 104-105.

(56) References Cited

OTHER PUBLICATIONS

Xu, et al. "BMP4 Initiates Human Embryonic Stem Cell Differentiation to Trophoblast." Nature Biotechnology (Dec. 2002), vol. 20, pp. 1261-1264.

Xu, et al., "Characterization and Enrichment of Cardiomyocytes Derived From Human Embryonic Stem Cells" Cellular Biology (2002) 91: 501-508.

Yasunaga, et al. "Induction and Monitoring of Definitive and Visceral Endoderm Differentiation of Mouse ES Cells." Nature Biotechnology (2005) 23: 1542-1550.

Ying, et al. "BMP Induction of Id Proteins Suppresses Differentiation and Sustains Embryonic Stem Cell Self-Renewal in Collaboration with STAT3." Cell (Oct. 31, 2003), vol. 115, pp. 281-292.

Yusuf et al., "Expression of chemokine receptor CXCR4 during chick embryo development," *Ant. Ebryol. (Berl)*, (2005) 210(1):35-41.

Zhao, G. Q., "Consequences of Knocking Out BMP Signaling in the Mouse" Genesis (2003) 35: 43-56.

Zhou, et al., "Nodal is a Novel TGF-beta-like Gene Expressed in the Mouse Node during Gastrulation" Nature (1993) 361: 543-547.

Zwaka, et al. "Homologous Recombination in Human Embryonic Stem Cells" Nature Biotechnology (2003) 21: 319-321.

International Preliminary Examination Report mailed Sep. 21, 2004.
International Search Report mailed Oct. 1, 2002.
PCT Written Opinion issued on Mar. 2, 2004.
Supplemental Partial European Search Report mailed Feb. 1, 2005.

\* cited by examiner (A)

(B)

(C)

DEFINITIVE ENDODERM

RELATED APPLICATIONS

This application is a continuation of U.S. patent application Ser. No. 11/021,618, filed Dec. 23, 2004, entitled "DEFINITIVE ENDODERM," which claims priority under 35 U.S.C. §119(e) to U.S. Provisional Patent Application No. 60/532,004, entitled DEFINITIVE ENDODERM, filed Dec. 23, 2003, and which claims priority under 35 U.S.C. §119(e) to U.S. Provisional Patent Application No. 60/586,566, entitled CHEMOKINE CELL SURFACE RECEPTOR FOR THE ISOLATION OF DEFINITIVE ENDODERM, filed Jul. 9, 2004, and which claims priority under 35 U.S.C. §119 (e) to U.S. Provisional Patent Application No. 60/587,942, entitled CHEMOKINE CELL SURFACE RECEPTOR FOR THE ISOLATION OF DEFINITIVE ENDODERM, filed Jul. 14, 2004. The disclosure of each of the above-listed priority applications is incorporated herein by reference in its entirety.

FIELD OF THE INVENTION

The present invention relates to the fields of medicine and cell biology. In particular, the present invention relates to compositions comprising mammalian definitive endoderm cells and methods of making, isolating and using such cells.

BACKGROUND

Human pluripotent stem cells, such as embryonic stem (ES) cells and embryonic germ (EG) cells, were first isolated in culture without fibroblast feeders in 1994 (Bongso et al., 1994) and with fibroblast feeders (Hogan, 1997). Later, Thomson, Reubinoff and Shamblott established continuous cultures of human ES and EG cells using mitotically inactivated mouse feeder layers (Reubinoff et al., 2000; Shamblott et al., 1998; Thomson et al., 1998).

Human ES and EG cells (hESCs) offer unique opportunities for investigating early stages of human development as well as for therapeutic intervention in several disease states, such as diabetes mellitus and Parkinson's disease. For example, the use of insulin-producing β-cells derived from hESCs would offer a vast improvement over current cell therapy procedures which utilize cells from donor pancreases. However, presently it is not known how to generate an insulin-producing β-cell from hESCs. As such, current cell therapy treatments for diabetes mellitus, which utilize islet cells from donor pancreases, are limited by the scarcity of high quality islet cells needed for transplant. Cell therapy for a single Type I diabetic patient requires a transplant of approximately $8 \times 10^8$ pancreatic islet cells. (Shapiro et al., 2000; Shapiro et al., 2001a; Shapiro et al., 2001b). As such, at least two healthy donor organs are required to obtain sufficient islet cells for a successful transplant. HESCs offer a source of starting material from which to develop substantial quantities of high quality differentiated cells for human cell therapies.

Two properties that make hESCs uniquely suited to cell therapy applications are pluripotence and the ability to maintain these cells in culture for prolonged periods without accumulation of genetic changes. Pluripotency is defined by the ability of hESCs to differentiate to derivatives of all 3 primary germ layers (endoderm, mesoderm, ectoderm) which, in turn, form all cell somatic types of the mature organism in addition to extraembryonic tissues (e.g. placenta) and germ cells. Although pluripotency imparts extraordinary utility upon hESCs, this property also poses unique challenges for the study and manipulation of these cells and their derivatives. Owing to the large variety of cell types that may arise in differentiating hESC cultures, the vast majority of cell types are produced at very low efficiencies. Additionally, success in evaluating production of any given cell type depends critically on defining appropriate markers. Achieving efficient, directed differentiation is of great importance for therapeutic application of hESCs.

In order to use hESCs as a starting material to generate cells that are useful in cell therapy applications, it would be advantageous to overcome the foregoing problems. For example, in order to achieve the level of cellular material required for islet cell transplantation therapy, it would be advantageous to efficiently direct hESCs toward the pancreatic islet/β-cell lineage at the very earliest stages of differentiation.

In addition to efficient direction of the differentiation process, it would also be beneficial to isolate and characterize intermediate cell types along the differentiation pathway towards the pancreatic islet/β-cell lineage and to use such cells as appropriate lineage precursors for further steps in the differentiation.

SUMMARY OF THE INVENTION

Some embodiments of the present invention relate to cell cultures comprising definitive endoderm cells, wherein the definitive endoderm cells are multipotent cells that can differentiate into cells of the gut tube or organs derived from the gut tube. In accordance with certain embodiments, the definitive endoderm cells are mammalian cells, and in a preferred embodiment, the definitive endoderm cells are human cells. In some embodiments of the present invention, definitive endoderm cells express or fail to significantly express certain markers. In some embodiments, one or more markers selected from SOX17, CXCR4, MIXL1, GATA4, HNF3b, GSC, FGF17, VWF, CALCR, FOXQ1, CMKOR1 and CRIP1 are expressed in definitive endoderm cells. In other embodiments, one or more markers selected from OCT4, alpha-fetoprotein (AFP), Thrombomodulin (TM), SPARC and SOX7 are not significantly expressed in definitive endoderm cells.

In accordance with other embodiments of the present invention, methods of producing definitive endoderm from pluripotent cells are described. In some embodiments, pluripotent cells are derived from a morula. In some embodiments, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells can originate from a variety of animal species including, but not limited to, various mammalian species including humans. In a preferred embodiment, human embryonic stem cells are used to produce definitive endoderm.

In some embodiments of the present invention, one or more growth factors are used in the differentiation process from pluripotent cell to definitive endoderm cell. The one or more growth factors used in the differentiation process can include growth factors from the TGFβ superfamily. In such embodiments, the one or more growth factors comprise the Nodal/Activin and/or the BMP subgroups of the TGFβ superfamily of growth factors. In some embodiments, the one or more growth factors are selected from the group consisting of Nodal, Activin A, Activin B, BMP4, Wnt3a or combinations of any of these growth factors.

Embodiments of the present invention also relate to populations of cells enriched in definitive endoderm cells. In certain embodiments, the definitive endoderm cells are isolated or substantially purified. In some embodiments, the isolated or substantially purified definitive endoderm cells express the SOX17 and/or the CXRC4 marker to a greater extent than the OCT4, AFP, TM, SPARC and/or SOX7 markers.

Methods for enriching a cell population with definitive endoderm are also contemplated. In some embodiments, definitive endoderm cells can be isolated or substantially purified from a mixed cell population by contacting the cells with a reagent that binds to a molecule that is present on the surface of definitive endoderm cells but which is not present on the surface of other cells in the mixed cell population, and then isolating the cells bound to the reagent. In certain embodiments, the molecule that is present on the surface of definitive endoderm cells is CXCR4.

Still other embodiments of the present invention relate to CXCR4 antibodies, SDF-1 ligands or other ligands for CXCR4 can be used to obtain definitive endoderm cells in an enriched, isolated or substantially purified form. For example, a CXCR4 antibody, an SDF-1 ligand or another ligand for CXCR4 can be used as a reagent in a method, such as affinity-based separation or magnetic-based separation, to enrich, isolate or substantially purify preparations of definitive endoderm cells which bind to the reagent.

Other embodiments of the invention described herein relate to compositions, such as cell cultures, which comprise pluripotent cells and definitive endoderm cells. In certain embodiments, the cell cultures comprise both stem cells and definitive endoderm cells. The number of stem cells present in such cultures can be greater than, equal to or less than the number of definitive endoderm cells in the culture. In some embodiments, the stem cells are human embryonic stem cells. In certain embodiments the hESCs are maintained on a feeder layer. In such embodiments, the feeder layer cells can be cells, such as fibroblasts, which are obtained from humans, mice or any other suitable organism.

In some embodiments of the present invention, the compositions comprising definitive endoderm cells and hESCs also includes one or more growth factors. Such growth factors can include growth factors from the TGFβ superfamily. In such embodiments, the one or more growth factors comprise the Nodal/Activin and/or the BMP subgroups of the TGFβ superfamily of growth factors. In some embodiments, the one or more growth factors are selected from the group consisting of Nodal, Activin A, Activin B, BMP4, Wnt3a or combinations of any of these growth factors.

Other embodiments of the present inventions are described with reference to the numbered paragraphs below:

1. A cell culture comprising human cells wherein at least about 10% of said human cells are definitive endoderm cells, said definitive endoderm cells being multipotent cells that can differentiate into cells of the gut tube or organs derived therefrom.

2. The cell culture of paragraph 1, wherein at least about 50% of said human cells are definitive endoderm cells.

3. The cell culture of paragraph 1, wherein at least about 80% of said human cells are definitive endoderm cells.

4. The cell culture of paragraph 1, wherein said definitive endoderm cells express a marker selected from the group consisting of SOX17 and CXCR4.

5. The cell culture of paragraph 4, wherein the expression of a marker selected from the group consisting of SOX17 and CXCR4 is greater than the expression of a marker selected from the group consisting of OCT4, alpha-fetoprotein (AFP), Thrombomodulin (TM), SPARC and SOX7 in said definitive endoderm cells.

6. The cell culture of paragraph 4, wherein said definitive endoderm cells do not express a marker selected from the group consisting of OCT4, AFP, TM, SPARC and SOX7.

7. The cell culture of paragraph 4, wherein said definitive endoderm cells express a marker selected from the group consisting of MIXL1, GATA4 and HNF3b.

8. The cell culture of paragraph 4, wherein said definitive endoderm cells express a marker selected from the group consisting of FGF17, VWF, CALCR, FOXQ1, CMKOR1 and CRIP1.

9. The cell culture of paragraph 1, wherein said definitive endoderm cells express SOX17 and CXCR4.

10. The cell culture of paragraph 9, wherein the expression of SOX17 and CXCR4 is greater than the expression of OCT4, AFP, TM, SPARC and SOX7 in said definitive endoderm cells.

11. The cell culture of paragraph 9, wherein said definitive endoderm cells do not express OCT4, AFP, TM, SPARC and SOX7.

12. The cell culture of paragraph 9, wherein said definitive endoderm cells express MIXL1, GATA4 and HNF3b.

13. The cell culture of paragraph 9, wherein said definitive endoderm cells express a marker selected from the group consisting of FGF17, VWF, CALCR, FOXQ1, CMKOR1 and CRIP1.

14. The cell culture of paragraph 1, wherein at least about 2 definitive endoderm cells are present for about every 1 pluripotent cell in said cell culture.

15. The cell culture of paragraph 14, wherein said pluripotent cell comprises an embryonic stem cell.

16. The cell culture of paragraph 15, wherein said embryonic stem cell is derived from a tissue selected from the group consisting of the morula, the inner cell mass (ICM) of an embryo and the gonadal ridges of an embryo.

17. The cell culture of paragraph 1 further comprising a medium which comprises less than about 10% serum.

18. The cell culture of paragraph 1 further comprising a growth factor of the Nodal/Activin subgroup of the TGFβ superfamily.

19. The cell culture of paragraph 1, further comprising a growth factor selected from the group consisting of Nodal, Activin A, Activin B and combinations thereof.

20. A cell population comprising cells wherein at least about 90% of said cells are human definitive endoderm cells, said human definitive endoderm cells being multipotent cells that can differentiate into cells of the gut tube or organs derived therefrom.

21. The cell population of paragraph 20, wherein at least about 95% of said cells are human definitive endoderm cells.

22. The cell population of paragraph 20, wherein at least about 98% of said cells are human definitive endoderm cells.

23. The cell population of paragraph 20, wherein said human definitive endoderm cells express a marker selected from the group consisting of SOX17 and CXCR4.

24. The cell population of paragraph 23, wherein the expression of a marker selected from the group consisting of SOX17 and CXCR4 is greater than the expression of a marker selected from the group consisting of OCT4, AFP, TM, SPARC and SOX7 in said human definitive endoderm cells.

25. The cell population of paragraph 23, wherein said human definitive endoderm cells do not express a marker selected from the group consisting of OCT4, AFP, TM, SPARC and SOX7.

26. The cell population of paragraph 23, wherein said human definitive endoderm cells express a marker selected from the group consisting of MIXL1, GATA4 and HNF3b.

27. The cell population of paragraph 23, wherein said definitive endoderm cells express a marker selected from the group consisting of FGF17, VWF, CALCR, FOXQ1, CMKOR1 and CRIP1.

28. The cell population of paragraph 20, wherein said human definitive endoderm cells express SOX17 and CXCR4.

29. The cell population of paragraph 28, wherein the expression of SOX17 and CXCR4 is greater than the expression of OCT4, AFP, TM, SPARC and SOX7 in said human definitive endoderm cells.

30. The cell population of paragraph 28, wherein said human definitive endoderm cells do not express OCT4, AFP, TM, SPARC and SOX7.

31. The cell population of paragraph 28, wherein said human definitive endoderm cells express MIXL1, GATA4 and HNF3b.

32. The cell population of paragraph 28, wherein said definitive endoderm cells express a marker selected from the group consisting of FGF17, VWF, CALCR, FOXQ1, CMKOR1 and CRIP1.

33. The cell population of paragraph 20, wherein at least about 2 human definitive endoderm cells are present for about every 1 pluripotent cell in said cell population.

4. The cell population of paragraph 33, wherein said pluripotent cell comprises an embryonic stem cell.

35. The cell population of paragraph 34, wherein said embryonic stem cell is derived from a tissue selected from the morula, the ICM of an embryo and the gonadal ridges of an embryo.

36. A method of producing definitive endoderm cells, said method comprising the steps of:
obtaining a cell population comprising pluripotent human cells;
providing said cell population with at least one growth factor of the TGFβ superfamily in an amount sufficient to promote differentiation of said pluripotent cells to definitive endoderm cells, said definitive endoderm cells being multipotent cells that can differentiate into cells of the gut tube or organs derived therefrom; and
allowing sufficient time for definitive endoderm cells to form, wherein said sufficient time for definitive endoderm cells to form has been determined by detecting the presence of definitive endoderm cells in said cell population.

37. The method of paragraph 36, wherein at least about 10% of said pluripotent cells differentiate into definitive endoderm cells.

38. The method of paragraph 36, wherein at least about 50% of said pluripotent cells differentiate into definitive endoderm cells.

39. The method of paragraph 36, wherein at least about 70% of said pluripotent cells differentiate into definitive endoderm cells.

40. The method of paragraph 36, wherein at least about 80% of said pluripotent cells differentiate into definitive endoderm cells.

41. The method of paragraph 36, wherein detecting the presence of definitive endoderm cells in said cell population comprises detecting the expression of at least one marker selected from the group consisting of SOX17 and CXCR4 and at least one marker from the group consisting of OCT4, AFP, TM, SPARC and SOX7 in cells of said cell population, wherein the expression of a marker selected from the group consisting of SOX17 and CXCR4 is greater than the expression of a marker selected from the group consisting of OCT4, AFP, TM, SPARC and SOX7 in said definitive endoderm cells.

42. The method of paragraph 36, wherein detecting the presence of definitive endoderm cells in said cell population comprises detecting the expression of at least one marker selected from the group consisting of SOX17 and CXCR4 and at least one marker from the group consisting of AFP, TM, and SOX7 in cells of said cell population, wherein the expression of a marker selected from the group consisting of SOX17 and CXCR4 is greater than the expression of a marker selected from the group consisting of AFP, TM, and SOX7 in said definitive endoderm cells.

43. The method of paragraph 42, wherein the expression of at least one of said markers is determined by Q-PCR.

44. The method of paragraph 42, wherein the expression of at least one of said markers is determined by immunocytochemistry.

45. The method of paragraph 36, wherein detecting the presence of definitive endoderm cells in said cell population comprises detecting the expression of at least one marker selected from the group consisting of FGF17, VWF, CALCR, FOXQ1, CMKOR1 and CRIP1 and at least one marker from the group consisting of OCT4, AFP, TM, SPARC and SOX7 in cells of said cell population, wherein the expression of a marker selected from the group consisting of FGF17, VWF, CALCR, FOXQ1, CMKOR1 and CRIP1 is greater than the expression of a marker selected from the group consisting of OCT4, AFP, TM, SPARC and SOX7 in said definitive endoderm cells.

46. The method of paragraph 36, wherein said at least one growth factor is of the Nodal/Activin subgroup of the TGFβ superfamily.

47. The method of paragraph 46, wherein said at least one growth factor is selected from the group consisting of Nodal Activin A, Activin B and combinations thereof.

48. The method of paragraph 47, wherein said at least one growth factor is Nodal.

49. The method of paragraph 47, wherein said at least one growth factor is Activin A.

50. The method of paragraph 47, wherein said at least one growth factor is Activin B.

51. The method of paragraph 36, wherein a plurality of growth factors of the TGFβ superfamily is provided.

52. The method of paragraph 51, wherein said plurality of growth factors comprises Nodal Activin A and Activin B.

53. The method of paragraph 36, wherein said at least one growth factor is provided in a concentration of at least about 10 ng/ml.

54. The method of paragraph 36, wherein said at least one growth factor is provided in a concentration of at least about 100 ng/ml.

55. The method of paragraph 36, wherein said at least one growth factor is provided in a concentration of at least about 500 ng/ml.

56. The method of paragraph 36, wherein said at least one growth factor is provided in a concentration of at least about 1000 ng/ml.

57. The method of paragraph 36, wherein said at least one growth factor is provided in a concentration of at least about 5000 ng/ml.

58. The method of paragraph 36, wherein said cell population is grown in a medium comprising less than about 10% serum.

59. The method of paragraph 36, wherein said pluripotent cells comprise stem cells.

60. The method of paragraph 59, wherein said pluripotent cells comprise embryonic stem cells.

61. The method of paragraph 60, wherein said embryonic stem cells are derived from a tissue selected from the group consisting of the morula, the ICM of an embryo and the gonadal ridges of an embryo.

62. A definitive endoderm cell produced by the method of paragraph 36.

63. A method of producing a cell population enriched in definitive endoderm cells, said method comprising the steps of:

differentiating cells in a population of pluripotent human cells so as to produce definitive endoderm cells, said definitive endoderm cells being multipotent cells that can differentiate into cells of the gut tube or organs derived therefrom;

providing to said cell population a reagent which binds to a marker expressed in said definitive endoderm cells but which is not substantially expressed in other cell types present in said cell population; and separating said definitive endoderm cells bound to said reagent from said other cell types present in said cell population, thereby producing a cell population enriched in definitive endoderm cells.

64. The method of paragraph 63, wherein the differentiating step further comprises obtaining a cell population comprising pluripotent human cells, providing said cell population with at least one growth factor of the TGFβ superfamily in an amount sufficient to promote differentiation of said pluripotent cells to definitive endoderm cells, said definitive endoderm cells being multipotent cells that can differentiate into cells of the gut tube or organs derived therefrom, and allowing sufficient time for definitive endoderm cells to form, wherein said sufficient time for definitive endoderm cells to form has been determined by detecting the presence of definitive endoderm cells in said cell population.

65. The method of paragraph 63, wherein detecting comprises detecting the expression of at least one marker selected from the group consisting of SOX17 and CXCR4 and at least one marker from the group consisting of OCT4, AFP, TM, SPARC and SOX7 in cells of said cell population, wherein the expression of a marker selected from the group consisting of SOX17 and CXCR4 is greater than the expression of a marker selected from the group consisting of OCT4, AFP, TM, SPARC and SOX7 in said definitive endoderm cells.

66. The method of paragraph 63, wherein detecting comprises detecting the expression of at least one marker selected from the group consisting of SOX17 and CXCR4 and at least one marker from the group consisting of AFP, TM, and SOX7 in cells of said cell population, wherein the expression of a marker selected from the group consisting of SOX17 and CXCR4 is greater than the expression of a marker selected from the group consisting of AFP, TM, and SOX7 in said definitive endoderm cells.

67. The method of paragraph 63, wherein detecting comprises detecting the expression of at least one marker selected from the group consisting of FGF17, VWF, CALCR, FOXQ1, CMKOR1 and CRIP1 and at least one marker from the group consisting of OCT4, AFP, TM, SPARC and SOX7 in cells of said cell population, wherein the expression of a marker selected from the group consisting of FGF17, VWF, CALCR, FOXQ1, CMKOR1 and CRIP1 is greater than the expression of a marker selected from the group consisting of OCT4, AFP, TM, SPARC and SOX7 in said definitive endoderm cells.

68. The method of paragraph 63, wherein at least about 95% of said cells are definitive endoderm cells.

69. The method of paragraph 63, wherein at least about 98% of said cells are definitive endoderm cells.

70. The method of paragraph 63, wherein said marker is CXCR4.

71. The method of paragraph 63, wherein said reagent is an antibody

72. The method of paragraph 71, wherein said antibody has affinity for CXCR4.

73. An enriched population of definitive endoderm cells produced by the method of paragraph 63.

74. The cell culture of any one of paragraphs 4 or 9, wherein said definitive endoderm cells do not significantly express a marker selected from the group consisting of OCT4, AFP, TM, SPARC and SOX7.

75. The cell population of any one of paragraphs 23 or 28, wherein said definitive endoderm cells do not significantly express a marker selected from the group consisting of OCT4, AFP, TM, SPARC and SOX7.

It will be appreciated that the methods and compositions described above relate to cells cultured in vitro. However, the above-described in vitro differentiated cell compositions may be used for in vivo applications.

Additional embodiments of the present inventions may also be found in U.S. Provisional Patent Application No. 60/532,004, entitled DEFINITIVE ENDODERM, filed Dec. 23, 2003; U.S. Provisional Patent Application No. 60/586,566, entitled CHEMOKINE CELL SURFACE RECEPTOR FOR THE ISOLATION OF DEFINITIVE ENDODERM, filed Jul. 9, 2004; and U.S. Provisional Patent Application No. 60/587,942, entitled CHEMOKINE CELL SURFACE RECEPTOR FOR THE ISOLATION OF DEFINITIVE ENDODERM, filed Jul. 14, 2004, the disclosures of which are incorporated herein by reference in their entireties.

DETAILED DESCRIPTION

Figure 1:
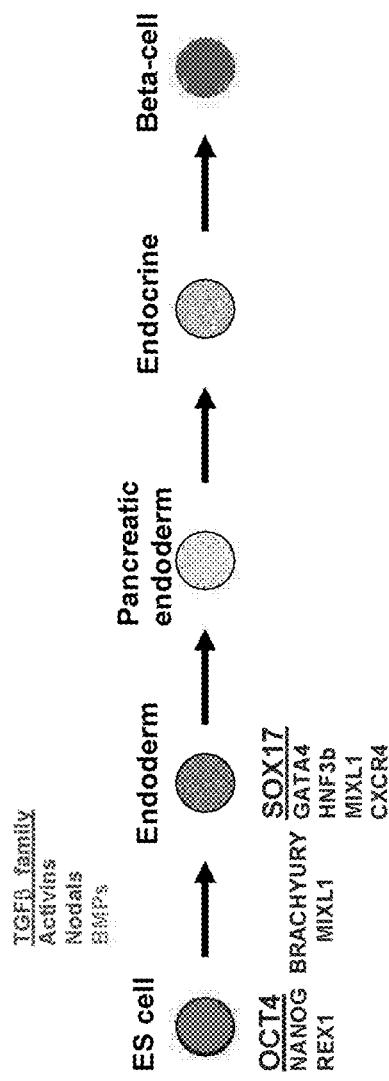
FIG. 1 is a schematic of a proposed differentiation pathway for the production of beta-cells from hESCs. The first step in the pathway commits the ES cell to the definitive endoderm lineage and represents one of the earliest known steps in the further differentiation of ES cells to pancreatic endoderm, endocrine endoderm, or islet/beta-cell. Some factors useful for mediating this transition are members of the TGFβ family which include, but are not limited to, activins, nodals and BMPs. Exemplary markers for defining the definitive endoderm target cell are SOX17, GATA4, HNF3b, MIX1 and CXCR4.

A crucial stage in early human development termed gastrulation occurs 2-3 weeks after fertilization. Gastrulation is extremely significant because it is at this time that the three primary germ layers are first specified and organized (Lu et al., 2001; Schoenwolf and Smith, 2000). The ectoderm is responsible for the eventual formation of the outer coverings of the body and the entire nervous system whereas the heart, blood, bone, skeletal muscle and other connective tissues are derived from the mesoderm. Definitive endoderm is defined as the germ layer that is responsible for formation of the entire gut tube which includes the esophagus, stomach and small and large intestines, and the organs which derive from the gut tube such as the lungs, liver, thymus, parathyroid and thyroid glands, gall bladder and pancreas (Grapin-Botton and Melton, 2000; Kimelman and Griffin, 2000; Tremblay et al., 2000; Wells and Melton, 1999; Wells and Melton, 2000). A very important distinction should be made between the definitive endoderm and the completely separate lineage of cells termed primitive endoderm. The primitive endoderm is primarily responsible for formation of extra-embryonic tissues, mainly the parietal and visceral endoderm portions of the placental yolk sac and the extracellular matrix material of Reichert's membrane.

During gastrulation, the process of definitive endoderm formation begins with a cellular migration event in which mesendoderm cells (cells competent to form mesoderm or endoderm) migrate through a structure called the primitive streak. Definitive endoderm is derived from cells, which migrate through the anterior portion of the streak and through the node (a specialized structure at the anterior most region of the streak). As migration occurs, definitive endoderm populates first the most anterior gut tube and culminates with the formation of the posterior end of the gut tube.

In vivo analyses of the formation of definitive endoderm, such as the studies in Zebrafish and *Xenopus* by Conlon et al., 1994; Feldman et al., 1998; Zhou et al., 1993; Aoki et al., 2002; Dougan et al., 2003; Tremblay et al., 2000; Vincent et al., 2003; Alexander et al., 1999; Alexander and Stainier, 1999; Kikuchi et al., 2001; Hudson et al., 1997 and in mouse by Kanai-Azuma et al., 2002 lay a foundation for how one might attempt to approach the development of a specific germ layer cell type in the culture dish using human embryonic stem cells. There are two aspects associated with in vitro ESC culture that pose major obstacles in the attempt to recapitulate development in the culture dish. First, organized germ layer or organ structures are not produced. The majority of germ layer and organ specific genetic markers will be expressed in a heterogeneous fashion in the differentiating hESC culture system. Therefore it is difficult to evaluate formation of a specific tissue or cell type due to this lack of organ specific boundaries. Almost all genes expressed in one cell type within a particular germ layer or tissue type are expressed in other cells of different germ layer or tissue types as well. Without specific boundaries there is considerably less means to assign gene expression specificity with a small sample of 1-3 genes. Therefore one must examine considerably more genes, some of which should be present as well as some that should not be expressed in the particular cell type of the organ or tissue of interest. Second, the timing of gene expression patterns is crucial to movement down a specific developmental pathway.

To further complicate matters, it should be noted that stem cell differentiation in vitro is rather asynchronous, likely considerably more so than in vivo. As such, one group of cells may be expressing genes associated with gastrulation, while another group may be starting final differentiation. Furthermore, manipulation of hESC monolayers or embryoid bodies (EBs) with or without exogenous factor application may result in profound differences with respect to overall gene expression pattern and state of differentiation. For these reasons, the application of exogenous factors must be timed according to gene expression patterns within a heterogeneous cell mixture in order to efficiently move the culture down a specific differentiation pathway. It is also beneficial to consider the morphological association of the cells in the culture vessel. The ability to uniformly influence hESCs when formed into so called embryoid bodies may be less optimal than hESCs grown and differentiated as monolayers and or hESC colonies in the culture vessel.

As an effective way to deal with the above-mentioned problems of heterogeneity and asynchrony, some embodiments of the present invention contemplate combining a method for differentiating cells with a method for the enrichment, isolation and/or purification of intermediate cell types in the differentiation pathway.

Embodiments of the present invention relate to novel, defined processes for the production of definitive endoderm cells in culture by differentiating pluripotent cells, such as stem cells into multipotent definitive endoderm cells. As used herein, "multipotent" or "multipotent cell" refers to a cell type that can give rise to a limited number of other particular cell types. As described above, definitive endoderm cells do not differentiate into tissues produced from ectoderm or mesoderm, but rather, differentiate into the gut tube as well as organs that are derived from the gut tube. In certain preferred embodiments, the definitive endoderm cells are derived from hESCs. Such processes can provide the basis for efficient production of human endodermal derived tissues such as pancreas, liver, lung, stomach, intestine and thyroid. For example, production of definitive endoderm may be the first step in differentiation of a stem cell to a functional insulin-producing β-cell. To obtain useful quantities of insulin-producing β-cells, high efficiency of differentiation is desirable for each of the differentiation steps that occur prior to reaching the pancreatic islet/β-cell fate. Since differentiation of stem cells to definitive endoderm cells represents perhaps the earliest step towards the production of functional pancreatic islet/β-cells (as shown in FIG. 1), high efficiency of differentiation at this step is particularly desirable.

In view of the desirability of efficient differentiation of pluripotent cells to definitive endoderm cells, some aspects of the present invention relate to in vitro methodology that results in approximately 50-80% conversion of pluripotent cells to definitive endoderm cells. Typically, such methods encompass the application of culture and growth factor conditions in a defined and temporally specified fashion. Further enrichment of the cell population for definitive endoderm cells can be achieved by isolation and/or purification of the definitive endoderm cells from other cells in the population by using a reagent that specifically binds to definitive endoderm cells. As such, aspects of the present invention relate to definitive endoderm cells as well as methods for producing and isolating and/or purifying such cells.

In order to determine the amount of definitive endoderm cells in a cell culture or cell population, a method of distinguishing this cell type from the other cells in the culture or in the population is desirable. Accordingly, certain embodiments of the present invention relate to cell markers whose presence, absence and/or relative expression levels are specific for definitive endoderm and methods for detecting and determining the expression of such markers. As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker. As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipd, a lipid, a lipoprotein or a small molecule.

In some embodiments of the present invention, the presence, absence and/or level of expression of a marker is determined by quantitative PCR (Q-PCR). For example, the amount of transcript produced by certain genetic markers, such as SOX17, CXCR4, OCT4, AFP, TM, SPARC, SOX7, MIXL1, GATA4, HNF3b, GSC, FGF17, VWF, CALCR, FOXQ1, CMKOR1, CRIP1 and other markers described herein is determined by quantitative Q-PCR. In other embodiments, immunohistochemistry is used to detect the proteins expressed by the above-mentioned genes. In still other embodiments, Q-PCR and immunohistochemical techniques are both used to identify and determine the amount or relative proportions of such markers.

By using methods, such as those described above, to determine the expression of one or more appropriate markers, it is possible to identify definitive endoderm cells, as well as determine the proportion of definitive endoderm cells in a cell culture or cell population. For example, in some embodiments of the present invention, the definitive endoderm cells or cell populations that are produced express the SOX17 and/or the CXCR4 gene at a level of about 2 orders of magnitude greater than non-definitive endoderm cell types or cell populations. In other embodiments, the definitive endoderm cells or cell populations that are produced express the SOX17 and/or the CXCR4 gene at a level of more than 2 orders of magnitude greater than non-definitive endoderm cell types or cell populations. In still other embodiments, the definitive endoderm cells or cell populations that are produced express one or more of the markers selected from the group consisting of SOX17, CXCR4, GSC, FGF17, VWF, CALCR, FOXQ1, CMKOR1 and CRIP1 at a level of about 2 or more than 2 orders of magnitude greater than non-definitive endoderm cell types or cell populations.

Further aspects of the present invention relate to cell cultures comprising definitive endoderm as well as cell populations enriched in definitive endoderm cells. As such, certain embodiments relate to cell cultures which comprise definitive endoderm cells, wherein at least about 50-80% of the cells in culture are definitive endoderm cells. A preferred embodiment relates to cells cultures comprising human cells, wherein at least about 50-80% of the human cells in culture are definitive endoderm cells. Because the efficiency of the differentiation procedure can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to definitive endoderm. In other embodiments of the present invention, conversion of a pluripotent cell population, such as a stem cell population, to substantially pure definitive endoderm cell population is contemplated.

The compositions and methods described herein have several useful features. For example, the cell cultures and cell populations comprising definitive endoderm as well as the methods for producing such cell cultures and cell populations are useful for modeling the early stages of human development. Furthermore, the compositions and methods described herein can also serve for therapeutic intervention in disease states, such as diabetes mellitus. For example, since definitive endoderm serves as the source for only a limited number of tissues, it can be used in the development of pure tissue or cell types.

Production of Definitive Endoderm from Pluripotent Cells

The definitive endoderm cell cultures and compositions comprising definitive endoderm cells that are described herein can be produced from pluripotent cells, such as embryonic stem cells. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. A preferred method for deriving definitive endoderm cells utilizes human embryonic stem cells (hESC) as the starting material for definitive endoderm production. The embryonic stem cells used in this method can be cells that originate from the morula, embryonic inner cell mass or those obtained from embryonic gonadal ridges. Human stem cells can be maintained in culture in a pluripotent state without substantial differentiation using methods that are known in the art. Such methods are described, for example, in U.S. Pat. Nos. 5,453,357, 5,670, 372, 5,690,926 5,843,780, 6,200,806 and 6,251,671 the disclosures of which are incorporated herein by reference in their entireties.

In some embodiments of the methods described herein, hESCs are maintained on a feeder layer. In such embodiments, any feeder layer which allows hESCs to be maintained in a pluripotent state can be used in the methods described herein. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative embodiments of the methods described herein permit the maintenance of pluripotent hESC without the use of a feeder layer. Such methods have been described in US Patent Application No. 2003/0175956, the disclosure of which is incorporated herein by reference in its entirety.

The human embryonic stem cells used herein can be maintained in culture either with or without serum. In some embodiments, serum replacement is used. In other embodiments, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into definitive endoderm. In some embodiments, differentiation to definitive endoderm is achieved by providing to the stem cell culture a growth factor of the TGFβ superfamily in an amount sufficient to promote differentiation to definitive endoderm. Growth factors of the TGFβ superfamily which are useful for the production of definitive endoderm are selected from the Nodal/Activin or BMP subgroups. In some embodiments of the differentiation methods described herein, the growth factor is selected from the group consisting of Nodal, Activin A, Activin B and BMP4. Additionally, the growth factor Wnt3a and other Wnt family members are useful for the production of definitive endoderm cells. In certain embodiments of the present invention, combinations of any of the above-mentioned growth factors can be used.

With respect to some of the embodiments of differentiation methods described herein, the above-mentioned growth factors are provided to the cells so that the growth factors are present in the cultures at concentrations sufficient to promote differentiation of at least a portion of the stem cells to definitive endoderm. In some embodiments of the present invention, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain embodiments of the present invention, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In a preferred embodiment, the growth factors are removed about four days after their addition.

Cultures of definitive endoderm cells can be grown in medium containing reduced serum or no serum. In certain embodiments of the present invention, serum concentrations can range from about 0.05% v/v to about 20% v/v. For example, in certain embodiments, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some embodiments, definitive endoderm cells are grown without serum. In other embodiments, definitive endoderm cells are grown with serum replacement. In still other embodiments, definitive endoderm cells are grown in the presence of B27. In such embodiments, the concentration of B27 supplement can range from about 0.2% v/v to about 20% v/v.

The progression of the hESC culture to definitive endoderm can be monitored by determining the expression of markers characteristic of definitive endoderm. In some embodiments, the expression of certain markers are determined by detecting the presence or absence of the marker. Alternatively, the expression of certain markers can determined by measuring the level at which the marker is present in the cells of the cell culture or cell population. In such embodiments, the measurement of marker expression can be qualitative or quantitative. One method of quantitating the expression markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest. In some embodiments of the present invention, the expression of marker genes characteristic of definitive endoderm as well as the lack of significant expression of marker genes characteristic of hESCs and other cell types is determined.

As described further in the Examples below, a reliable marker of definitive endoderm is the SOX17 gene. As such, the definitive endoderm cells produced by the methods described herein express the SOX17 marker gene, thereby producing the SOX17 gene product. Other markers of definitive endoderm are MIXL1, GATA4, HNF3b, GSC, FGF17, VWF, CALCR, FOXQ1, CMKOR1 and CRIP1. In some embodiments of the present invention, definitive endoderm cells express the SOX17 marker gene at a level higher than that of the SOX7 marker gene, which is characteristic of primitive and visceral endoderm (see Table 1). Additionally, in some embodiments, expression of the SOX17 marker gene is higher than the expression of the OCT4 marker gene, which is characteristic of hESCs. In other embodiments of the present invention, definitive endoderm cells express the SOX17 marker gene at a level higher than that of the AFP, SPARC or Thrombomodulin (TM) marker genes. In certain embodiments of the present invention, the SOX 17-expressing definitive endoderm cells produced by the methods described herein do not express significant levels or amounts of PDX1 (PDX1-negative).

Another marker of definitive endoderm is the CXCR4 gene. The CXCR4 gene encodes a cell surface chemokine receptor whose ligand is the chemoattractant SDF-1. The principal roles of the CXCR4 receptor-bearing cells in the adult are believed to be the migration of hematopoetic cells to the bone marrow, lymphocyte trafficking and the differentiation of various B cell and macrophage blood cell lineages [Kim, C., and Broxmeyer, H. J. Leukocyte Biol. 65, 6-15 (1999)]. The CXCR4 receptor also functions as a coreceptor for the entry of HIV-1 into T-cells [Feng, Y., et al. Science, 272, 872-877 (1996)]. In an extensive series of studies carried out by [McGrath, K. E. et al. Dev. Biology 213, 442-456 (1999)], the expression of the chemokine receptor CXCR4 and its unique ligand, SDF-1[Kim, C., and Broxmyer, H., J. Leukocyte Biol. 65, 6-15 (1999)], were delineated during early development and adult life in the mouse. The CXCR4/SDF1 interaction in development became apparent when it was demonstrated that if either gene was disrupted in transgenic mice [Nagasawa et al. Nature, 382, 635-638 (1996)], Ma, Q., et al Immunity, 10, 463-471 (1999)] it resulted in late embryonic lethality. McGrath et al. demonstrated that CXCR4 is the most abundant chemokine receptor messenger RNA detected during early gastrulating embryos (E7.5) using a combination of RNase protection and in situ hybridization methodologies. In the gastrulating embryo, CXCR4/SDF-1 signaling appears to be mainly involved in inducing migration of primitive-streak germlayer cells and is expressed on definitive endoderm, mesoderm and extraembryonic mesoderm present at this time. In E7.2-7.8 mouse embryos, CXCR4 and alpha-fetoprotein are mutually exclusive indicating a lack of expression in visceral endoderm [McGrath, K. E. et al. Dev. Biology 213, 442-456 (1999)].

In some embodiments of the present invention, the definitive endoderm cells produced by the methods described herein express the CXCR4 marker gene. In other embodiments, the definitive endoderm cells produced by the methods described herein express the CXCR4 marker gene as well as other markers of definitive endoderm including, but not limited to, SOX17, MIXL1, GATA4, HNF3b, GSC, FGF17, VWF, CALCR, FOXQ1, CMKOR1 and CRIP1. In some embodiments of the present invention, definitive endoderm cells express the CXCR4 marker gene at a level higher than that of the SOX7 marker gene. Additionally, in some embodiments, expression of the CXCR4 marker gene is higher than the expression of the OCT4 marker gene. In other embodiments of the present invention, definitive endoderm cells express the CXCR4 marker gene at a level higher than that of the AFP, SPARC or Thrombomodulin (TM) marker genes. In certain embodiments of the present invention, the CXCR4-expressing definitive endoderm cells produced by the methods described herein do not express significant levels or amounts of PDX1 (PDX1-negative).

It will be appreciated that expression of CXCR4 in endodermal cells does not preclude the expression of SOX17. Accordingly, in some embodiments of the present invention, definitive endoderm cells are those that express both the SOX17 and CXCR4 marker genes at a level higher than that of the SOX7 marker gene. Additionally, in some embodiments, the expression of both the SOX17 and CXCR4 marker genes is higher than the expression of the OCT4 marker gene. In other embodiments of the present invention, definitive endoderm cells express both the SOX17 and the CXCR4 marker genes at a level higher than that of the AFP, SPARC or Thrombomodulin (TM) marker genes. In certain embodiments of the present invention, the SOX17/CXCR4-expressing definitive endoderm cells produced by the methods described herein do not express significant levels or amounts of PDX1 (PDX1-negative).

It will be appreciated that SOX17 and/or CXCR4 marker expression is induced over a range of different levels in definitive endoderm cells depending on the differentiation conditions. As such, in some embodiments of the present invention, the expression of the SOX17 marker and/or the CXCR4 marker in definitive endoderm cells or cell populations is at least about 2-fold higher to at least about 10,000-fold higher than the expression of the SOX17 marker and/or the CXCR4 marker in non-definitive endoderm cells or cell populations, for example pluripotent stem cells. In other embodiments of the present invention, the expression of the SOX17 marker and/or the CXCR4 marker in definitive endoderm cells or cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10.000-fold higher than the expression of the SOX17 marker and/or the CXCR4 marker in non-definitive endoderm cells or cell populations, for example pluripotent stem cells. In some embodiments, the expression of the SOX17 marker and/or CXCR4 marker in definitive endoderm cells or cell populations is infinitely higher than the expression of the SOX17 marker and/or the CXCR4 marker in non-definitive endoderm cells or cell populations, for example pluripotent stem cells.

It will be appreciated that in some embodiments of the present invention, the expression of markers selected from the group consisting of GATA4, MIXL1, HNF3b, GSC, FGF17, VWF, CALCR, FOXQ1, CMKOR1 and CRIP1 in definitive endoderm cells or cell populations is increased as compared to the expression of GATA4, MIXL1, HNF3b, GSC, FGF17, VWF, CALCR, FOXQ1, CMKOR1 and CRIP1 in non-definitive endoderm cells or cell populations.

It will also be appreciated that there is a range of differences between the expression level of the SOX17 marker and the expression levels of the OCT4, SPARC, AFP, TM and/or SOX7 markers in definitive endoderm cells. Similarly, there exists a range of differences between the expression level of the CXCR4 marker and the expression levels of the OCT4, SPARC, AFP, TM and/or SOX7 markers in definitive endoderm cells. As such, in some embodiments of the present invention, the expression of the SOX17 marker or the CXCR4 marker is at least about 2-fold higher to at least about 10.000-fold higher than the expression of OCT4, SPARC, AFP, TM and/or SOX7 markers. In other embodiments of the present invention, the expression of the SOX17 marker or the CXCR4 marker is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10.000-fold higher than the expression of OCT4, SPARC, AFP, TM and/or SOX7 markers. In some embodiments, OCT4, SPARC, AFP, TM and/or SOX7 markers are not significantly expressed in definitive endoderm cells.

It will be appreciated that in some embodiments of the present invention, the expression of markers selected from the group consisting of GATA4, MIXL1, HNF3b, GSC, FGF17, VWF, CALCR, FOXQ1, CMKOR1 and CRIP1 in definitive endoderm cells is increased as compared to the expression of OCT4, SPARC, AFP, TM and/or SOX7 in definitive endoderm cells.

Compositions Comprising Definitive Endoderm

Some aspects of the present invention relate to compositions, such as cell populations and cell cultures, that comprise both pluripotent cells, such as stem cells, and definitive endoderm cells. For example, using the methods described herein, compositions comprising mixtures of hESCs and definitive endoderm cells can be produced. In some embodiments, compositions comprising at least about 5 definitive endoderm cells for about every 95 pluripotent cells are produced. In other embodiments, compositions comprising at least about 95 definitive endoderm cells for about every 5 pluripotent cells are produced. Additionally, compositions comprising other ratios of definitive endoderm cells to pluripotent cells are contemplated. For example, compositions comprising at least about 1 definitive endoderm cell for about every 1,000,000 pluripotent cells, at least about 1 definitive endoderm cell for about every 100,000 pluripotent cells, at least about 1 definitive endoderm cell for about every 10,000 pluripotent cells, at least about 1 definitive endoderm cell for about every 1000 pluripotent cells, at least about 1 definitive endoderm cell for about every 500 pluripotent cells, at least about 1 definitive endoderm cell for about every 100 pluripotent cells, at least about 1 definitive endoderm cell for about every 10 pluripotent cells, at least about 1 definitive endoderm cell for about every 5 pluripotent cells, at least about 1 definitive endoderm cell for about every 2 pluripotent cells, at least about 2 definitive endoderm cells for about every 1 pluripotent cell, at least about 5 definitive endoderm cells for about every 1 pluripotent cell, at least about 10 definitive endoderm cells for about every 1 pluripotent cell, at least about 20 definitive endoderm cells for about every 1 pluripotent cell, at least about 50 definitive endoderm cells for about every 1 pluripotent cell, at least about 100 definitive endoderm cells for about every 1 pluripotent cell, at least about 1000 definitive endoderm cells for about every 1 pluripotent cell, at least about 10,000 definitive endoderm cells for about every 1 pluripotent cell, at least about 100,000 definitive endoderm cells for about every 1 pluripotent cell and at least about 1,000,000 definitive endoderm cells for about every 1 pluripotent cell are contemplated. In some embodiments of the present invention, the pluripotent cells are human pluripotent stem cells. In certain embodiments the stem cells are derived from a morula, the inner cell mass of an embryo or the gonadal ridges of an embryo. In certain other embodiments, the pluripotent cells are derived from the gondal or germ tissues of a multicellular structure that has developed past the embryonic stage.

Some aspects of the present invention relate to cell cultures or cell populations comprising from at least about 5% definitive endoderm cells to at least about 95% definitive endoderm cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 95% of the human cells are definitive endoderm cells. Other embodiments of the present invention relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are definitive endoderm cells.

Further embodiments of the present invention relate to compositions, such as cell cultures or cell populations, comprising human cells, such as human definitive endoderm cells, wherein the expression of either the SOX17 or the CXCR4 marker is greater than the expression of the OCT4, SPARC, alpha-fetoprotein (AFP), Thrombomodulin (TM) and/or SOX7 marker in at least about 5% of the human cells. In other embodiments, the expression of either the SOX17 or the CXCR4 marker is greater than the expression of the OCT4, SPARC, AFP, TM and/or SOX7 marker in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in greater than 95% of the human cells.

It will be appreciated that some embodiments of the present invention relate to compositions, such as cell cultures or cell populations, comprising human cells, such as human definitive endoderm cells, wherein the expression of one or more markers selected from the group consisting of GATA4, MIXL1, HNF3b, GSC, FGF17, VWF, CALCR, FOXQ1, CMKOR1 and CRIP1 is greater than the expression of the OCT4, SPARC, AFP, TM and/or SOX7 markers in from at least about 5% to greater than at least about 95% of the human cells.

Still other embodiments of the present invention relate to compositions, such as cell cultures or cell populations, comprising human cells, such as human definitive endoderm cells, wherein the expression both the SOX17 and the CXCR4 marker is greater than the expression of the OCT4, SPARC, AFP, TM and/or SOX7 marker in at least about 5% of the human cells. In other embodiments, the expression of both the SOX17 and the CXCR4 marker is greater than the expression of the OCT4, SPARC, AFP, TM and/or SOX7 marker in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in greater than 95% of the human cells.

It will be appreciated that some embodiments of the present invention relate to compositions, such as cell cultures or cell populations, comprising human cells, such as human definitive endoderm cells, wherein the expression of the GATA4, MIXL1, HNF3b, GSC, FGF17, VWF, CALCR, FOXQ1, CMKOR1 and CRIP1 markers is greater than the expression of the OCT4, SPARC, AFP, TM and/or SOX7 markers in from at least about 5% to greater than at least about 95% of the human cells.

Additional embodiments of the present invention relate to compositions, such as cell cultures or cell populations, comprising mammalian endodermal cells, such as human endoderm cells, wherein the expression of either the SOX17 or the CXCR4 marker is greater than the expression of the OCT4, SPARC, AFP, TM and/or SOX7 marker in at least about 5% of the endodermal cells. In other embodiments, the expression of either the SOX17 or the CXCR4 marker is greater than the expression of the OCT4, SPARC, AFP, TM and/or SOX7 marker in at least about 10% of the endodermal cells, in at least about 15% of the endodermal cells, in at least about 20% of the endodermal cells, in at least about 25% of the endodermal cells, in at least about 30% of the endodermal cells, in at least about 35% of the endodermal cells, in at least about 40% of the endodermal cells, in at least about 45% of the endodermal cells, in at least about 50% of the endodermal cells, in at least about 55% of the endodermal cells, in at least about 60% of the endodermal cells, in at least about 65% of the endodermal cells, in at least about 70% of the endodermal cells, in at least about 75% of the endodermal cells, in at least about 80% of the endodermal cells, in at least about 85% of the endodermal cells, in at least about 90% of the endodermal cells, in at least about 95% of the endodermal cells or in greater than 95% of the endodermal cells.

It will be appreciated that some embodiments of the present invention relate to compositions, such as cell cultures or cell populations comprising mammalian endodermal cells, wherein the expression of one or more markers selected from the group consisting of GATA4, MIXL1, HNF3b, GSC, FGF17, VWF, CALCR, FOXQ1, CMKOR1 and CRIP1 is greater than the expression of the OCT4, SPARC, AFP, TM and/or SOX7 markers in from at least about 5% to greater than at least about 95% of the endodermal cells.

Still other embodiments of the present invention relate to compositions, such as cell cultures or cell populations, comprising mammalian endodermal cells, such as human endodermal cells, wherein the expression both the SOX17 and the CXCR4 marker is greater than the expression of the OCT4, SPARC, AFP, TM and/or SOX7 marker in at least about 5% of the endodermal cells. In other embodiments, the expression of both the SOX17 and the CXCR4 marker is greater than the expression of the OCT4, SPARC, AFP, TM and/or SOX7 marker in at least about 10% of the endodermal cells, in at least about 15% of the endodermal cells, in at least about 20% of the endodermal cells, in at least about 25% of the endodermal cells, in at least about 30% of the endodermal cells, in at least about 35% of the endodermal cells, in at least about 40% of the endodermal cells, in at least about 45% of the endodermal cells, in at least about 50% of the endodermal cells, in at least about 55% of the endodermal cells, in at least about 60% of the endodermal cells, in at least about 65% of the endodermal cells, in at least about 70% of the endodermal cells, in at least about 75% of the endodermal cells, in at least about 80% of the endodermal cells, in at least about 85% of the endodermal cells, in at least about 90% of the endodermal cells, in at least about 95% of the endodermal cells or in greater than 95% of the endodermal cells.

It will be appreciated that some embodiments of the present invention relate to compositions, such as cell cultures or cell populations comprising mammalian endodermal cells, wherein the expression of the GATA4, MIXL1, HNF3b, GSC, FGF17, VWF, CALCR, FOXQ1, CMKOR1 and CRIP1 markers is greater than the expression of the OCT4, SPARC, AFP, TM and/or SOX7 markers in from at least about 5% to greater than at least about 95% of the endodermal cells.

Using the methods described herein, compositions comprising definitive endoderm cells substantially free of other cell types can be produced. With respect to cells in cell cultures or in cell populations, the term "substantially free of" means that the specified cell type of which the cell culture or cell population is free, is present in an amount of less than about 5% of the total number of cells present in the cell culture or cell population. In some embodiments of the present invention, the definitive endoderm cell populations or cell cultures produced by the methods described herein are substantially free of cells that significantly express the OCT4, SOX7, AFP, SPARC, TM, ZIC1 or BRACH marker genes.

In one embodiment of the present invention, a description of a definitive endoderm cell based on the expression of marker genes is, SOX17 high, MIXL1 high, AFP low, SPARC low, Thrombomodulin low, SOX7 low, CXCR4 high.

Enrichment, Isolation and/or Purification of Definitive Endoderm

With respect to additional aspects of the present invention, definitive endoderm cells can be enriched, isolated and/or purified by using an affinity tag that is specific for such cells. Examples of affinity tags specific for definitive endoderm cells are antibodies, ligands or other binding agents that are specific to a marker molecule, such as a polypeptide, that is present on the cell surface of definitive endoderm cells but which is not substantially present on other cell types that would be found in a cell culture produced by the methods described herein. In some embodiments, an antibody which binds to CXCR4 is used as an affinity tag for the enrichment, isolation or purification of definitive endoderm cells. In other embodiments, the chemokine SDF-1 or other molecules based on SDF-1 can also be used as affinity tags. Such molecules include, but not limited to, SDF-1 fragments, SDF-1 fusions or SDF-1 mimetics.

Methods for making antibodies and using them for cell isolation are known in the art and such methods can be implemented for use with the antibodies and cells described herein. In one embodiment, an antibody which binds to CXCR4 is attached to a magnetic bead then allowed to bind to definitive endoderm cells in a cell culture which has been enzymatically treated to reduce intercellular and substrate adhesion. The cell/antibody/bead complexes are then exposed to a movable magnetic field which is used to separate bead-bound definitive endoderm cells from unbound cells. Once the definitive endoderm cells are physically separated from other cells in culture, the antibody binding is disrupted and the cells are replated in appropriate tissue culture medium.

Embodiments of the present invention contemplate additional methods for obtaining enriched, isolated or purified definitive endoderm cell cultures or populations. For example, in some embodiments, the CXCR4 antibody is incubated with definitive endoderm-containing cell culture that has been treated to reduce intercellular and substrate adhesion. The cells are then washed, centrifuged and resuspended. The cell suspension is then incubated with a secondary antibody, such as an FITC-conjugated antibody that is capable of binding to the primary antibody. The cells are then washed, centrifuged and resuspended in buffer. The cell suspension is then analyzed and sorted using a fluorescence activated cell sorter (FACS). CXCR4-positive cells are collected separately from CXCR4-negative cells, thereby resulting in the isolation of such cell types. If desired, the isolated cell compositions can be further purified by using an alternate affinity-based method or by additional rounds of sorting using the same or different markers that are specific for definitive endoderm.

In other embodiments of the present invention, definitive endoderm is enriched, isolated and/or purified using a ligand or other molecule that binds to CXCR4. In some embodiments, the molecule is SDF-1 or a fragment, fusion or mimetic thereof.

In preferred embodiments, definitive endoderm cells are enriched, isolated and/or purified from other non-definitive endoderm cells after the stem cell cultures are induced to differentiate towards the definitive endoderm lineage. It will be appreciated that the above-described enrichment, isolation and purification procedures can be used with such cultures at any stage of differentiation.

In addition to the procedures just described, definitive endoderm cells may also be isolated by other techniques for cell isolation. Additionally, definitive endoderm cells may also be enriched or isolated by methods of serial subculture in growth conditions which promote the selective survival or selective expansion of said definitive endoderm cells.

Using the methods described herein, enriched, isolated and/or purified populations of definitive endoderm cells and or tissues can be produced in vitro from pluripotent cell cultures or cell populations, such as stem cell cultures or populations, which have undergone at least some differentiation. In some embodiments, the cells undergo random differentiation. In a preferred embodiment, however, the cells are directed to differentiate primarily into definitive endoderm. Some preferred enrichment, isolation and/or purification methods relate to the in vitro production of definitive endoderm from human embryonic stem cells. Using the methods described herein, cell populations or cell cultures can be enriched in definitive endoderm content by at least about 2- to about 1000-fold as compared to untreated cell populations or cell cultures. In some embodiments, definitive endoderm cells can be enriched by at least about 5- to about 500-fold as compared to untreated cell populations or cell cultures. In other embodiments, definitive endoderm cells can be enriched from at least about 10- to about 200-fold as compared to untreated cell populations or cell cultures. In still other embodiments, definitive endoderm cells can be enriched from at least about 20- to about 100-fold as compared to untreated cell populations or cell cultures. In yet other embodiments, definitive endoderm cells can be enriched from at least about 40- to about 80-fold as compared to untreated cell populations or cell cultures. In certain embodiments, definitive endoderm cells can be enriched from at least about 2- to about 20-fold as compared to untreated cell populations or cell cultures.

Having generally described this invention, a further understanding can be obtained by reference to certain specific examples which are provided herein for purposes of illustration only, and are not intended to be limiting.

EXAMPLES

Many of the examples below describe the use of pluripotent human cells. Methods of producing pluripotent human cells are well known in the art and have been described numerous scientific publications, including U.S. Pat. Nos. 5,453,357, 5,670,372, 5,690,926, 6,090,622, 6,200,806 and 6,251,671 as well as U.S. Patent Application Publication No. 2004/0229350, the disclosures of which are incorporated herein by reference in their entireties.

Example 1

Human ES cells

For our studies of endoderm development we employed human embryonic stem cells, which are pluripotent and can divide seemingly indefinitely in culture while maintaining a normal karyotype. ES cells were derived from the 5-day-old embryo inner cell mass using either immunological or mechanical methods for isolation. In particular, the human embryonic stem cell line hESCyt-25 was derived from a supernumerary frozen embryo from an in vitro fertilization cycle following informed consent by the patient. Upon thawing the hatched blastocyst was plated on mouse embryonic fibroblasts (MEF), in ES medium (DMEM, 20% FBS, non essential amino acids, beta-mercaptoethanol, ITS supplement). The embryo adhered to the culture dish and after approximately two weeks, regions of undifferentiated hESCs were transferred to new dishes with MEFs. Transfer was accomplished with mechanical cutting and a brief digestion with dispase, followed by mechanical removal of the cell clusters, washing and re-plating. Since derivation, hESCyt-25 has been serially passaged over 100 times. We employed the hESCyt-25 human embryonic stem cell line as our starting material for the production of definitive endoderm.

It will be appreciated by those of skill in the art that stem cells or other pluripotent cells can also be used as starting material for the differentiation procedures described herein. For example, cells obtained from embryonic gonadal ridges, which can be isolated by methods known in the art, can be used as pluripotent cellular starting material.

Example 2 hESCyt-25 Characterization

The human embryonic stem cell line, hESCyt-25 has maintained a normal morphology, karyotype, growth and self-renewal properties over 18 months in culture. This cell line displays strong immunoreactivity for the OCT4, SSEA-4 and TRA-1-60 antigens, all of which, are characteristic of undifferentiated hESCs and displays alkaline phosphatase activity as well as a morphology identical to other established hESC lines. Furthermore, the human stem cell line, hESCyt-25, also readily forms embryoid bodies (EBs) when cultured in suspension. As a demonstration of its pluripotent nature, hES-CyT-25 differentiates into various cell types that represent the three principal germ layers. Ectoderm production was demonstrated by Q-PCR for ZIC1 as well as immunocytochemistry (ICC) for nestin and more mature neuronal markers. Immunocytochemical staining for β-III tubulin was observed in clusters of elongated cells, characteristic of early neurons. Previously, we treated EBs in suspension with retinoic acid, to induce differentiation of pluripotent stem cells to visceral endoderm (VE), an extra-embryonic lineage. Treated cells expressed high levels of α-fetoprotein (AFP) and SOX7, two markers of VE, by 54 hours of treatment. Cells differentiated in monolayer expressed AFP in sporadic patches as demonstrated by immunocytochemical staining. As will be described below, the hESCyT-25 cell line was also capable of forming definitive endoderm, as validated by real-time quantitative polymerase chain reaction (Q-PCR) and immunocytochemistry for SOX17, in the absence of AFP expression. To demonstrate differentiation to mesoderm, differentiating EBs were analyzed for Brachyury gene expression at several time points. Brachyury expression increased progressively over the course of the experiment. In view of the foregoing, the hESCyT-25 line is pluripotent as shown by the ability to form cells representing the three germ layers.

Example 3

Production of SOX17 Antibody

A primary obstacle to the identification of definitive endoderm in hESC cultures is the lack of appropriate tools. We therefore undertook the production of an antibody raised against human SOX17 protein.

The marker SOX17 is expressed throughout the definitive endoderm as it forms during gastrulation and its expression is maintained in the gut tube (although levels of expression vary along the A-P axis) until around the onset of organogenesis. SOX17 is also expressed in a subset of extra-embryonic endoderm cells. No expression of this protein has been observed in mesoderm or ectoderm. It has now been discovered that SOX17 is an appropriate marker for the definitive endoderm lineage when used in conjunction with markers to exclude extra-embryonic lineages.

As described in detail herein, the SOX17 antibody was utilized to specifically examine effects of various treatments and differentiation procedures aimed at the production of SOX17 positive definitive endoderm cells. Other antibodies reactive to AFP, SPARC and Thrombomodulin were also employed to rule out the production of visceral and parietal endoderm (extra-embryonic endoderm).

Figure 2:
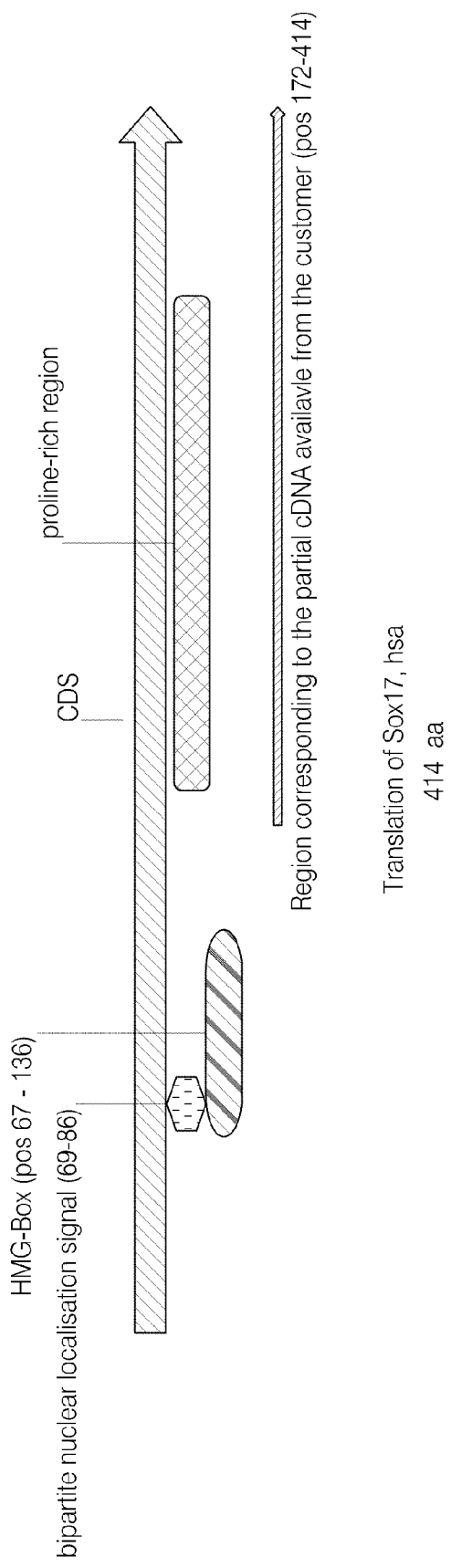
FIG. 2 is a diagram of the human SOX17 cDNA which displays the positions of conserved motifs and highlights the region used for the immunization procedure by GENOVAC.

In order to produce an antibody against SOX17, a portion of the human SOX17 cDNA (SEQ ID NO: 1) corresponding to amino acids 172-414 (SEQ ID NO: 2) in the carboxyterminal end of the SOX17 protein (FIG. 2) was used for genetic immunization in rats at the antibody production company, GENOVAC (Freiberg, Germany), according to procedures developed there. Procedures for genetic immunization can be found in U.S. Pat. Nos. 5,830,876, 5,817,637, 6,165,993 and 6,261,281 as well as International Patent Application Publication Nos. WO00/29442 and WO99/13915, the disclosures of which are incorporated herein by reference in their entireties.

Other suitable methods for genetic immunization are also described in the non-patent literature. For example, Barry et al. describe the production of monoclonal antibodies by genetic immunization in *Biotechniques* 16: 616-620, 1994, the disclosure of which is incorporated herein by reference in its entirety. Specific examples of genetic immunization methods to produce antibodies against specific proteins can be found, for example, in Costaglia et al., (1998) Genetic immunization against the human thyrotropin receptor causes thyroiditis and allows production of monoclonal antibodies recognizing the native receptor, *J. Immunol.* 160: 1458-1465; Kilpatrick et al (1998) Gene gun delivered DNA-based immunizations mediate rapid production of murine monoclonal antibodies to the Flt-3 receptor, *Hybridoma* 17: 569-576; Schmolke et al., (1998) Identification of hepatitis G virus particles in human serum by E2-specific monoclonal antibodies generated by DNA immunization, *J. Virol.* 72: 4541-4545; Krasemann et al., (1999) Generation of monoclonal antibodies against proteins with an unconventional nucleic acid-based immunization strategy, *J. Biotechnol.* 73: 119-129; and Ulivieri et al., (1996) Generation of a monoclonal antibody to a defined portion of the *Heliobacter pylori* vacuolating cytotoxin by DNA immunization, *J. Biotechnol.* 51: 191-194, the disclosures of which are incorporated herein by reference in their entireties.

Figure 3:
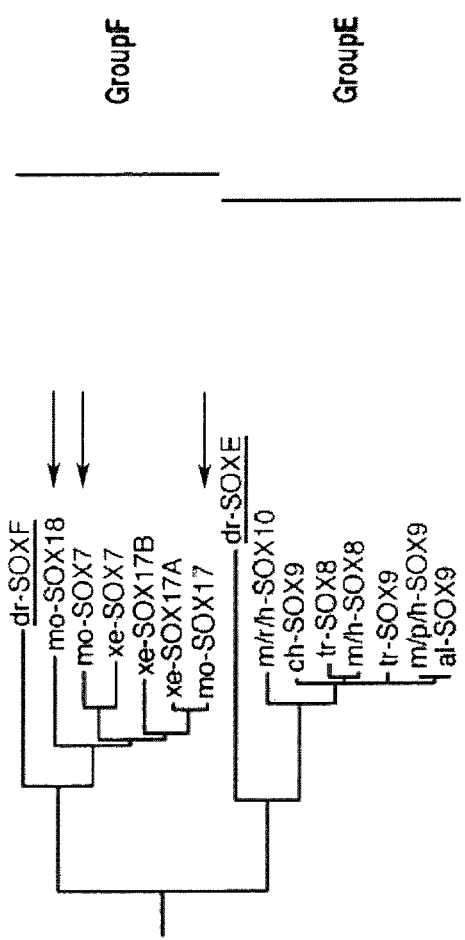
FIG. 3 is a relational dendrogram illustrating that SOX17 is most closely related to SOX7 and somewhat less to SOX18. The SOX17 proteins are more closely related among species homologs than to other members of the SOX group F subfamily within the same species.

SOX7 and SOX18 are the closest Sox family relatives to SOX17 as depicted in the relational dendrogram shown in FIG. 3. We employed the human SOX7 polypeptide as a negative control to demonstrate that the SOX17 antibody is specific for SOX17 and does not react with its closest family member. In particular, to demonstrate that the antibody produced by genetic immunization is specific for SOX17, SOX7 and other proteins were expressed in human fibroblasts, and then, analyzed for cross reactivity with the SOX17 antibody by Western blot and ICC. For example, the following methods were utilized for the production of the SOX17, SOX7 and EGFP expression vectors, their transfection into human fibroblasts and analysis by Western blot. Expression vectors employed for the production of SOX17, SOX7, and EGFP were pCMV6 (OriGene Technologies, Inc., Rockville, Md.), pCMV-SPORT6 (Invitrogen, Carlsbad, Calif.) and pEGFP-N1 (Clonetech, Palo Alto, Calif.), respectively. For protein production, telomerase immortalized MDX human fibroblasts were transiently transfected with supercoiled DNA in the presence of Lipofectamine 2000 (Invitrogen, Carlsbad, Calif.). Total cellular lysates were collected 36 hours posttransfection in 50 mM TRIS-HCl (pH 8), 150 mM NaCl, 0.1% SDS, 0.5% deoxycholate, containing a cocktail of protease inhibitors (Roche Diagnostics Corporation, Indianapolis, Ind.). Western blot analysis of 100 μg of cellular proteins, separated by SDS-PAGE on NuPAGE (4-12% gradient polyacrylamide, Invitrogen, Carlsbad, Calif.), and transferred by electro-blotting onto PDVF membranes (Hercules, Calif.), were probed with a 1/1000 dilution of the rat SOX17 antiserum in 10 mM TRIS-HCl (pH 8), 150 mM NaCl, 10% BSA, 0.05% Tween-20 (Sigma, St. Louis, Mo.), followed by Alkaline Phosphatase conjugated anti-rat IgG (Jackson ImmunoResearch Laboratories, West Grove, Pa.), and revealed through Vector Black Alkaline Phosphatase staining (Vector Laboratories, Burlingame, Calif.). The proteins size standard used was wide range color markers (Sigma, St. Louis, Mo.).

Figure 4:
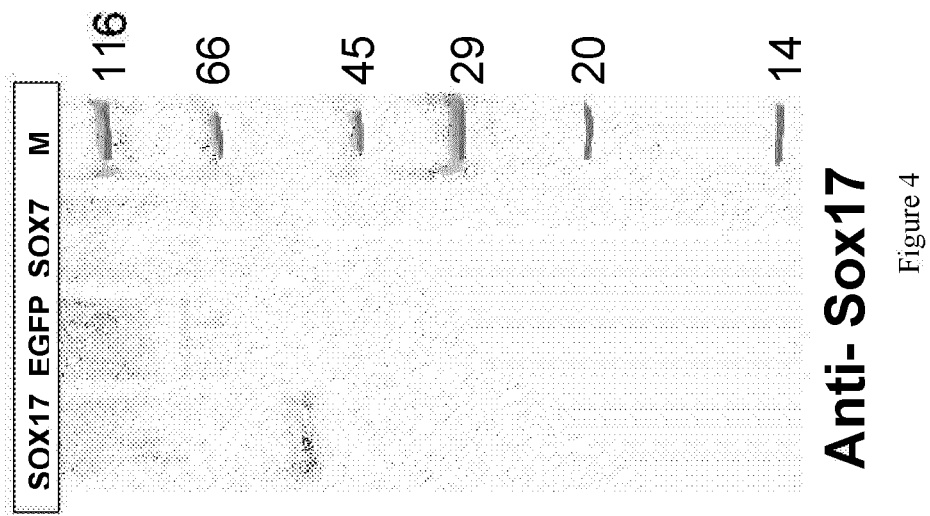
FIG. 4 is a Western blot probed with the rat anti-SOX17 antibody. This blot demonstrates the specificity of this antibody for human SOX17 protein over-expressed in fibroblasts (lane 1) and a lack of immunoreactivity with EGFP (lane 2) or the most closely related SOX family member, SOX7 (lane 3).

In FIG. 4, protein extracts made from human fibroblast cells that were transiently transfected with SOX17, SOX7 or EGFP cDNA's were probed on Western blots with the SOX17 antibody. Only the protein extract from hSOX17 transfected cells produced a band of ~51 Kda which closely matched the predicted 46 Kda molecular weight of the human SOX17 protein. There was no reactivity of the SOX17 antibody to extracts made from either human SOX7 or EGFP transfected cells. Furthermore, the SOX17 antibody clearly labeled the nuclei of human fibroblast cells transfected with the hSOX17 expression construct but did not label cells transfected with EGFP alone. As such, the SOX17 antibody exhibits specificity by ICC.

Example 4

Validation of SOX17 Antibody as a Marker of Definitive Endoderm

Figure 5:
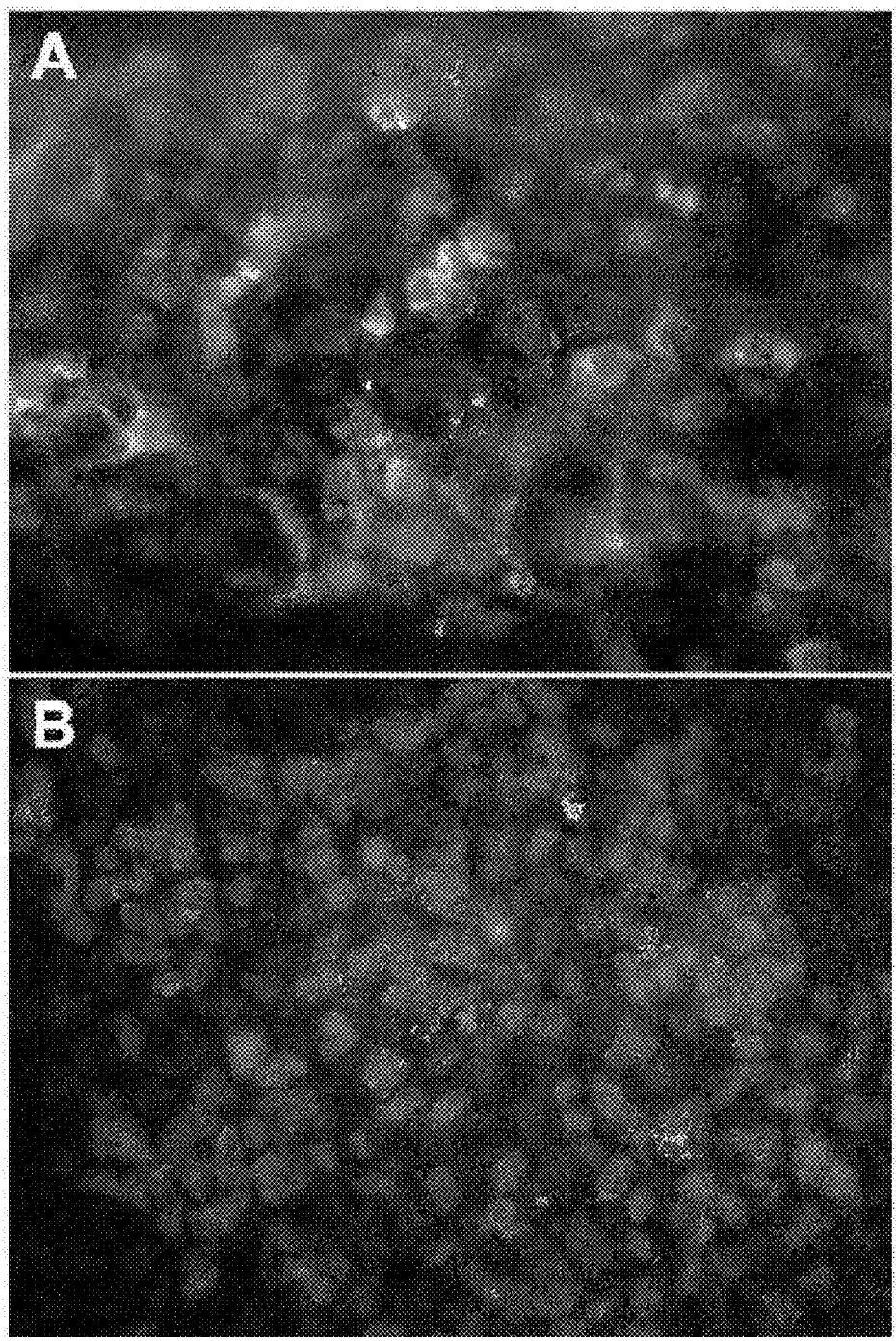
FIGS. 5A-B are micrographs showing a cluster of SOX17$^+$ cells that display a significant number of AFP$^+$ co-labeled cells (A). This is in striking contrast to other SOX17$^+$ clusters (B) where little or no AFP$^+$ cells are observed.
Figure 6:
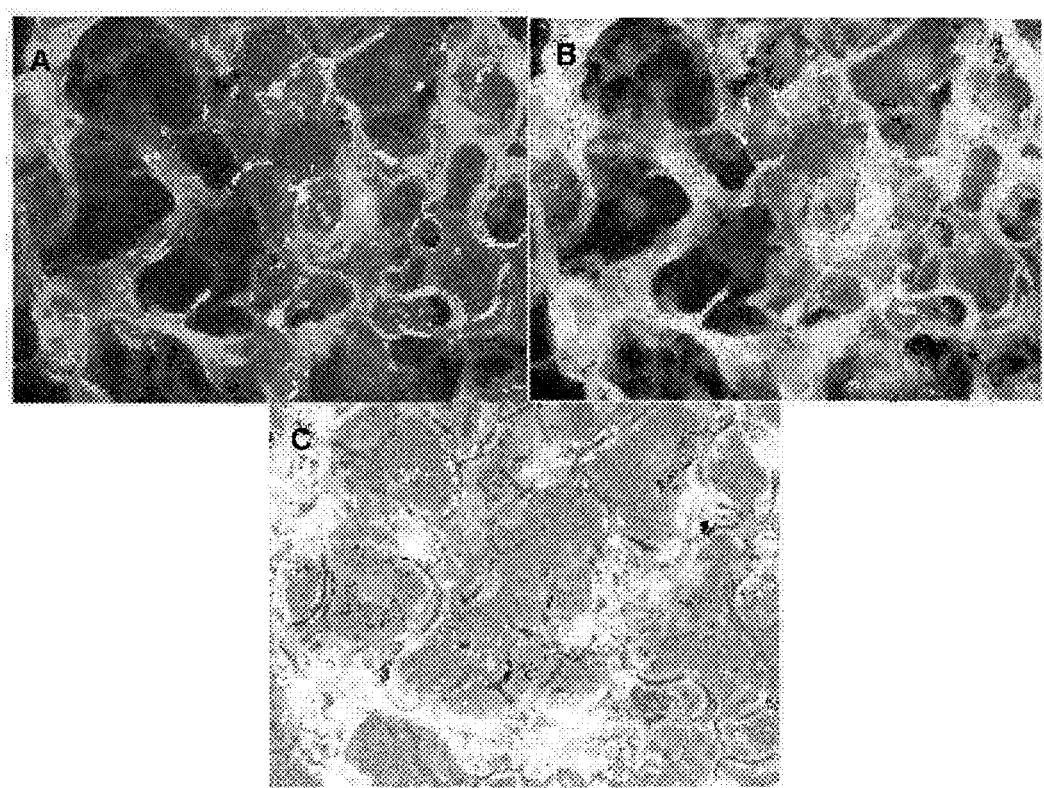
FIGS. 6A-C are micrographs showing parietal endoderm and SOX17. Panel A shows immunocytochemistry for human Thrombomodulin (TM) protein located on the cell surface of parietal endoderm cells in randomly differentiated cultures of hES cells. Panel B is the identical field shown in A double-labeled for TM and SOX17. Panel C is the phase contrast image of the same field with DAPI labeled nuclei. Note the complete correlation of DAPI labeled nuclei and SOX17 labeling.

As evidence that the SOX17 antibody is specific for human SOX17 protein and furthermore marks definitive endoderm, partially differentiated hESCs were co-labeled with SOX17 and AFP antibodies. It has been demonstrated that SOX17, SOX7, which is a closely related member of the SOX gene family subgroup F (FIG. 3), and AFP are each expressed in visceral endoderm. However, AFP and SOX7 are not expressed in definitive endoderm cells at levels detectable by ICC, and thus, they be can employed as negative markers for bonifide definitive endoderm cells. It was shown that SOX17 antibody labels populations of cells that exist as discrete groupings of cells or are intermingled with AFP positive cells. In particular, FIG. 5A shows that small numbers of SOX17 cells were co-labeled with AFP; however, regions were also found where there were little or no AFP+ cells in the field of SOX17+ cells (FIG. 5B). Similarly, since parietal endoderm has also been reported to express SOX17, antibody co-labeling with SOX17 together with the parietal markers SPARC and/or Thrombomodulin (TM) can be used to identify the SOX17+ cells which are parietal endoderm. As shown in FIGS. 6A-C, Thrombomodulin and SOX17 co-labelled parietal endoderm cells were produced by random differentiation of hES cells.

In view of the above cell labelling experiments, the identity of a definitive endoderm cell can be established by the marker profile SOX17$^{hi}$/AFP$^{lo}$/[TM$^{lo}$ or SPARC$^{lo}$]. In other words, the expression of the SOX17 marker is greater than the expression of the AFP marker, which is characteristic of visceral endoderm, and the TM or SPARC markers, which are characteristic of parietal endoderm. Accordingly, those cells positive for SOX17 but negative for AFP and negative for TM or SPARC are definitive endoderm.

Figure 7:
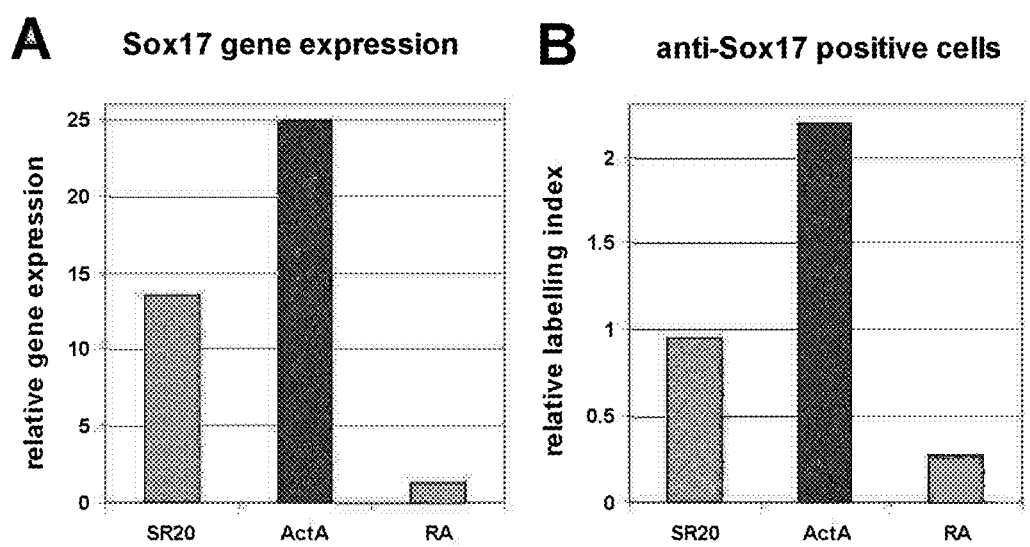
FIGS. 7A-B are bar charts showing SOX17 gene expression by quantitative PCR (Q-PCR) and anti-SOX17 positive cells by SOX17-specific antibody. Panel A shows that Activin A increases SOX17 gene expression while retinoic acid (RA) strongly suppresses SOX17 expression relative to the undifferentiated control media (SR20). Panel B shows the identical pattern as well as a similar magnitude of these changes is reflected in SOX17$^+$ cell number, indicating that Q-PCR measurement of SOX17 gene expression is very reflective of changes at the single cell level.
Figure 8:
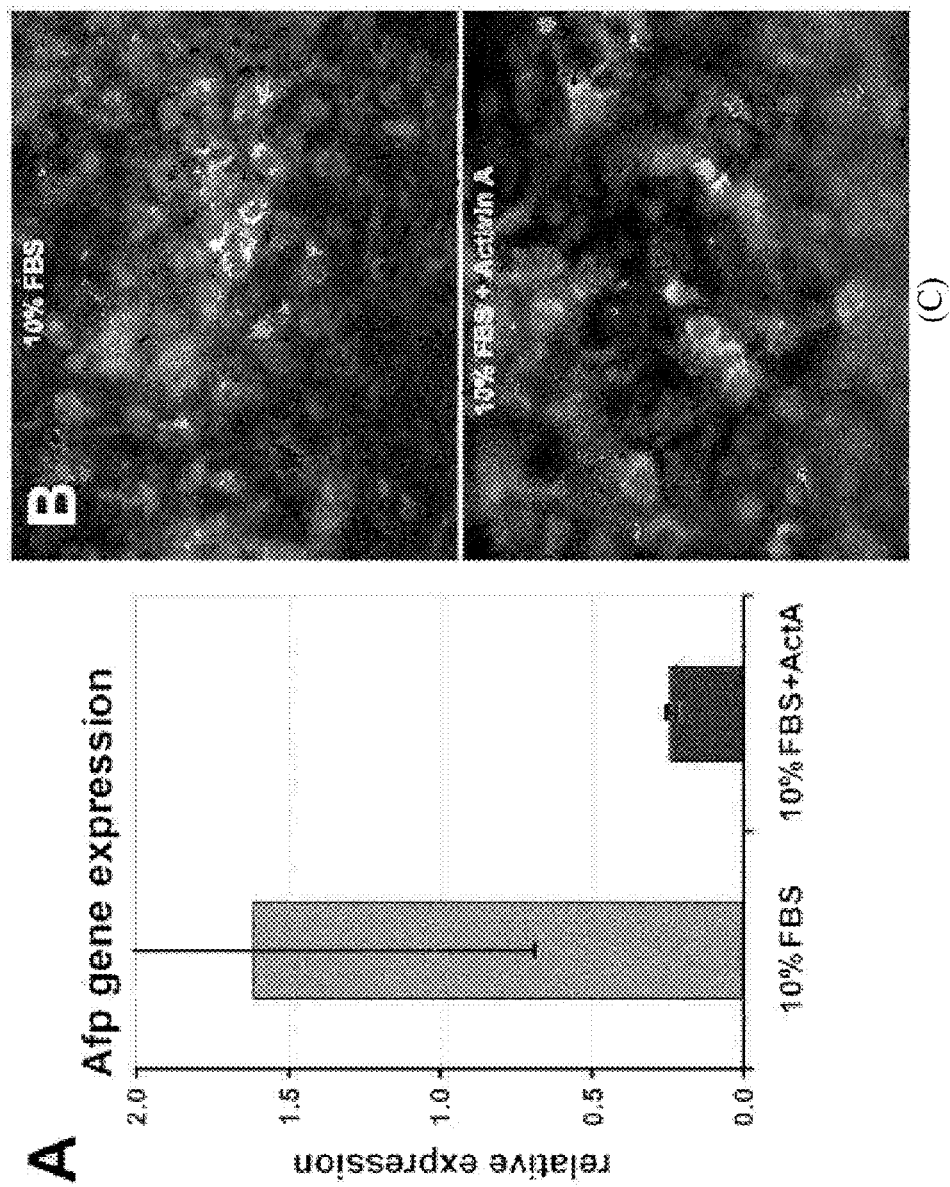
FIG. 8A is a bar chart which shows that a culture of differentiating hESCs in the presence of Activin A maintains a low level of AFP gene expression while cells allowed to randomly differentiate in 10% fetal bovine serum (FBS) exhibit a strong upregulation of AFP. The difference in expression levels is approximately 7-fold.
FIGS. 8B-C are images of two micrographs showing that the suppression of AFP expression by Activin A is also evident at the single cell level as indicated by the very rare and small clusters of AFP$^+$ cells observed in Activin A treatment conditions (bottom) relative to 10% FBS alone (top).
Figure 9:
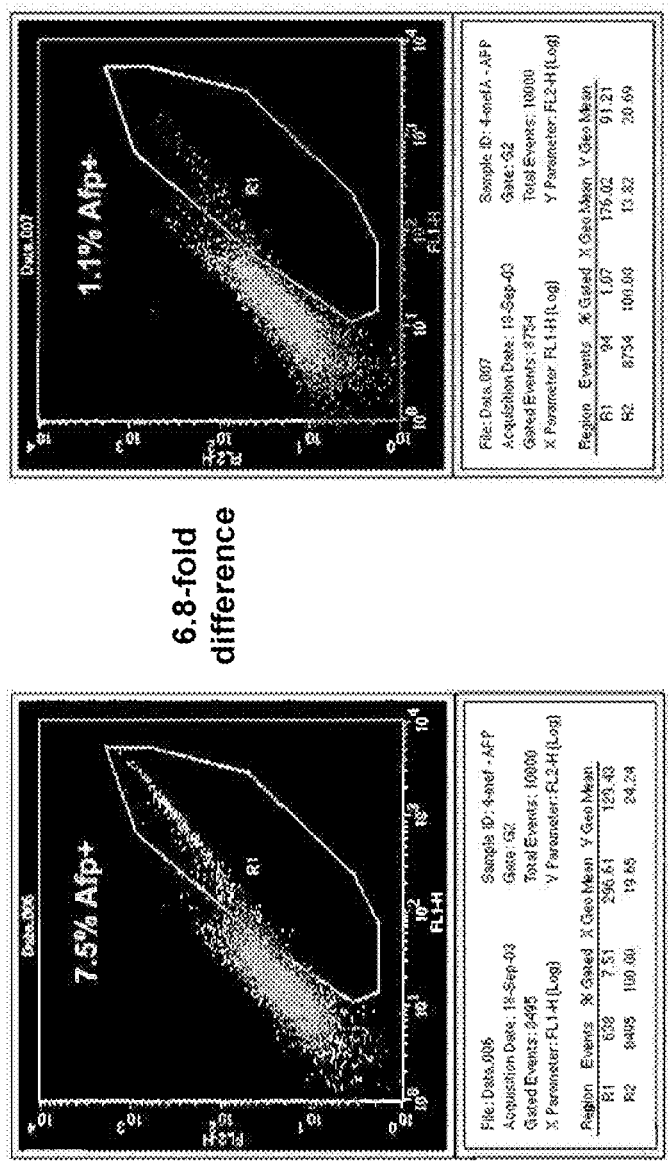
FIGS. 9A-B are comparative images showing the quantitation of the AFP$^+$ cell number using flow cytometry. This figure demonstrates that the magnitude of change in AFP gene expression (FIG. 8A) in the presence (right panel) and absence (left panel) of Activin A exactly corresponds to the number of AFP$^+$ cells, further supporting the utility of Q-PCR analyses to indicate changes occurring at the individual cell level.
Figure 10:
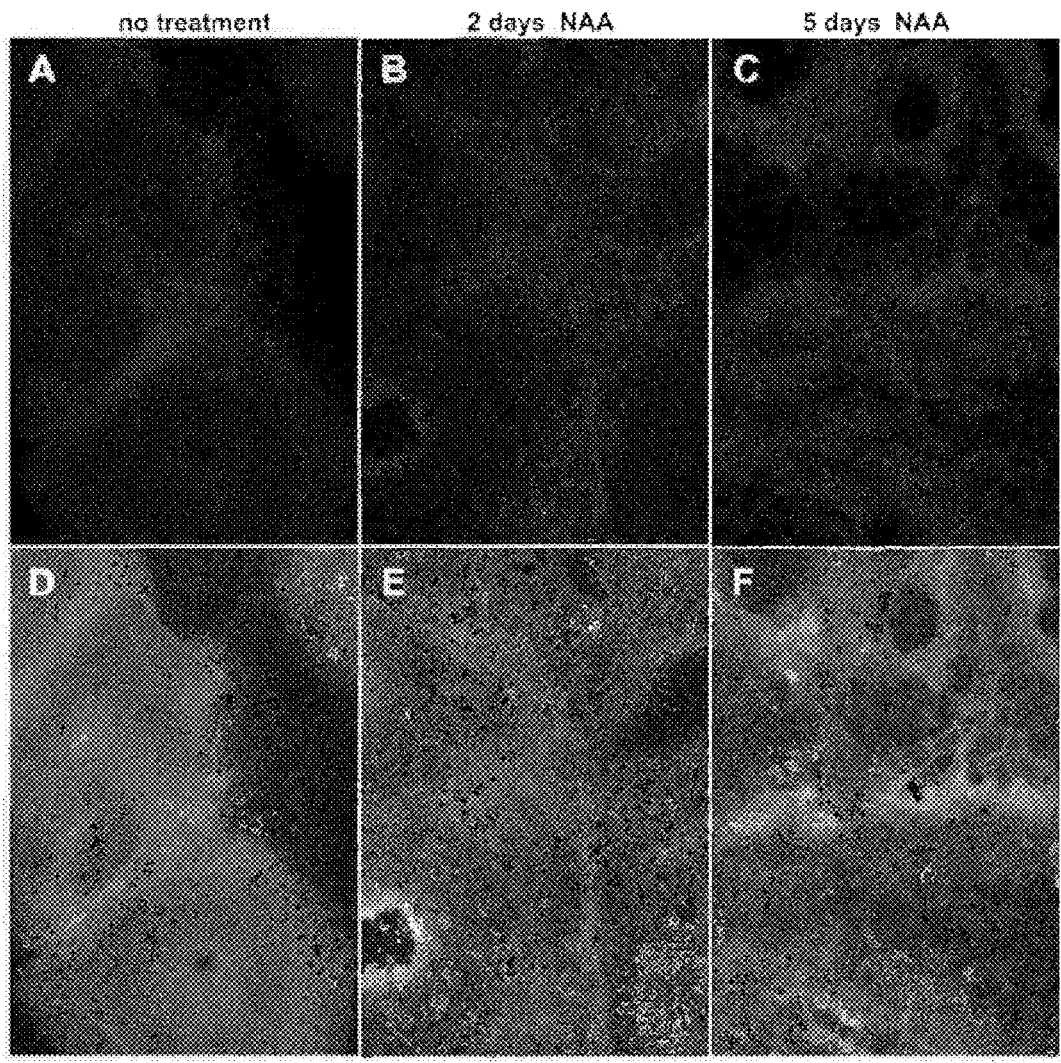
FIGS. 10A-F are micrographs which show that exposure of hESCs to nodal, Activin A and Activin B (NAA) yields a striking increase in the number of SOX17$^+$ cells over the period of 5 days (A-C). By comparing to the relative abundance of SOX17$^+$ cells to the total number of cells present in each field, as indicated by DAPI stained nuclei (D-F), it can be seen that approximately 30-50% of all cells are immunoreactive for SOX17 after five days treatment with NAA.
Figure 11:
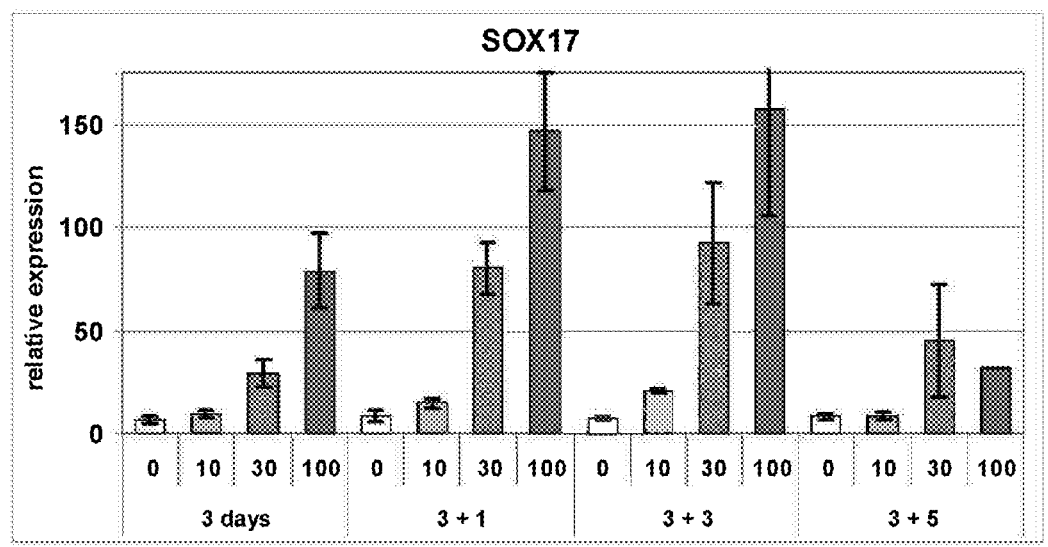
FIG. 11 is a bar chart which demonstrates that Activin A (0, 10, 30 or 100 ng/mL) dose-dependently increases SOX17 gene expression in differentiating hESCs. Increased expression is already robust after 3 days of treatment on adherent cultures and continues through subsequent 1, 3 and 5 days of suspension culture as well.
Figure 12:
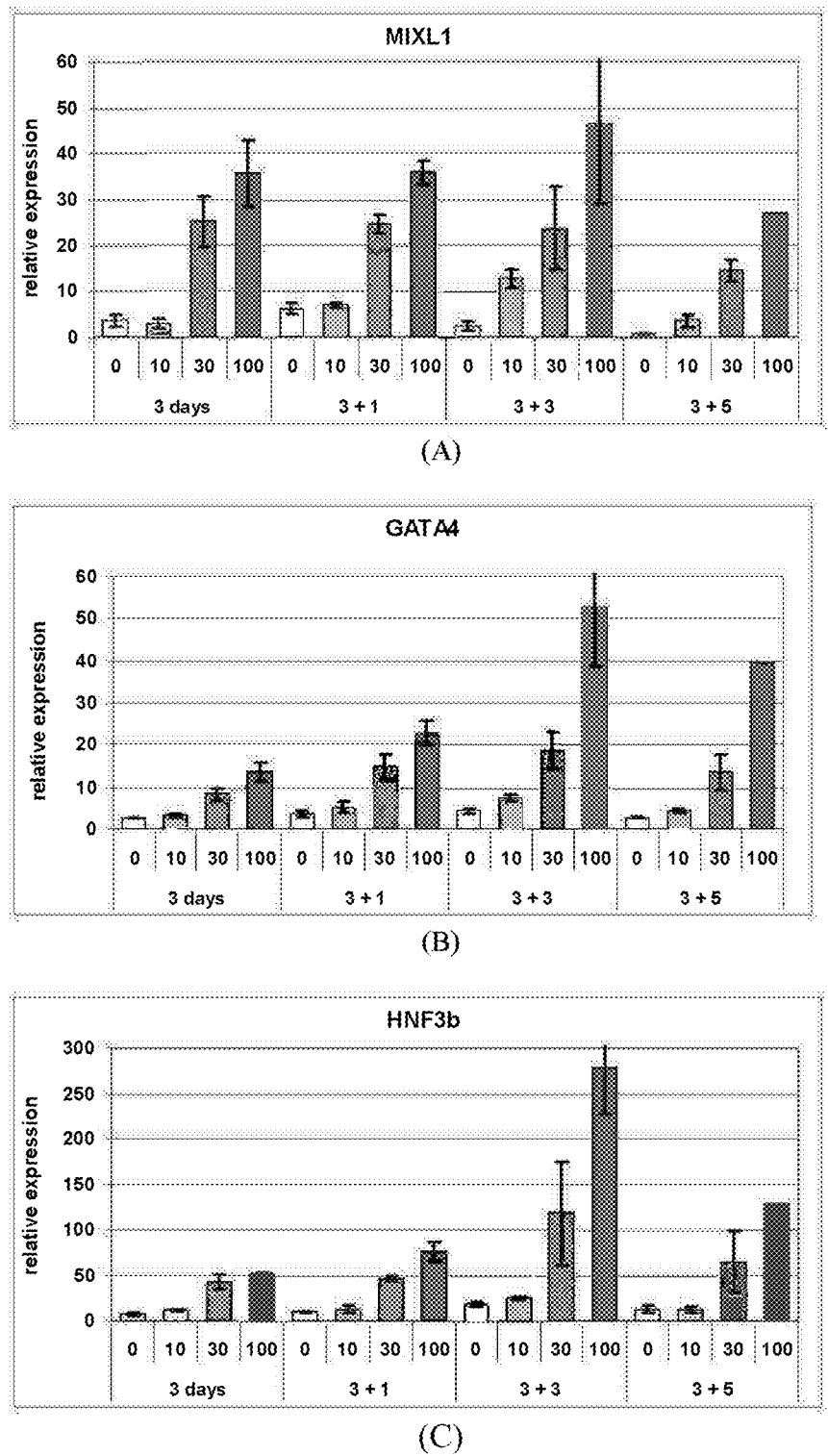
FIGS. 12A-C are bar charts which demonstrate the effect of Activin A on the expression of MIXL1 (panel A), GATA4 (panel B) and HNF3b (panel C). Activin A dose-dependent increases are also observed for three other markers of definitive endoderm; MIXL1, GATA4 and HNF3b. The magnitudes of increased expression in response to activin dose are strikingly similar to those observed for SOX17, strongly indicating that Activin A is specifying a population of cells that co-express all four genes (SOX17$^+$, MIXL1$^+$, GATA4$^+$ and HNF3b$^+$).
Figure 13:
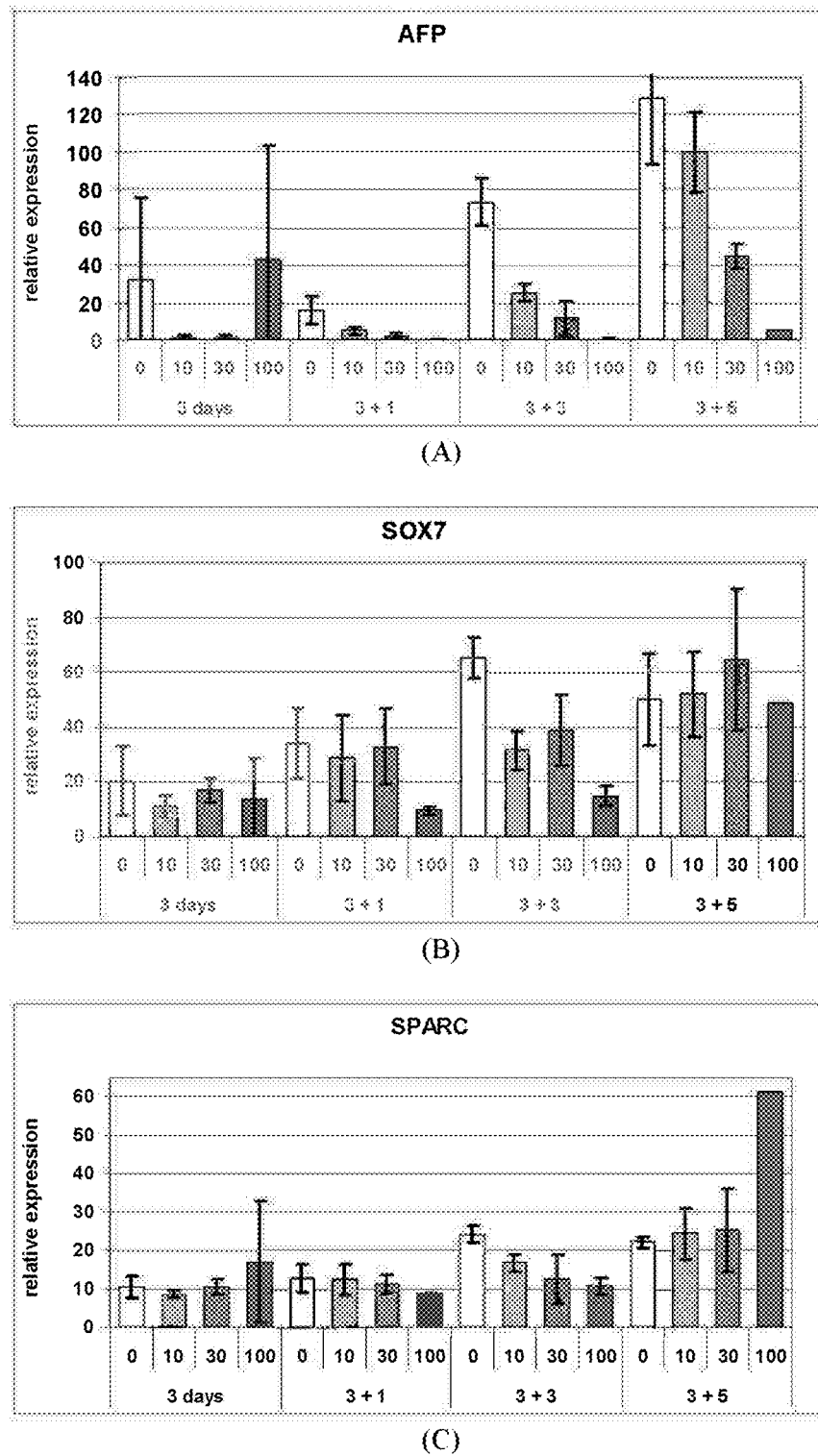
FIGS. 13A-C are bar charts which demonstrate the effect of Activin A on the expression of AFP (panel A), SOX7 (panel B) and SPARC (panel C). There is an Activin A dose-dependent decrease in expression of the visceral endoderm marker AFP. Markers of primitive endoderm (SOX7) and parietal endoderm (SPARC) remain either unchanged or exhibit suppression at some time points indicating that Activin A does not act to specify these extra-embryonic endoderm cell types. This further supports the fact that the increased expression of SOX17, MIXL1, GATA4, and HNF3b are due to an increase in the number of definitive endoderm cells in response to Activin A.
Figure 14:
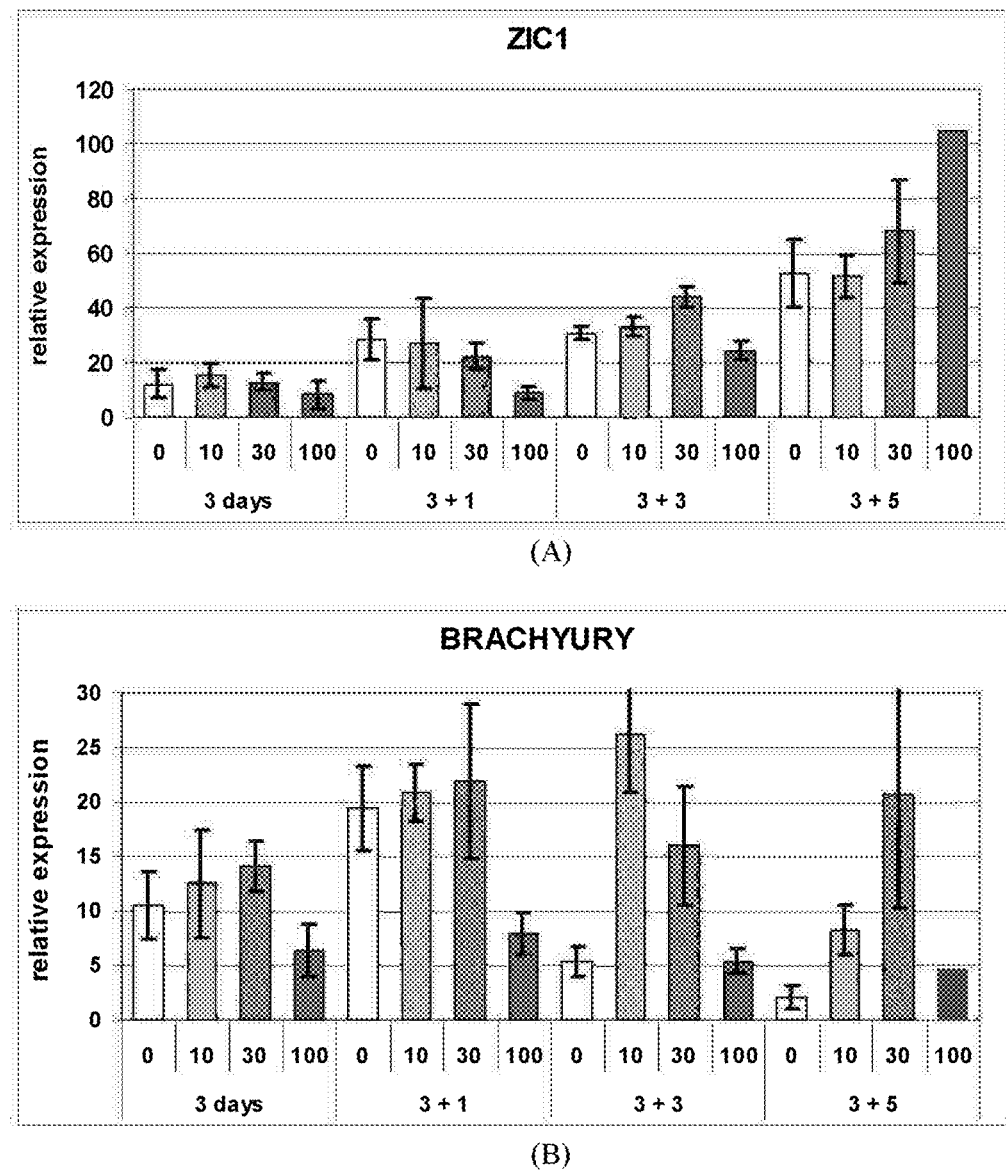
FIGS. 14A-B are bar charts showing the effect of Activin A on ZIC1 (panel A) and Brachyury expression (panel B) Consistent expression of the neural marker ZIC1 demonstrates that there is not a dose-dependent effect of Activin A on neural differentiation. There is a notable suppression of mesoderm differentiation mediated by 100 ng/mL of Activin A treatment as indicated by the decreased expression of brachyury. This is likely the result of the increased specification of definitive endoderm from the mesendoderm precursors. Lower levels of Activin A treatment (10 and 30 ng/mL) maintain the expression of brachyury at later time points of differentiation relative to untreated control cultures.

As a further evidence of the specificity of the SOX17$^{hi}$/AFP$^{lo}$/TM$^{lo}$/SPARC$^{lo}$ marker profile as predictive of definitive endoderm, SOX17 and AFP gene expression was quantitatively compared to the relative number of antibody labeled cells. As shown in FIG. 7A, hESCs treated with retinoic acid (visceral endoderm inducer), or Activin A (definitive endoderm inducer), resulted in a 10-fold difference in the level of SOX17 mRNA expression. This result mirrored the 10-fold difference in SOX17 antibody-labeled cell number (FIG. 7B). Furthermore, as shown in FIG. 8A, Activin A treatment of hESCs suppressed AFP gene expression by 6.8-fold in comparison to no treatment. This was visually reflected by a dramatic decrease in the number of AFP labeled cells in these cultures as shown in FIGS. 8B-C. To quantify this further, it was demonstrated that this approximately 7-fold decrease in AFP gene expression was the result of a similar 7-fold decrease in AFP antibody-labeled cell number as measured by flow cytometry (FIGS. 9A-B). This result is extremely significant in that it indicates that quantitative changes in gene expression as seen by Q-PCR mirror changes in cell type specification as observed by antibody staining.

Incubation of hESCs in the presence of Nodal family members (Nodal, Activin A and Activin B—NAA) resulted in a significant increase in SOX17 antibody-labeled cells over time. By 5 days of continuous activin treatment greater than 50% of the cells were labeled with SOX17 (FIGS. 10A-F). There were few or no cells labeled with AFP after 5 days of activin treatment.

In summary, the antibody produced against the carboxy-terminal 242 amino acids of the human SOX17 protein identified human SOX17 protein on Western blots but did not recognize SOX7, it's closest Sox family relative. The SOX17 antibody recognized a subset of cells in differentiating hESC cultures that were primarily SOX17+/AFP$^{lo/-}$ (greater than 95% of labeled cells) as well as a small percentage (<5%) of cells that co-label for SOX17 and AFP (visceral endoderm). Treatment of hESC cultures with activins resulted in a marked elevation of SOX17 gene expression as well as SOX17 labeled cells and dramatically suppressed the expression of AFP mRNA and the number of cells labeled with AFP antibody.

Example 5

Q-PCR Gene Expression Assay

In the following experiments, real-time quantitative RT-PCR (Q-PCR) was the primary assay used for screening the effects of various treatments on hESC differentiation. In particular, real-time measurements of gene expression were analyzed for multiple marker genes at multiple time points by Q-PCR. Marker genes characteristic of the desired as well as undesired cell types were evaluated to gain a better understanding of the overall dynamics of the cellular populations. The strength of Q-PCR analysis includes its extreme sensitivity and relative ease of developing the necessary markers, as the genome sequence is readily available. Furthermore, the extremely high sensitivity of Q-PCR permits detection of gene expression from a relatively small number of cells within a much larger population. In addition, the ability to detect very low levels of gene expression provides indications for "differentiation bias" within the population. The bias towards a particular differentiation pathway, prior to the overt differentiation of those cellular phenotypes, is unrecognizable using immunocytochemical techniques. For this reason, Q-PCR provides a method of analysis that is at least complementary and potentially much superior to immunocytochemical techniques for screening the success of differentiation treatments. Additionally, Q-PCR provides a mechanism by which to evaluate the success of a differentiation protocol in a quantitative format at semi-high throughput scales of analysis.

The approach taken here was to perform relative quantitation using SYBR Green chemistry on a Rotor Gene 3000 instrument (Corbett Research) and a two-step RT-PCR format. Such an approach allowed for the banking of cDNA samples for analysis of additional marker genes in the future, thus avoiding variability in the reverse transcription efficiency between samples.

Primers were designed to lie over exon-exon boundaries or span introns of at least 800 bp when possible, as this has been empirically determined to eliminate amplification from contaminating genomic DNA. When marker genes were employed that do not contain introns or they possess pseudogenes, DNase I treatment of RNA samples was performed.

We routinely used Q-PCR to measure the gene expression of multiple markers of target and non-target cell types in order to provide a broad profile description of gene expression in cell samples. The markers relevant for the early phases of hESC differentiation (specifically ectoderm, mesoderm, definitive endoderm and extra-embryonic endoderm) and for which validated primer sets are available are provided below in Table 1. The human specificity of these primer sets has also been demonstrated. This is an important fact since the hESCs were often grown on mouse feeder layers. Most typically, triplicate samples were taken for each condition and independently analyzed in duplicate to assess the biological variability associated with each quantitative determination. To generate PCR template, total RNA was isolated using RNeasy (Qiagen) and quantitated using RiboGreen (Molecular Probes). Reverse transcription from 350-500 ng of total RNA was carried out using the iScript reverse transcriptase kit (BioRad), which contains a mix of oligo-dT and random primers. Each 20 μL reaction was subsequently diluted up to 100 μL total volume and 3 μL was used in each 10 μL Q-PCR reaction containing 400 nM forward and reverse primers and 5 μL 2×SYBR Green master mix (Qiagen). Two step cycling parameters were used employing a 5 second denature at 85-94° C. (specifically selected according to the melting temp of the amplicon for each primer set) followed by a 45 second anneal/extend at 60° C. Fluorescence data was collected during the last 15 seconds of each extension phase. A three point, 10-fold dilution series was used to generate the standard curve for each run and cycle thresholds (Ct's) were converted to quantitative values based on this standard curve. The quantitated values for each sample were normalized to housekeeping gene performance and then average and standard deviations were calculated for triplicate samples. At the conclusion of PCR cycling, a melt curve analysis was performed to ascertain the specificity of the reaction. A single specific product was indicated by a single peak at the $T_m$ appropriate for that PCR amplicon. In addition, reactions performed without reverse transcriptase served as the negative control and do not amplify.

A first step in establishing the Q-PCR methodology was validation of appropriate housekeeping genes (HGs) in the experimental system. Since the HG was used to normalize across samples for the RNA input, RNA integrity and RT efficiency, it was of value that the HG exhibited a constant level of expression over time in all sample types in order for the normalization to be meaningful. We measured the expression levels of Cyclophilin G, hypoxanthine phosphoribosyltransferase 1 (HPRT), beta-2-microglobulin, hydroxymethylbiane synthase (HMBS), TATA-binding protein (TBP), and glucuronidase beta (GUS) in differentiating hESCs. Our results indicated that beta-2-microglobulin expression levels increased over the course of differentiation and therefore we excluded the use of this gene for normalization. The other genes exhibited consistent expression levels over time as well as across treatments. We routinely used both Cyclophilin G and GUS to calculate a normalization factor for all samples. The use of multiple HGs simultaneously reduces the variability inherent to the normalization process and increases the reliability of the relative gene expression values.

After obtaining genes for use in normalization, Q-PCR was then utilized to determine the relative gene expression levels of many marker genes across samples receiving different experimental treatments. The marker genes employed have been chosen because they exhibit enrichment in specific populations representative of the early germ layers and in particular have focused on sets of genes that are differentially expressed in definitive endoderm and extra-embryonic endoderm. These genes as well as their relative enrichment profiles are highlighted in Table 1.

TABLE 1

| Germ Layer | Gene | Expression Domains |
| --- | --- | --- |
| Endoderm | SOX17 | definitive, visceral and parietal endoderm |
|  | MIXL1 | endoderm and mesoderm |
|  | GATA4 | definitive and primitive endoderm |
|  | HNF3b | definitive endoderm and primitive endoderm, mesoderm, neural plate |
|  | GSC | endoderm and mesoderm |
| Extra-embryonic | SOX7 | visceral endoderm |
|  | AFP | visceral endoderm, liver |
|  | SPARC | parietal endoderm |
|  | TM | parietal endoderm/trophectoderm |
| Ectoderm | ZIC1 | neural tube, neural progenitors |
| Mesoderm | BRACH | nascent mesoderm |

Since many genes are expressed in more than one germ layer it is useful to quantitatively compare expression levels of many genes within the same experiment. SOX17 is expressed in definitive endoderm and to a smaller extent in visceral and parietal endoderm. SOX7 and AFP are expressed in visceral endoderm at this early developmental time point. SPARC and TM are expressed in parietal endoderm and Brachyury is expressed in early mesoderm.

Definitive endoderm cells were predicted to express high levels of SOX17 mRNA and low levels of AFP and SOX7 (visceral endoderm), SPARC (parietal endoderm) and Brachyury (mesoderm). In addition, ZIC1 was used here to further rule out induction of early ectoderm. Finally, GATA4 and HNF3b were expressed in both definitive and extra-embryonic endoderm, and thus, correlate with SOX17 expression in definitive endoderm (Table 1). A representative experiment is shown in FIGS. 11-14 which demonstrates how the marker genes described in Table 1 correlate with each other among the various samples, thus highlighting specific patterns of differentiation to definitive endoderm and extra-embryonic endoderm as well as to mesodermal and neural cell types.

In view of the above data it is clear that increasing doses of activin resulted in increasing SOX17 gene expression. Further this SOX17 expression predominantly represented definitive endoderm as opposed to extra-embryonic endoderm. This conclusion stems from the observation that SOX17 gene expression was inversely correlated with AFP, SOX7, and SPARC gene expression.

Example 6

Directed Differentiation of Human ES Cells to Definitive Endoderm

Human ES cell cultures will randomly differentiate if they are cultured under conditions that do not actively maintain their undifferentiated state. This heterogeneous differentiation results in production of extra-embryonic endoderm cells comprised of both parietal and visceral endoderm (AFP, SPARC and SOX7 expression) as well as early ectodermal and mesodermal derivatives as marked by ZIC1 and Nestin (ectoderm) and Brachyury (mesoderm) expression. Definitive endoderm cell appearance has not traditionally been examined or specified for lack of specific antibody markers in ES cell cultures. As such, and by default, early definitive endoderm production in ES cell cultures has not been well studied. Since no good antibody reagents for definitive endoderm cells have been available, most of the characterization has focused on ectoderm and extra-embryonic endoderm. Overall, there are significantly greater numbers of extra-embryonic and neurectodermal cell types in comparison to SOX17[hi] definitive endoderm cells in randomly differentiated ES cell cultures.

As undifferentiated hESC colonies expand on a bed of fibroblast feeders the edges of the colony take on alternative morphologies that are distinct from those cells residing within the interior of the colony. Many of these outer edge cells can be distinguished by their less uniform, larger cell body morphology and by the expression of higher levels of OCT4. It has been described that as ES cells begin to differentiate they alter the levels of OCT4 expression up or down relative to undifferentiated ES cells. Alteration of OCT4 levels above or below the undifferentiated threshold may signify the initial stages of differentiation away from the pluripotent state.

When undifferentiated colonies were examined by SOX17 immunocytochemistry, occasionally small 10-15-cell clusters of SOX17-positive cells were detected at random locations on the periphery and at the junctions between undifferentiated ESC colonies. As noted above, these scattered pockets of outer colony edges appeared to be some of the first cells to differentiate away from the classical ESC morphology as the colony expanded in size and became more crowded. Younger, smaller fully undifferentiated colonies (<1 mm; 4-5 days old) showed no SOX17 positive cells within or at the edges of the colonies while older, larger colonies (1-2 mm diameter, >5 days old) had sporadic isolated patches of SOX17 positive, AFP negative cells at the periphery of some colonies or in regions interior to the edge that were differentiated away from classical hESC morphology described previously. Given that this was the first development of an effective SOX17 antibody, definitive endoderm cells generated in such early "undifferentiated" ESC cultures have never been previously demonstrated.

Figure 15:
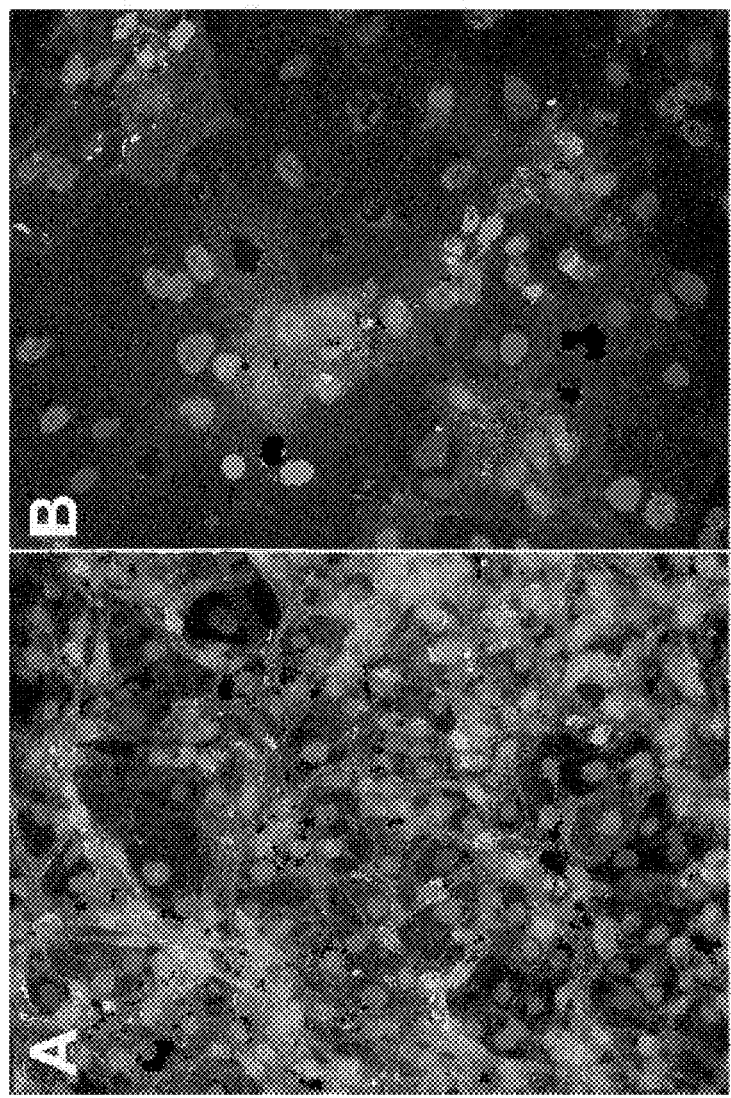
FIGS. 15A-B are micrographs showing decreased parietal endoderm differentiation in response to treatment with activins. Regions of TM$^{hi}$ parietal endoderm are found through the culture (A) when differentiated in serum alone, while differentiation to TM$^+$ cells is scarce when activins are included (B) and overall intensity of TM immunoreactivity is lower.
Figure 16:
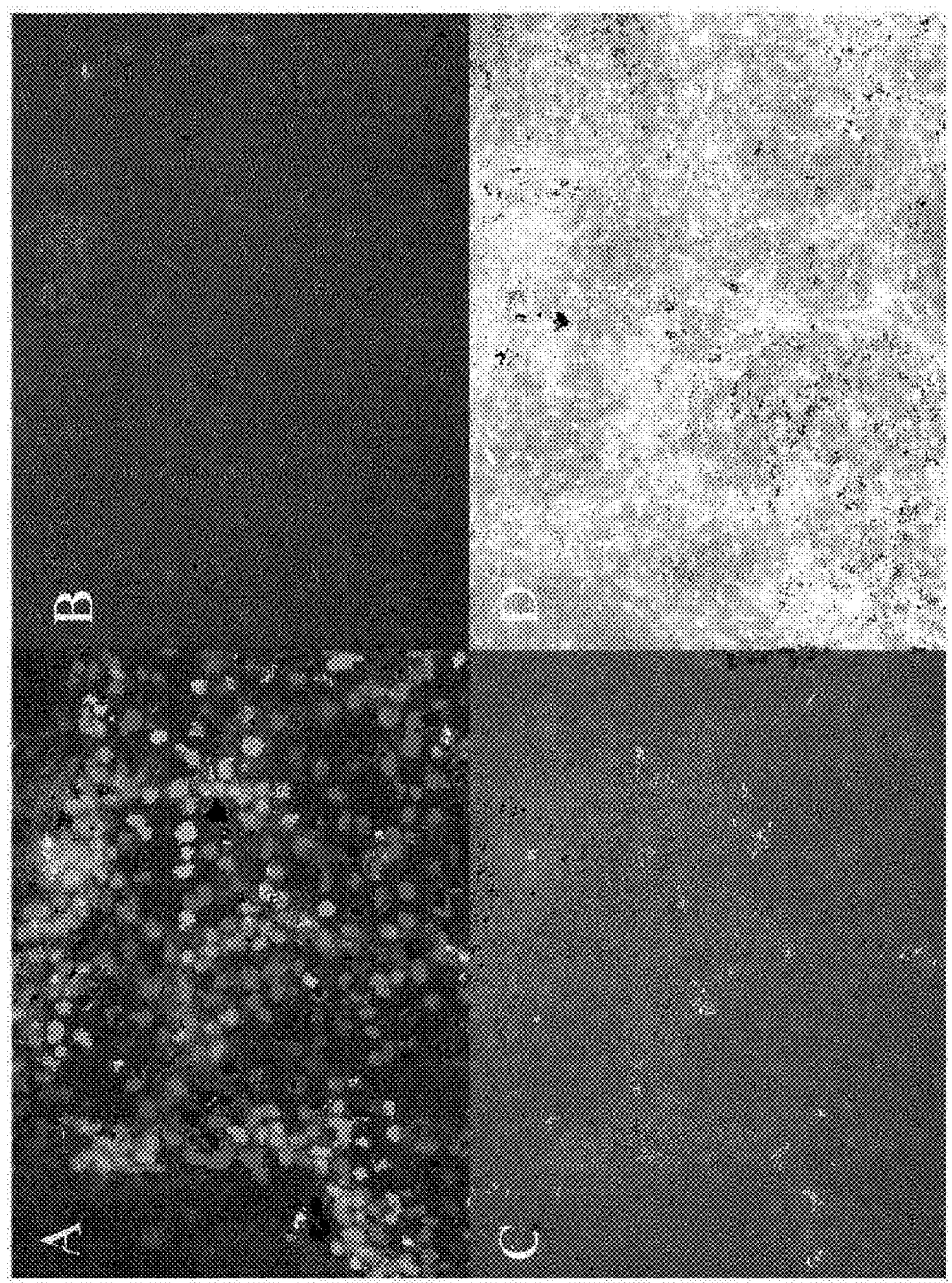
FIGS. 16A-D are micrographs which show marker expression in response to treatment with Activin A and Activin B. hESCs were treated for four consecutive days with Activin A and Activin B and triple labeled with SOX17, AFP and TM antibodies. Panel A—SOX17; Panel B—AFP; Panel C—TM; and Panel D—Phase/DAPI. Notice the numerous SOX17 positive cells (A) associated with the complete absence of AFP (B) and TM (C) immunoreactivity.
Figure 17:
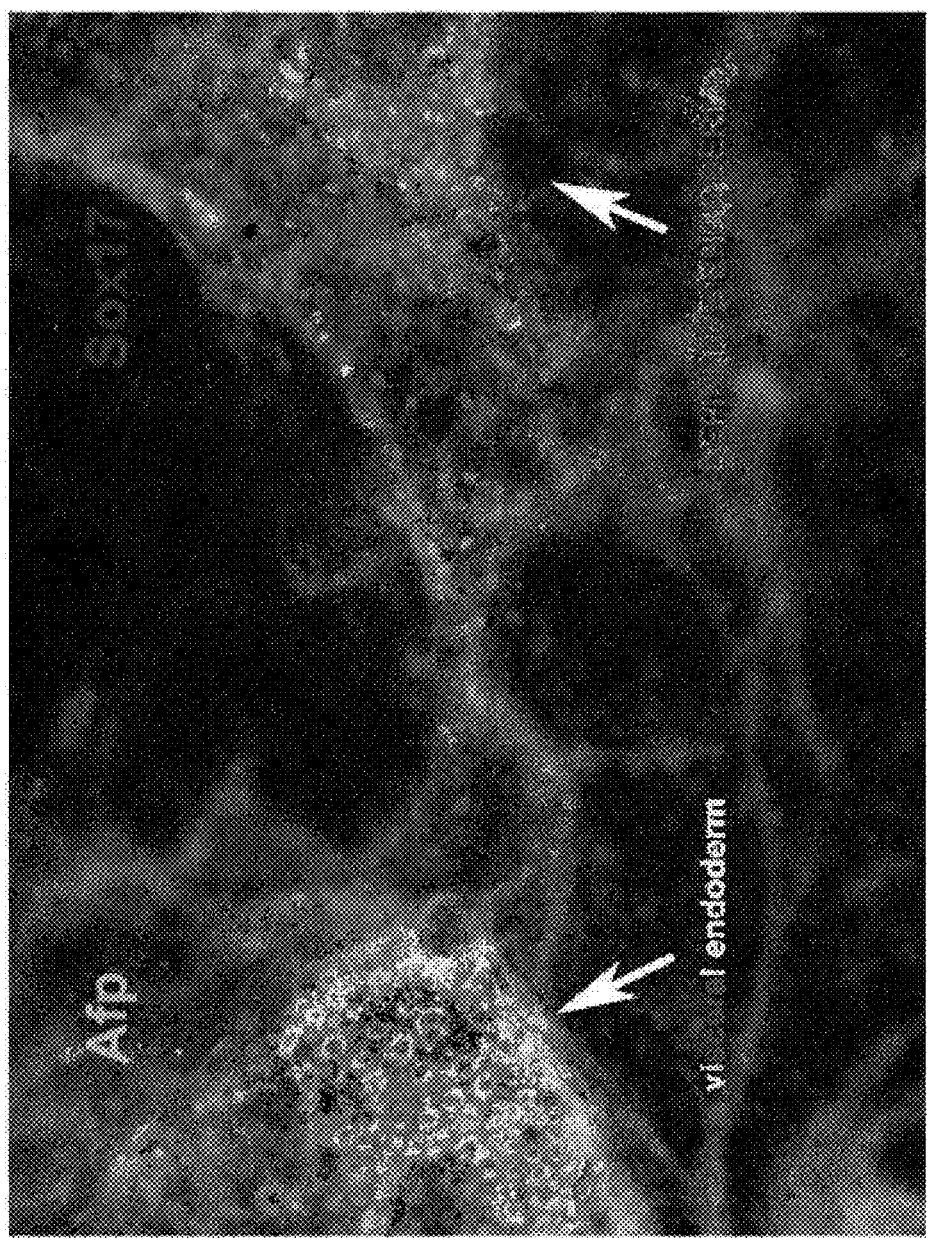
FIG. 17 is a micrograph showing the appearance of definitive endoderm and visceral endoderm in vitro from hESCs. The regions of visceral endoderm are identified by AFP$^{hi}$/SOX17$^{lo/-}$ while definitive endoderm displays the complete opposite profile, SOX17$^{hi}$/AFP$^{lo/-}$. This field was selectively chosen due to the proximity of these two regions to each other. However, there are numerous times when SOX17$^{hi}$/AFP$^{lo/-}$ regions are observed in absolute isolation from any regions of AFP$^{hi}$ cells, suggesting the separate origination of the definitive endoderm cells from visceral endoderm cells.
Figure 18:
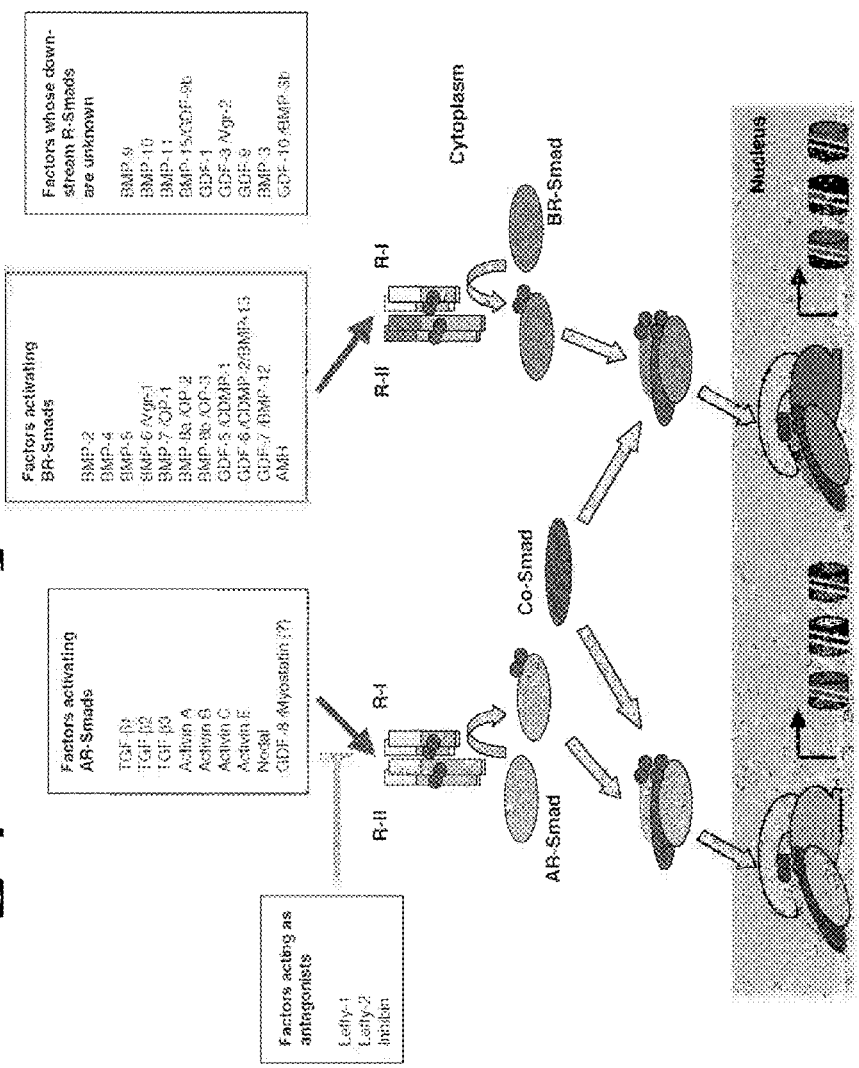
FIG. 18 is a diagram depicting the TGFβ family of ligands and receptors. Factors activating AR Smads and BR Smads are useful in the production of definitive endoderm from human embryonic stem cells (see, *J Cell Physiol.* 187:265-76).

Based on negative correlations of SOX17 and SPARC gene expression levels by Q-PCR, the vast majority of these SOX17 positive, AFP negative cells will be negative for parietal markers by antibody co-labeling. This was specifically demonstrated for TM-expressing parietal endoderm cells as shown in FIGS. 15A-B. Exposure to Nodal factors Activin A and B resulted in a dramatic decrease in the intensity to TM expression and the number of TM positive cells. By triple labeling using SOX17, AFP and TM antibodies on an activin treated culture, clusters of SOX17 positive cells which were also negative for AFP and TM were observed (FIGS. 16A-D). These are the first cellular demonstrations of SOX17 positive definitive endoderm cells in differentiating ESC cultures (FIGS. 16A-D and 17).

With the SOX17 antibody and Q-PCR tools described above we have explored a number of procedures capable of efficiently programming ESCs to become SOX17$^{hi}$/AFP$^{lo}$/SPARC/TM$^{lo}$ definitive endoderm cells. We applied a variety of differentiation protocols aimed at increasing the number and proliferative capacity of these cells as measured at the population level by Q-PCR for SOX17 gene expression and at the level of individual cells by antibody labeling of SOX17 protein.

We were the first to analyze and describe the effect of TGFβ family growth factors, such as Nodal/activin/BMP, for use in creating definitive endoderm cells from embryonic stem cells in in vitro cell cultures. In typical experiments, Activin A, Activin B, BMP or combinations of these growth factors were added to cultures of undifferentiated human stem cell line hESCyt-25 to begin the differentiation process.

Figure 19:
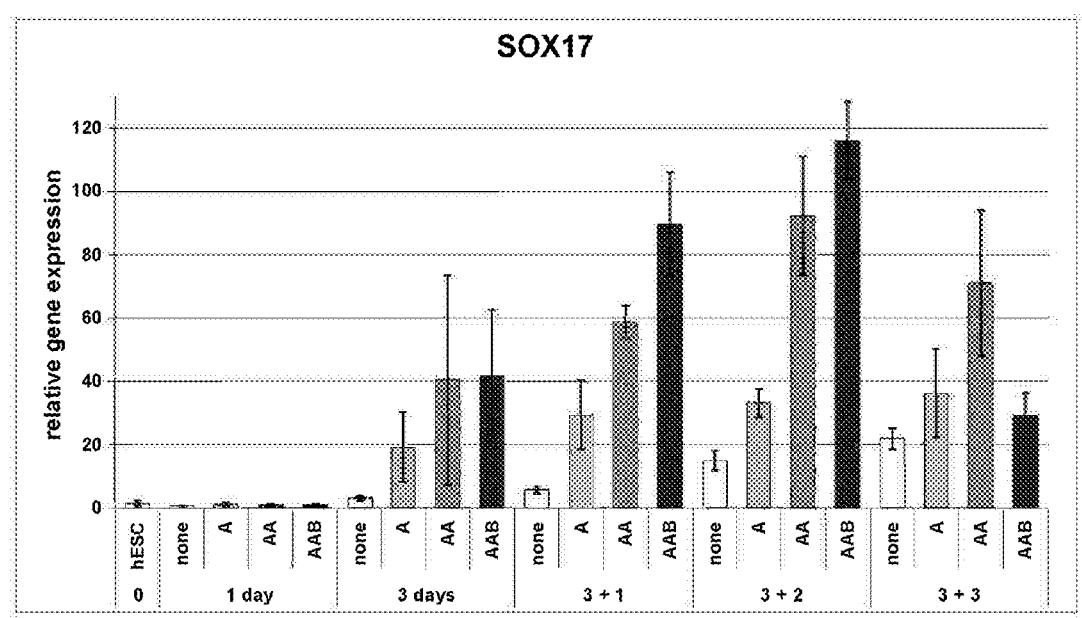
FIG. 19 is a bar chart showing the induction of SOX17 expression over time as a result of treatment with individual and combinations of TGFβ factors.

As shown in FIG. 19, addition of Activin A at 100 ng/ml resulted in a 19-fold induction of SOX17 gene expression vs. undifferentiated hESCs by day 4 of differentiation. Adding Activin B, a second member of the activin family, together with Activin A, resulted in a 37-fold induction over undifferentiated hESCs by day 4 of combined activin treatment. Finally, adding a third member of the TGFβ family from the Nodal/Activin and BMP subgroups, BMP4, together with Activin A and Activin B, increased the fold induction to 57 times that of undifferentiated hESCs (FIG. 19). When SOX17 induction with activins and BMP was compared to no factor medium controls 5-, 10-, and 15-fold inductions resulted at the 4-day time point. By five days of triple treatment with Activins A, B and BMP, SOX17 was induced more than 70 times higher than hESCs. These data indicate that higher doses and longer treatment times of the Nodal/activin TGFβ family members results in increased expression of SOX17.

Nodal and related molecules Activin A, B and BMP facilitate the expression of SOX17 and definitive endoderm formation in vivo or in vitro. Furthermore, addition of BMP results in an improved SOX17 induction possibly through the further induction of Cripto, the Nodal co-receptor.

We have demonstrated that the combination of Activins A and B together with BMP4 result in additive increases in SOX17 induction and hence definitive endoderm formation. BMP4 addition for prolonged periods (>4 days), in combination with Activin A and B may induce SOX17 in parietal and visceral endoderm as well as definitive endoderm. In some embodiments of the present invention, it is therefore valuable to remove BMP4 from the treatment within 4 days of addition.

Figure 20:
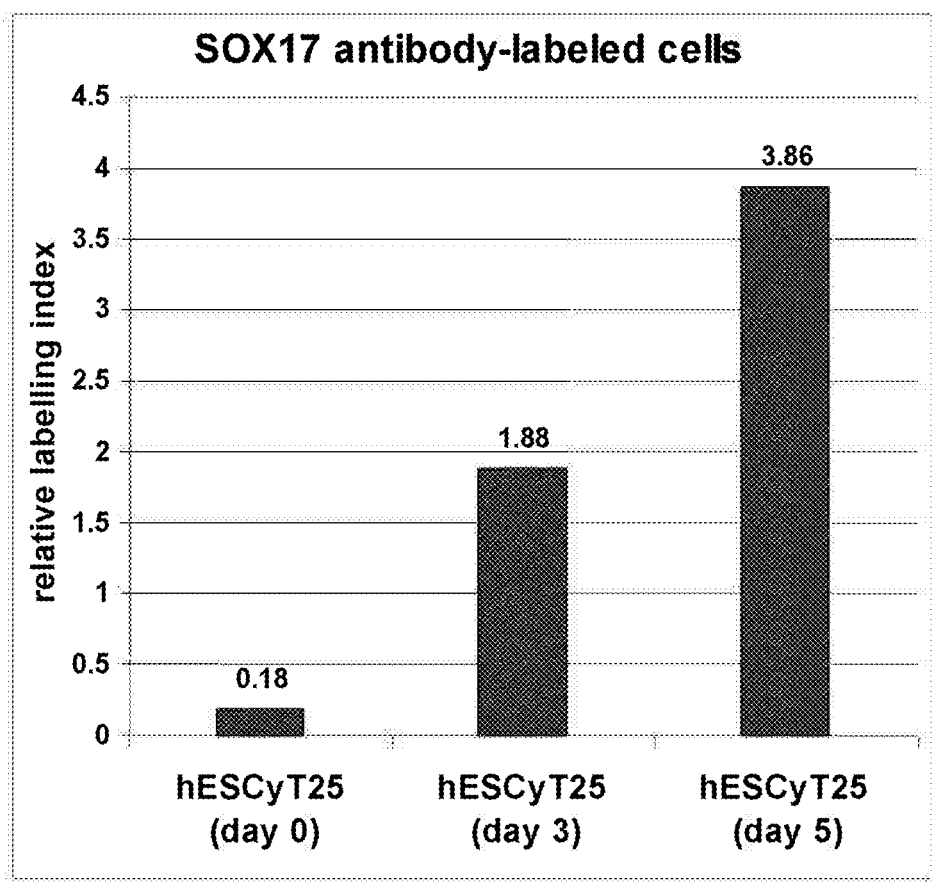
FIG. 20 is a bar chart showing the increase in SOX17$^+$ cell number with time as a result of treatment with combinations of TGFβ factors.
Figure 21:
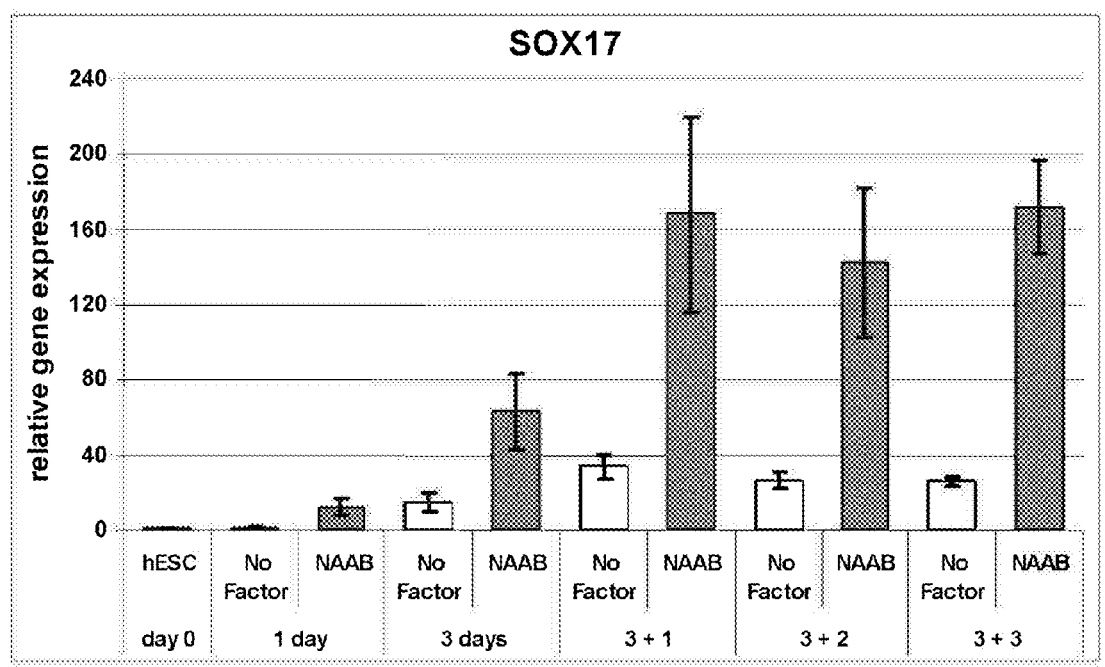
FIG. 21 is a bar chart showing induction of SOX17 expression over time as a result of treatment with combinations of TGFβ factors.
Figure 22:
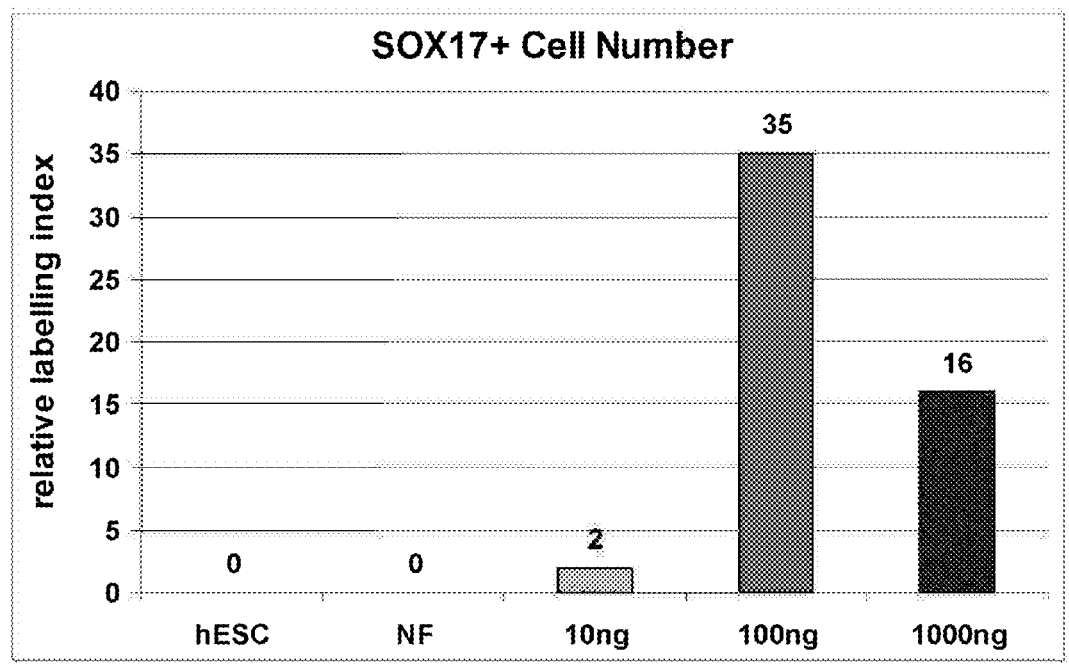
FIG. 22 is a bar chart showing that Activin A induces a dose-dependent increase in SOX17$^+$ cell number.

To determine the effect of TGFβ factor treatment at the individual cell level, a time course of TGFβ factor addition was examined using SOX17 antibody labeling. As previously shown in FIGS. 10A-F, there was a dramatic increase in the relative number of SOX17 labeled cells over time. The relative quantification (FIG. 20) shows more than a 20-fold increase in SOX17-labeled cells. This result indicates that both the numbers of cells as well SOX17 gene expression level are increasing with time of TGFβ factor exposure. As shown in FIG. 21, after four days of exposure to Nodal, Activin A, Activin B and BMP4, the level of SOX17 induction reached 168-fold over undifferentiated hESCs. FIG. 22 shows that the relative number of SOX17-positive cells was also dose responsive. Activin A doses of 100 ng/mL or more were capable of potently inducing SOX17 gene expression and cell number.

Figure 23:
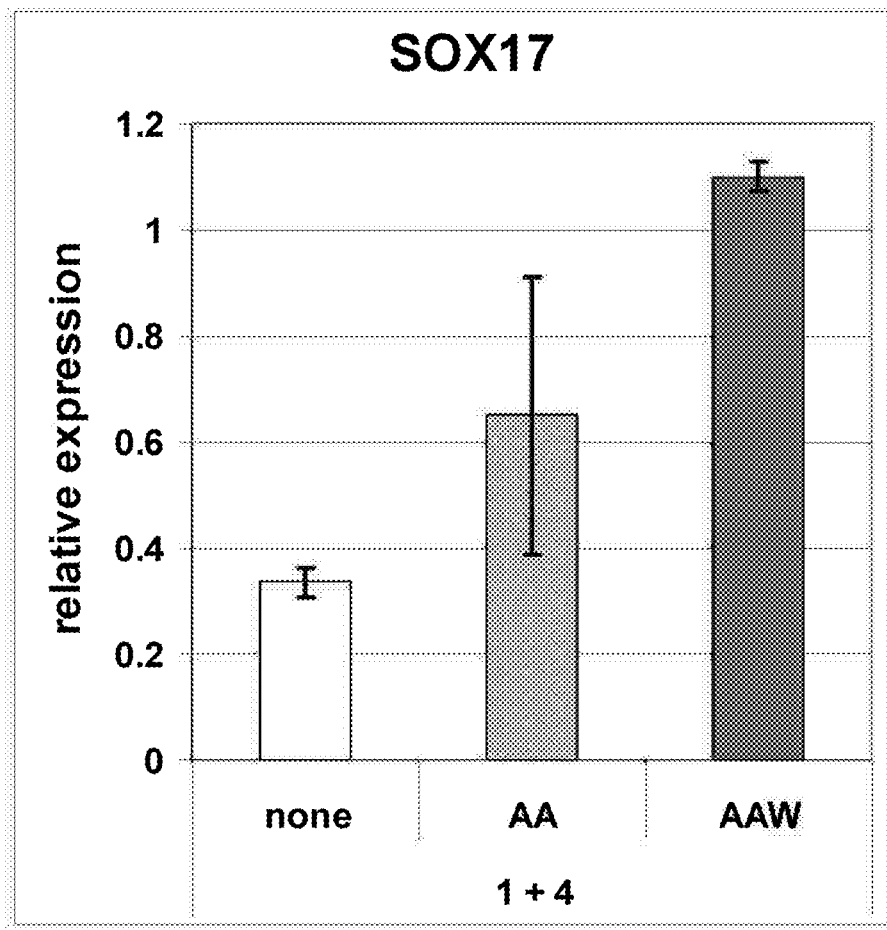
FIG. 23 is a bar chart showing that addition of Wnt3a to Activin A and Activin B treated cultures increases SOX17 expression above the levels induced by Activin A and Activin B alone.

In addition to the TGFβ family members, the Wnt family of molecules may play a role in specification and/or maintenance of definitive endoderm. The use of Wnt molecules was also beneficial for the differentiation of hESCs to definitive endoderm as indicted by the increased SOX17 gene expression in samples that were treated with activins plus Wnt3a over that of activins alone (FIG. 23).

Figure 24:
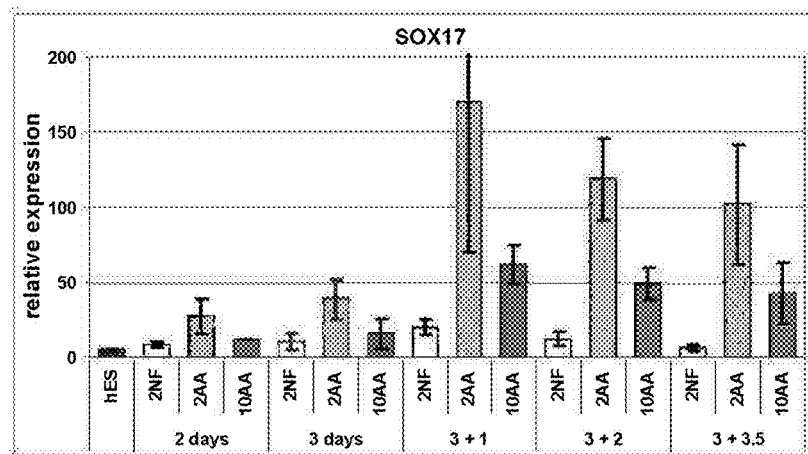
FIGS. 24A-C are bar charts showing differentiation to definitive endoderm is enhanced in low FBS conditions. Treatment of hESCs with activins A and B in media containing 2% FBS (2AA) yields a 2-3 times greater level of SOX17 expression as compared to the same treatment in 10% FBS media (10AA) (panel A). Induction of the definitive endoderm marker MIXL1 (panel B) is also affected in the same way and the suppression of AFP (visceral endoderm) (panel C) is greater in 2% FBS than in 10% FBS conditions.
Figure 24:
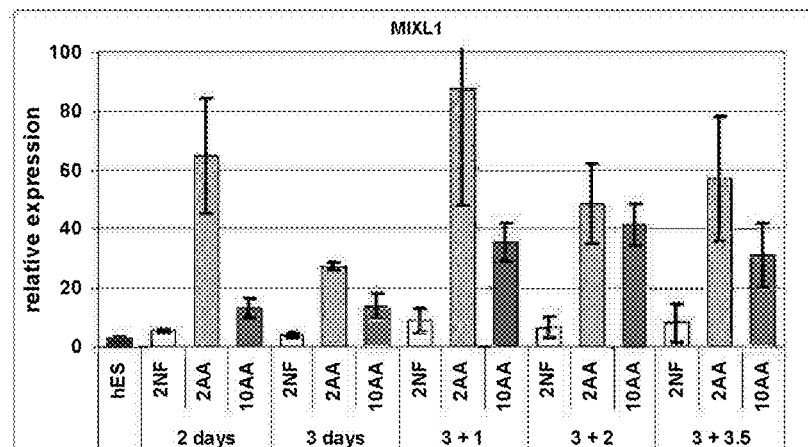
Figure 24:
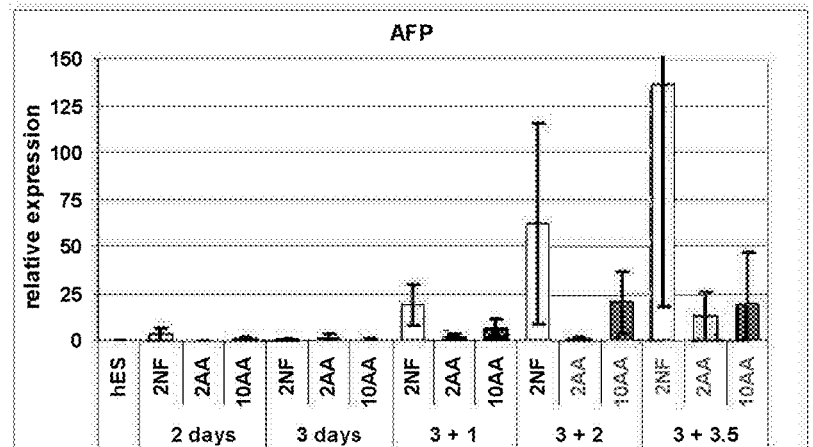
Figure 25:
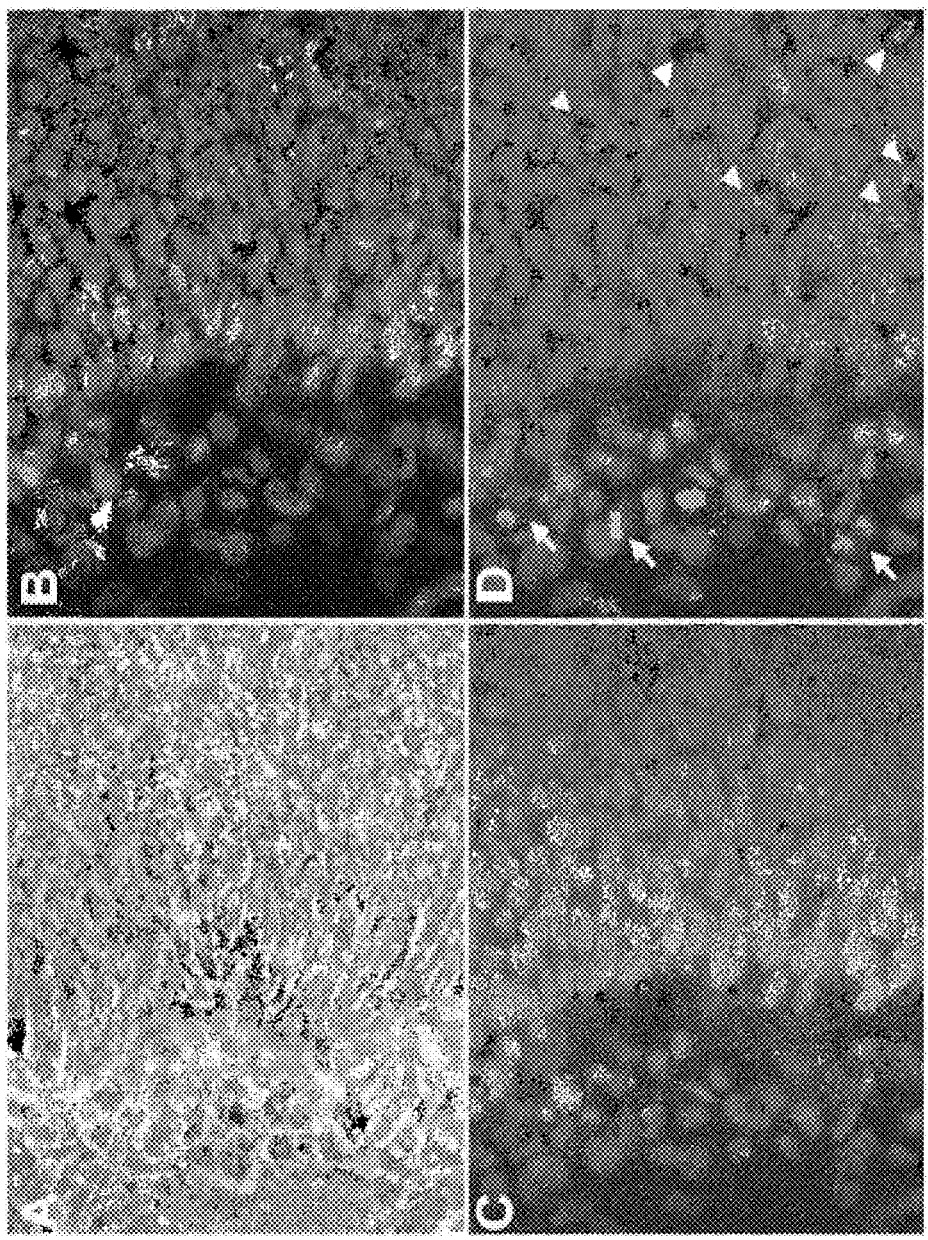
FIGS. 25A-D are micrographs which show SOX17+ cells are dividing in culture. SOX17 immunoreactive cells are present at the differentiating edge of an hESC colony (C, D) and are labeled with proliferating cell nuclear antigen (PCNA) (panel B) yet are not co-labeled with OCT4 (panel C). In addition, clear mitotic figures can be seen by DAPI labeling of nuclei in both SOX17+ cells (arrows) as well as OCT4+, undifferentiated hESCs (arrowheads) (D).

All of the experiments described above were performed using tissue culture medium containing 10% serum with added factors. Surprisingly, we discovered that the concentration of serum had an effect on the level of SOX17 expression in the presence of added activins as shown in FIGS. 24A-C. When serum levels were reduced from 10% to 2%, SOX17 expression tripled in the presence of Activins A and B.

Finally, we demonstrated that activin induced SOX17$^+$ cells divide in culture as depicted in FIGS. 25A-D. The arrows show cells labeled with SOX17/PCNA/DAPI that are in mitosis as evidenced by the PCNA/DAPI-labeled mitotic plate pattern and the phase contrast mitotic profile.

Example 7

Chemokine Receptor 4 (CXCR4) Expression Correlates with Markers for Definitive Endoderm and not Markers for Mesoderm Ectoderm or Visceral Endoderm As described above, ESCs can be induced to differentiate to the definitive endoderm germ layer by the application of cytokines of the TGFβ family and more specifically of the activin/nodal subfamily. Additionally, we have shown that the proportion of fetal bovine serum (FBS) in the differentiation culture medium effects the efficiency of definitive endoderm differentiation from ESCs. This effect is such that at a given concentration of activin A in the medium, higher levels of FBS will inhibit maximal differentiation to definitive endoderm. In the absence of exogenous activin A, differentiation of ESCs to the definitive endoderm lineage is very inefficient and the FBS concentration has much milder effects on the differentiation process of ESCs.

In these experiments, hESCs were differentiated by growing in RPMI medium (Invitrogen, Carlsbad, Calif.; cat#61870-036) supplemented with 0.5%, 2.0% or 10% FBS and either with or without 100 ng/mL activin A for 6 days. In addition, a gradient of FBS ranging from 0.5% to 2.0% over the first three days of differentiation was also used in conjunction with 100 ng/mL of activin A. After the 6 days, replicate samples were collected from each culture condition and analyzed for relative gene expression by real-time quantitative PCR. The remaining cells were fixed for immunofluorescent detection of SOX17 protein.

Figure 26:
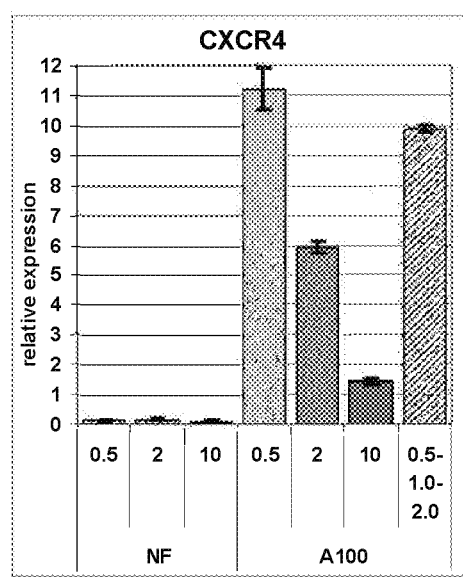
FIG. 26 is a bar chart showing the relative expression level of CXCR4 in differentiating hESCs under various media conditions.
Figure 27:
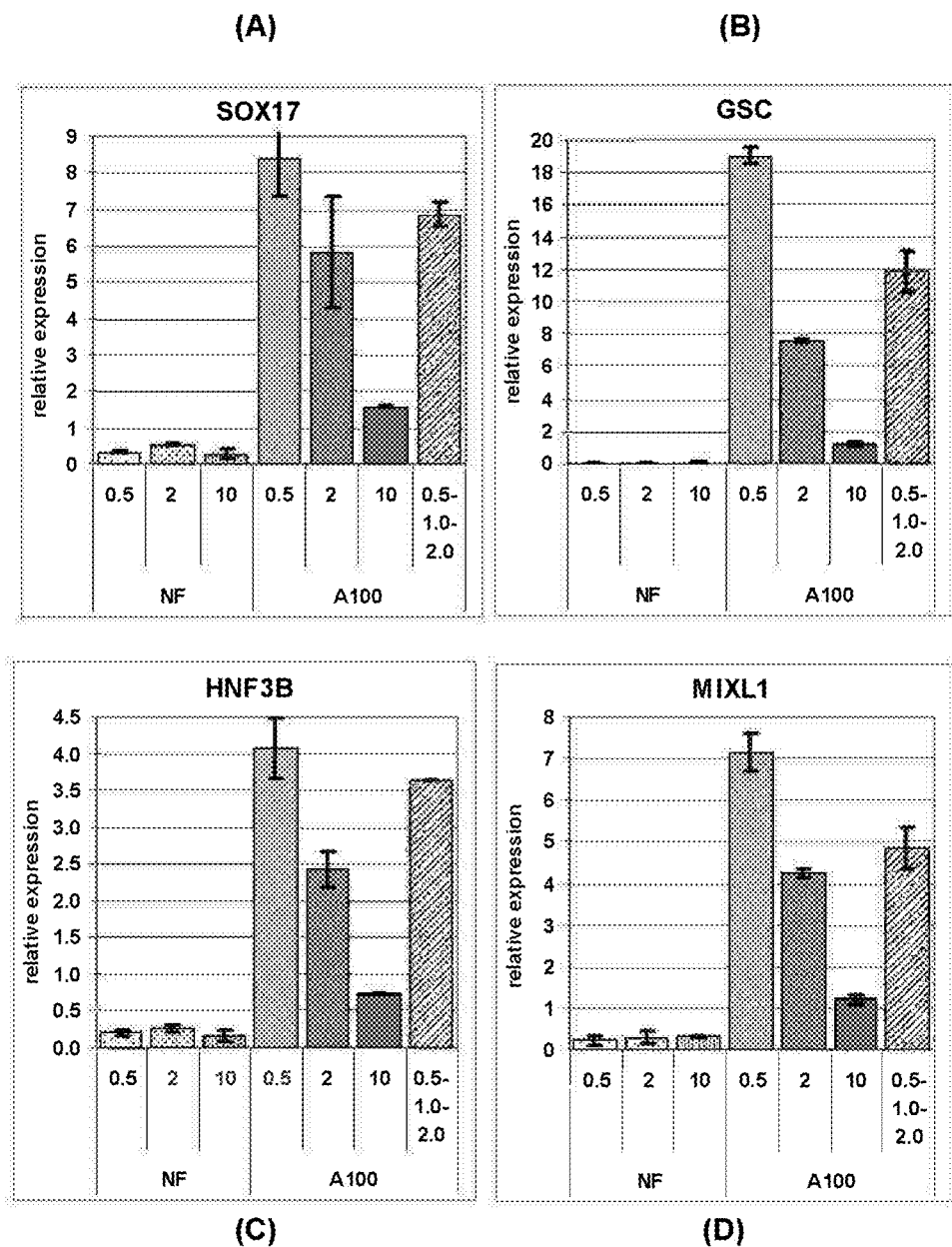
FIGS. 27A-D are bar charts that show how a panel of definitive endoderm markers share a very similar pattern of expression to CXCR4 across the same differentiation treatments displayed in FIG. 26.

The expression levels of CXCR4 varied dramatically across the 7 culture conditions used (FIG. 26). In general, CXCR4 expression was high in activin A treated cultures (A100) and low in those which did not receive exogenous activin A (NF). In addition, among the A100 treated cultures, CXCR4 expression was highest when FBS concentration was lowest. There was a remarkable decrease in CXCR4 level in the 10% FBS condition such that the relative expression was more in line with the conditions that did not receive activin A (NF).

As described above, expression of the SOX17, GSC, MIXL1, and HNF3β genes is consistent with the characterization of a cell as definitive endoderm. The relative expression of these four genes across the 7 differentiation conditions mirrors that of CXCR4 (FIGS. 27A-D). This demonstrates that CXCR4 is also a marker of definitive endoderm.

Ectoderm and mesoderm lineages can be distinguished from definitive endoderm by their expression of various markers. Early mesoderm expresses the genes Brachyury and MOX1 while nascent neuro-ectoderm expresses SOX1 and ZIC1. FIGS. 28A-D demonstrate that the cultures which did not receive exogenous activin A were preferentially enriched for mesoderm and ectoderm gene expression and that among the activin A treated cultures, the 10% FBS condition also had increased levels of mesoderm and ectoderm marker expression. These patterns of expression were inverse to that of CXCR4 and indicated that CXCR4 was not highly expressed in mesoderm or ectoderm derived from ESCs at this developmental time period.

Figure 28:
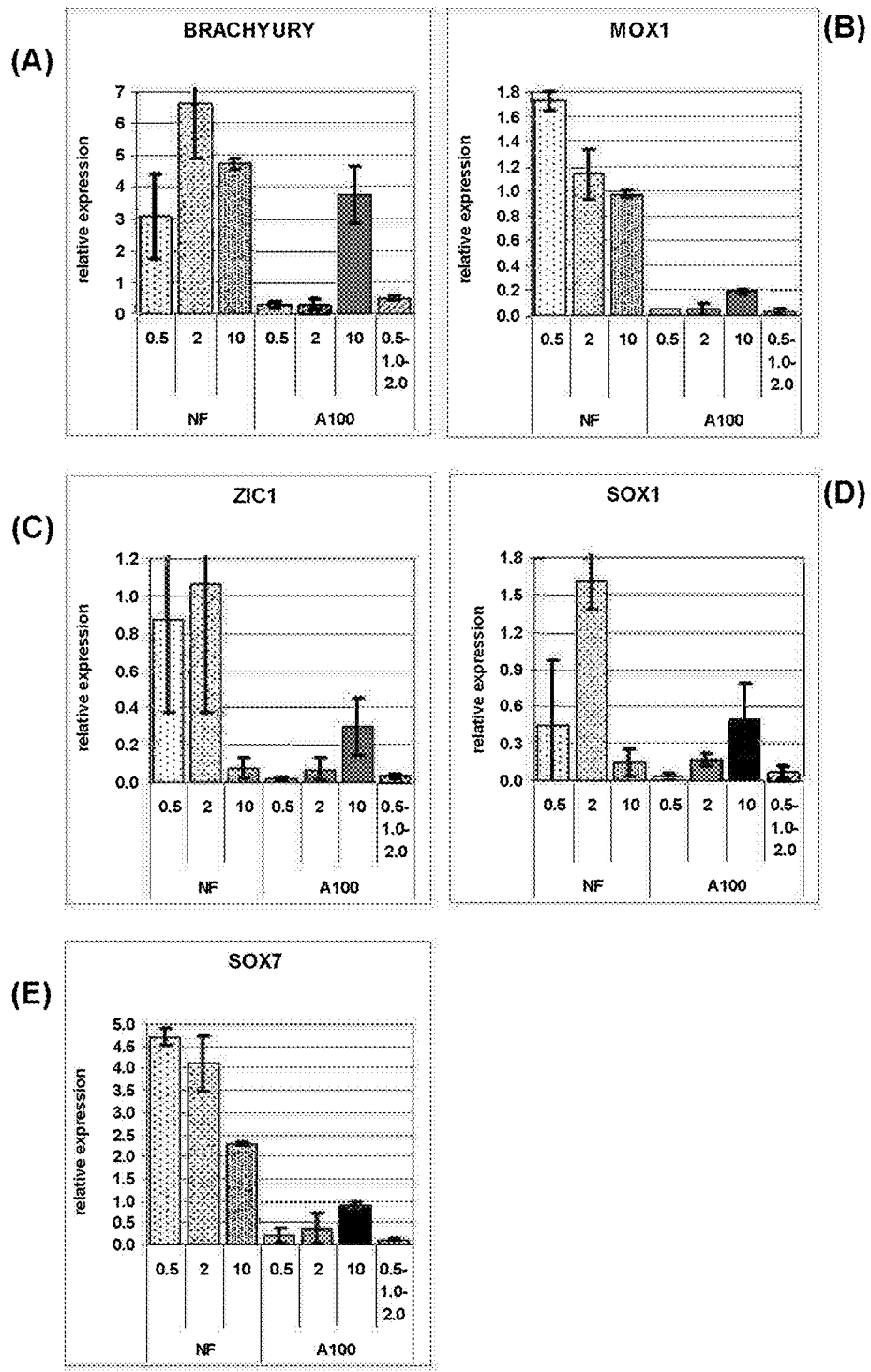
FIGS. 28A-E are bar charts showing how markers for mesoderm (BRACHYURY, MOX1), ectoderm (SOX1, ZIC1) and visceral endoderm (SOX7) exhibit an inverse relationship to CXCR4 expression across the same treatments displayed in FIG. 26.

Early during mammalian development, differentiation to extra-embryonic lineages also occurs. Of particular relevance here is the differentiation of visceral endoderm that shares the expression of many genes in common with definitive endoderm, including SOX17. To distinguish definitive endoderm from extra-embryonic visceral endoderm one should examine a marker that is distinct between these two. SOX7 represents a marker that is expressed in the visceral endoderm but not in the definitive endoderm lineage. Thus, culture conditions that exhibit robust SOX17 gene expression in the absence of SOX7 expression are likely to contain definitive and not visceral endoderm. It is shown in FIG. 28E that SOX7 was highly expressed in cultures that did not receive activin A, SOX7 also exhibited increased expression even in the presence of activin A when FBS was included at 10%. This pattern is the inverse of the CXCR4 expression pattern and suggests that CXCR4 is not highly expressed in visceral endoderm.

Figure 29:
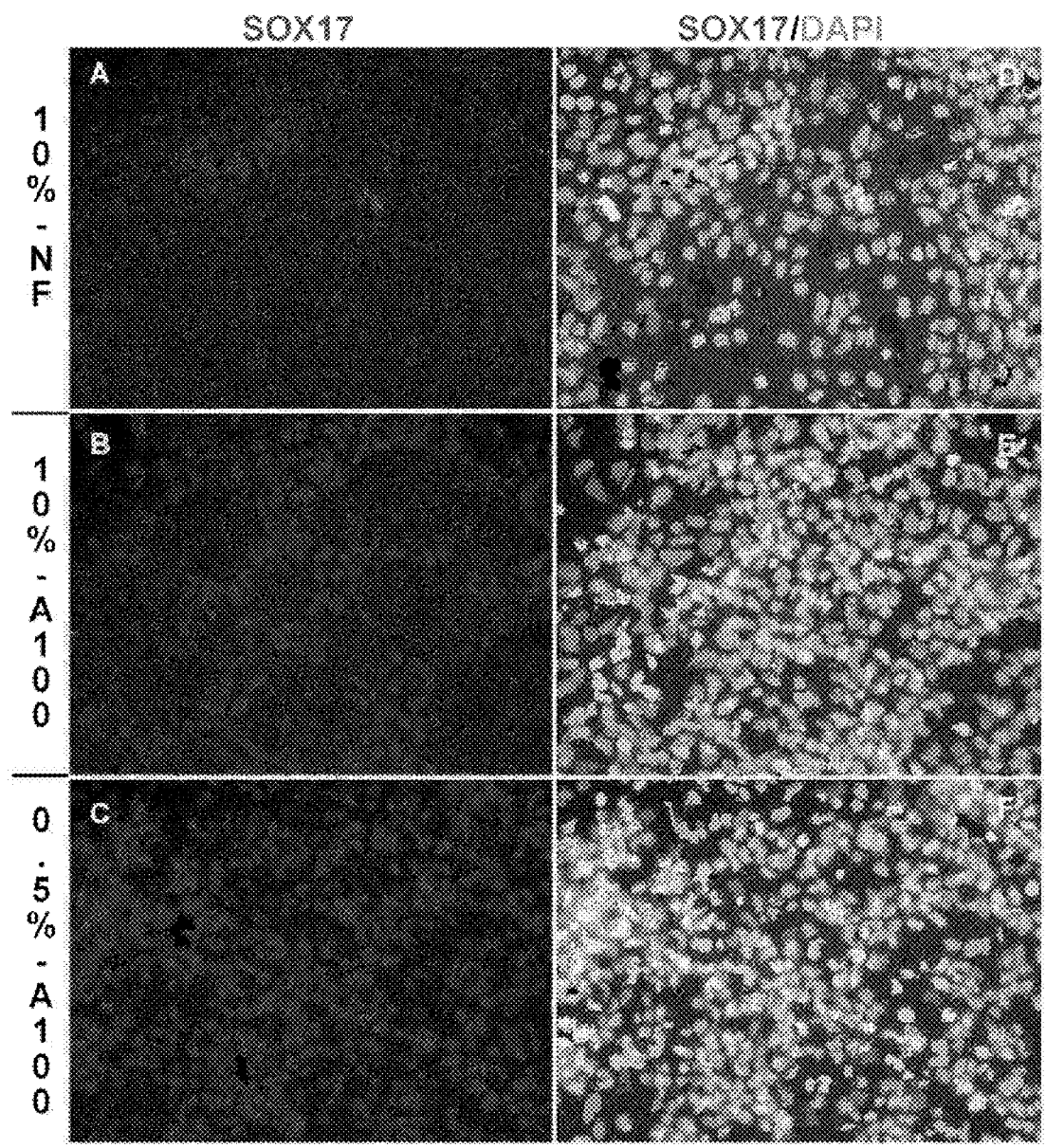
FIGS. 29A-F are micrographs that show the relative difference in SOX17 immunoreactive cells across three of the media conditions displayed in FIGS. 26-28.

The relative number of SOX17 immunoreactive (SOX17$^+$) cells present in each of the differentiation conditions mentioned above was also determined. When hESCs were differentiated in the presence of high dose activin A and low FBS concentration (0.5%-2.0%) SOX17$^+$ cells were ubiquitously distributed throughout the culture. When high dose activin A was used but FBS was included at 10% (v/v), the SOX17$^+$ cells appeared at much lower frequency and always appeared in isolated clusters rather than evenly distributed throughout the culture (FIGS. 29A and C as well as B and E). A further decrease in SOX17$^+$ cells was seen when no exogenous activin A was used. Under these conditions the SOX17$^+$ cells also appeared in clusters and these clusters were smaller and much more rare than those found in the high activin A, low FBS treatment (FIGS. 29 C and F). These results demonstrate that the CXCR4 expression patterns not only correspond to definitive endoderm gene expression but also to the number of definitive endoderm cells in each condition.

Example 8

Differentiation Conditions that Enrich for Definitive Endoderm Increase the Proportion of CXCR4 Positive Cells The dose of activin A also effects the efficiency at which definitive endoderm can be derived from ESCs. This example demonstrates that increasing the dose of activin A increases the proportion of CXCR4$^+$ cells in the culture.

hESCs were differentiated in RPMI media supplemented with 0.5%-2% FBS (increased from 0.5% to 1.0% to 2.0% over the first 3 days of differentiation) and either 0, 10, or 100 ng/mL of activin A. After 7 days of differentiation the cells were dissociated in PBS without Ca$^{2+}$/Mg$^{2+}$ containing 2% FBS and 2 mM (EDTA) for 5 minutes at room temperature. The cells were filtered through 35 um nylon filters, counted and pelleted. Pellets were resuspended in a small volume of 50% human serum/50% normal donkey serum and incubated for 2 minutes on ice to block non-specific antibody binding sites. To this, 1 uL of mouse anti-CXCR4 antibody (Abcam, cat# ab10403-100) was added per 50 uL (containing approximately 10$^5$ cells) and labeling proceeded for 45 minutes on ice. Cells were washed by adding 5 mL of PBS containing 2% human serum (buffer) and pelleted. A second wash with 5 mL of buffer was completed then cells were resuspended in 50 uL buffer per 10$^5$ cells. Secondary antibody (FITC conjugated donkey anti-mouse; Jackson ImmunoResearch, cat#715-096-151) was added at 5 ug/mL final concentration and allowed to label for 30 minutes followed by two washes in buffer as above. Cells were resuspended at 5×10$^6$ cells/mL in buffer and analyzed and sorted using a FACS Vantage (Beckton Dickenson) by the staff at the flow cytometry core facility (The Scripps Research Institute). Cells were collected directly into RLT lysis buffer (Qiagen) for subsequent isolation of total RNA for gene expression analysis by real-time quantitative PCR.

Figure 30A:
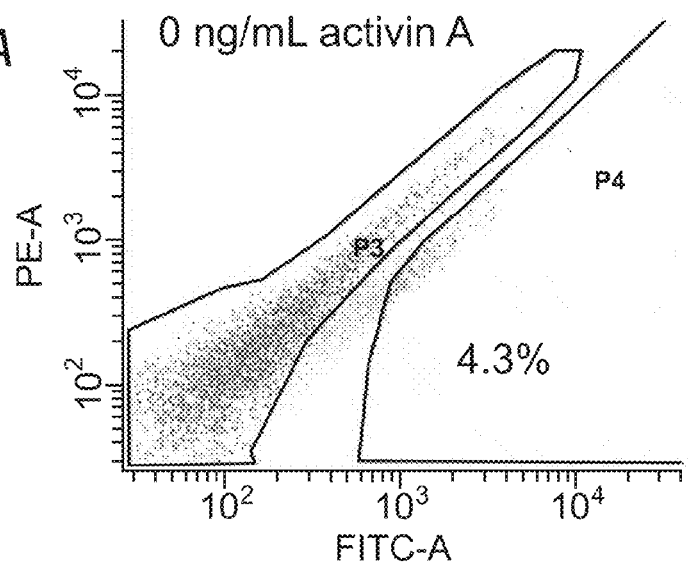
FIGS. 30A-C are flow cytometry dot plots that demonstrate the increase in CXCR4+ cell number with increasing concentration of activin A added to the differentiation media.
Figure 30B:
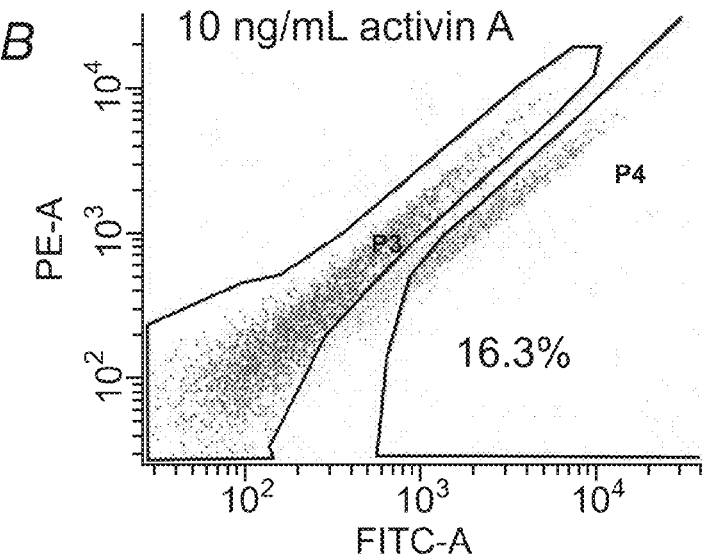
Figure 30C:
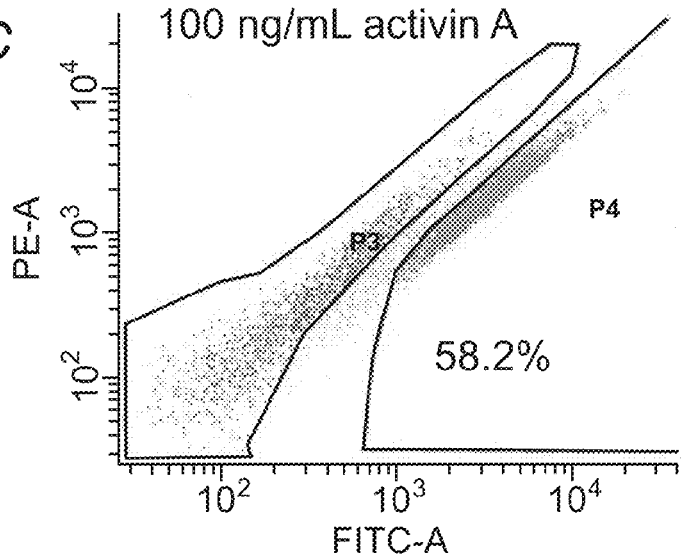
Figure 31:
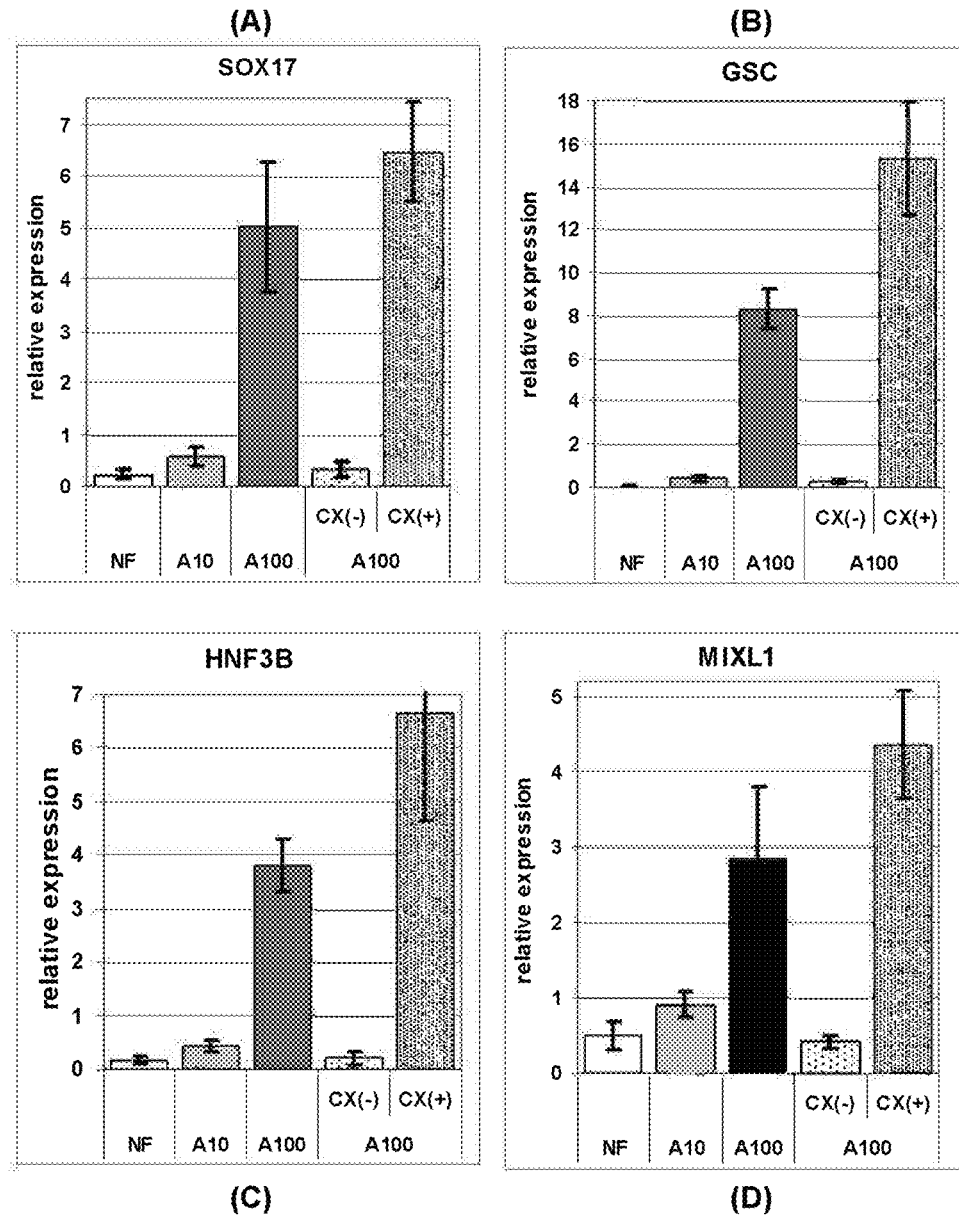
FIGS. 31A-D are bar charts that show the CXCR4+ cells isolated from the high dose activin A treatment (A100-CX+) are even further enriched for definitive endoderm markers than the parent population (A100).

The number of CXCR4$^+$ cells as determined by flow cytometry were observed to increase dramatically as the dose of activin A was increased in the differentiation culture media (FIGS. 30A-C). The CXCR4$^+$ cells were those falling within the R4 gate and this gate was set using a secondary antibody-only control for which 0.2% of events were located in the R4 gate. The dramatically increased numbers of CXCR4$^+$ cells correlates with a robust increase in definitive endoderm gene expression as activin A dose is increased (FIGS. 31A-D).

Example 9

Isolation of CXCR4 Positive Cells Enriches for Definitive Endoderm Gene Expression and Depletes Cells Expressing Markers of Mesoderm, Ectoderm and Visceral Endoderm The CXCR4$^+$ and CXCR4$^-$ cells identified in Example 8 above were collected and analyzed for relative gene expression and the gene expression of the parent populations was determined simultaneously.

Figure 32:
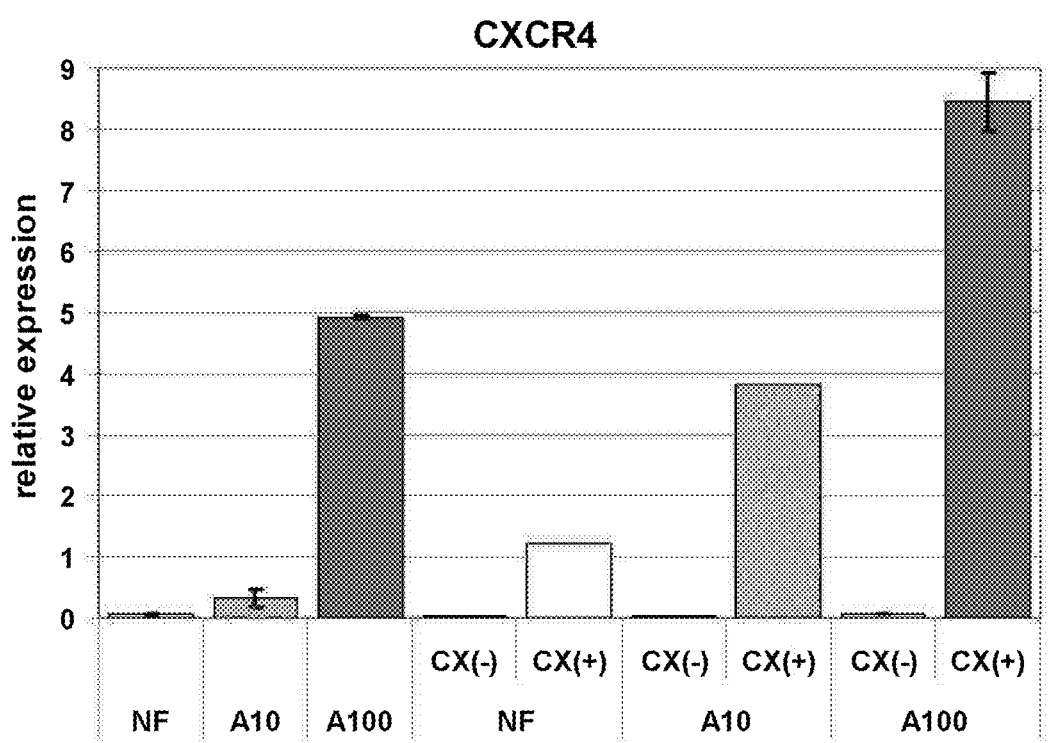
FIG. 32 is a bar chart showing gene expression from CXCR4+ and CXCR4− cells isolated using fluorescence-activated cell sorting (FACS) as well as gene expression in the parent populations. This demonstrates that the CXCR4+ cells contain essentially all the CXCR4 gene expression present in each parent population and the CXCR4− populations contain very little or no CXCR4 gene expression.
Figure 33:
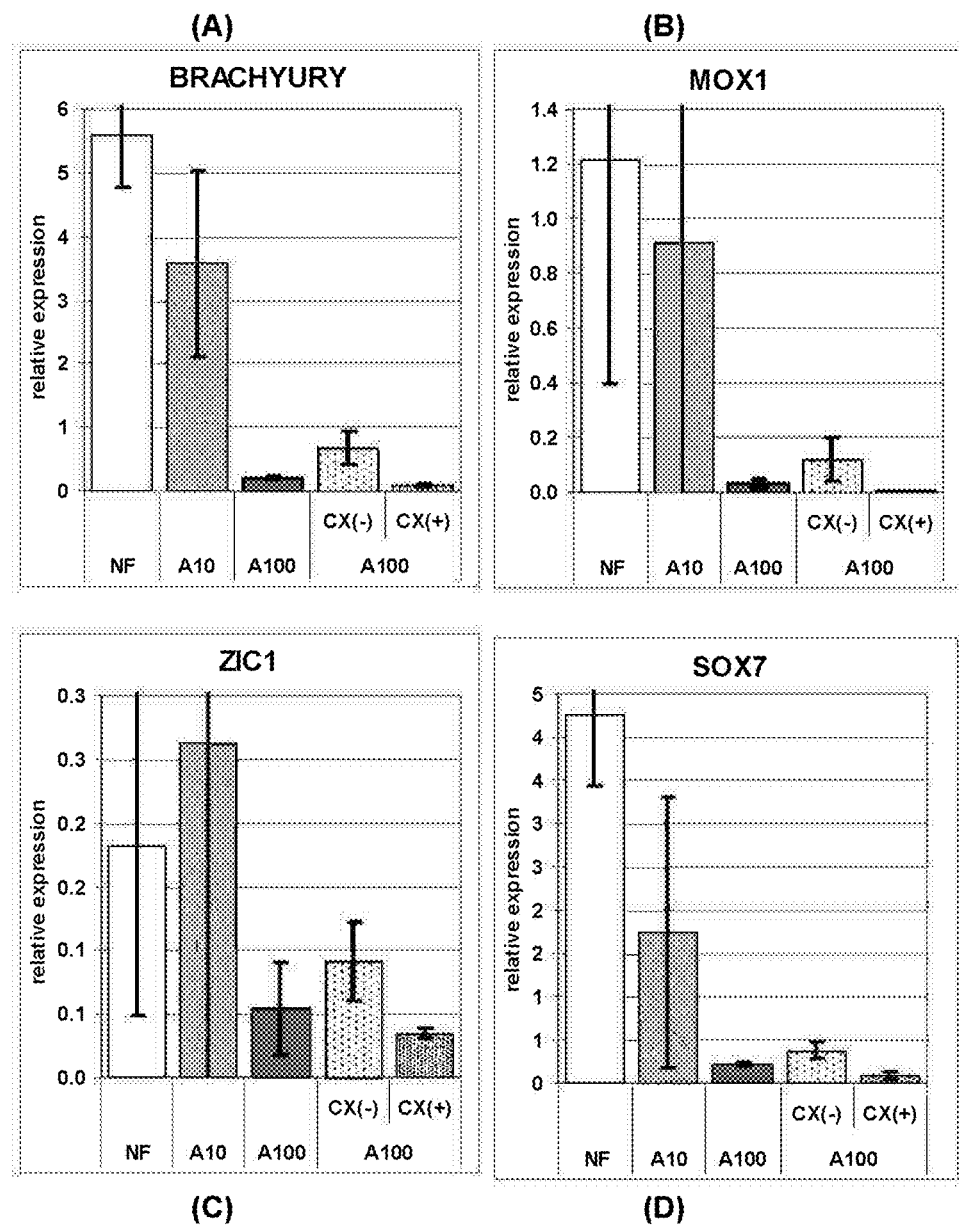
FIGS. 33A-D are bar charts that demonstrate the depletion of mesoderm (BRACHYURY, MOX1), ectoderm (ZIC1) and visceral endoderm (SOX7) gene expression in the CXCR4+ cells isolated from the high dose activin A treatment which is already suppressed in expression of these non-definitive endoderm markers.

The relative levels of CXCR4 gene expression was dramatically increased with increasing dose of activin A (FIG. 32). This correlated very well with the activin A dose-dependent increase of CXCR4+ cells (FIGS. 30A-C). It is also clear that isolation of the CXCR4+ cells from each population accounted for nearly all of the CXCR4 gene expression in that population. This demonstrates the efficiency of the FACS method for collecting these cells.

Gene expression analysis revealed that the CXCR4+ cells contain not only the majority of the CXCR4 gene expression, but they also contained other gene expression for markers of definitive endoderm. As shown in FIGS. 31A-D, the CXCR4+ cells were further enriched over the parent A100 population for SOX17, GSC, HNF3B, and MIXL1. In addition, the CXCR4− fraction contained very little gene expression for these definitive endoderm markers. Moreover, the CXCR4+ and CXCR4− populations displayed the inverse pattern of gene expression for markers of mesoderm, ectoderm and extra-embryonic endoderm. FIGS. 33A-D shows that the CXCR4+ cells were depleted for gene expression of Brachyury, MOX1, ZIC1, and SOX7 relative to the A100 parent population. This A100 parent population was already low in expression of these markers relative to the low dose or no activin A conditions. These results show that the isolation of CXCR4+ cells from hESCs differentiated in the presence of high activin A yields a population that is highly enriched for and substantially pure definitive endoderm.

Example 10

Quantitation of Definitive Endoderm Cells in a Cell Population Using CXCR4

To confirm the quantitation of the proportion of definitive endoderm cells present in a cell culture or cell population as determined previously herein and as determined in U.S. Provisional Patent Application No. 60/532,004, entitled DEFINITIVE ENDODERM, filed Dec. 23, 2003, the disclosure of which is incorporated herein by reference in its entirety, cells expressing CXCR4 and other markers of definitive endoderm were analyzed by FACS.

Using the methods such as those described in the above Examples, hESCs were differentiated to produce definitive endoderm. In particular, increase yield and purity expressed in differentiating cell cultures, the serum concentration of the medium was controlled as follows: 0.2% FBS on day 1, 1.0% FBS on day 2 and 2.0% FBS on days 3-6. Differentiated cultures were sorted by FACS using three cell surface epitopes, E-Cadherin, CXCR4, and Thrombomodulin. Sorted cell populations were then analyzed by Q-PCR to determine relative expression levels of markers for definitive and extraembryonic-endoderm as well as other cell types. CXCR4 sorted cells taken from optimally differentiated cultures resulted in the isolation of definitive endoderm cells that were >98% pure.

Table 2 shows the results of a marker analysis for a definitive endoderm culture that was differentiated from hESCs using the methods described herein.

TABLE 2

Composition of Definitive Endoderm Cultures

| Marker(s) | Percent of culture | Percent Definitive Endoderm | Percent Extraembryonic endododerm | Percent hES cells |
|---|---|---|---|---|
| SOX17 | 70-80 | 100 | | |
| Thrombomodulin | <2 | 0 | 75 | |
| AFP | <1 | 0 | 25 | |
| CXCR4 | 70-80 | 100 | 0 | |
| ECAD | 10 | 0 | | 100 |
| other (ECAD neg.) | 10-20 | | | |
| Total | 100 | 100 | 100 | 100 |

In particular, Table 2 indicates that CXCR4 and SOX17 positive cells (endoderm) comprised from 70%-80% of the cells in the cell culture. Of these SOX17-expressing cells, less than 2% expressed TM (parietal endoderm) and less than 1% expressed AFP (visceral endoderm). After subtracting the proportion of TM-positive and AFP-positive cells (combined parietal and visceral endoderm; 3% total) from the proportion of SOX17/CXCR4 positive cells, it can be seen that about 67% to about 77% of the cell culture was definitive endoderm. Approximately 10% of the cells were positive for E-Cadherin (ECAD), which is a marker for hESCs, and about 10-20% of the cells were of other cell types.

We have discovered that the purity of definitive endoderm in the differentiating cell cultures that are obtained prior to FACS separation can be improved as compared to the above-described low serum procedure by maintaining the FBS concentration at ≤0.5% throughout the 5-6 day differentiation procedure. However, maintaining the cell culture at ≤0.5% throughout the 5-6 day differentiation procedure also results in a reduced number of total definitive endoderm cells that are produced.

Definitive endoderm cells produced by methods described herein have been maintained and expanded in culture in the presence of activin for greater than 50 days without appreciable differentiation. In such cases, SOX17, CXCR4, MIXL1, GATA4, HNF3p expression is maintained over the culture period. Additionally, TM, SPARC, OCT4, AFP, SOX7, ZIC1 and BRACH were not detected in these cultures. It is likely that such cells can be maintained and expanded in culture for substantially longer than 50 days without appreciable differentiation.

Example 11

Additional Marker of Definitive Endoderm Cells

In the following experiment, RNA was isolated from purified definitive endoderm and human embryonic stem cell populations. Gene expression was then analyzed by gene chip analysis of the RNA from each purified population. Q-PCR was also performed to further investigate the potential of genes expressed in definitive endoderm, but not in embryonic stem cells, as a marker for definitive endoderm.

Human embryonic stem cells (hESCs) were maintained in DMEM/F12 media supplemented with 20% KnockOut Serum Replacement, 4 ng/mL recombinant human basic fibroblast growth factor (bFGF), 0.1 mM 2-mercaptoethanol, L-glutamine, non-essential amino acids and penicillin/streptomycin. hESCs were differentiated to definitive endoderm by culturing for 5 days in RPMI media supplemented with 100 ng/mL of recombinant human activin A, fetal bovine serum (FBS), and penicillin/streptomycin. The concentration of FBS was varied each day as follows: 0.1% (first day), 0.2% (second day), 2% (days 3-5).

Cells were isolated by fluorescence activated cell sorting (FACS) in order to obtain purified populations of hESCs and definitive endoderm for gene expression analysis. Immunopurification was achieved for hESCs using SSEA4 antigen (R&D Systems, cat# FAB1435P) and for definitive endoderm using CXCR4 (R&D Systems, cat# FAB170P). Cells were dissociated using trypsin/EDTA (Invitrogen, cat#25300-054), washed in phosphate buffered saline (PBS) containing 2% human serum and resuspended in 100% human serum on ice for 10 minutes to block non-specific binding. Staining was carried out for 30 minutes on ice by adding 200 uL of phycoerythrin-conjugated antibody to $5 \times 10^6$ cells in 800 uL human serum. Cells were washed twice with 8 mL of PBS buffer and resuspended in 1 mL of the same. FACS isolation was carried out by the core facility of The Scripps Research Institute using a FACS Vantage (BD Biosciences). Cells were collected directly into RLT lysis buffer and RNA was isolated by RNeasy according to the manufacturers instructions (Qiagen).

Purified RNA was submitted in duplicate to Expression Analysis (Durham, N.C.) for generation of the expression profile data using the Affymetrix platform and U133 Plus 2.0 high-density oligonucleotide arrays. Data presented is a group comparison that identifies genes differentially expressed between the two populations, hESCs and definitive endoderm. Genes that exhibited a robust upward change in expression level over that found in hESCs were selected as new candidate markers that are highly characteristic of definitive endoderm. Select genes were assayed by Q-PCR, as described above, to verify the gene expression changes found on the gene chip and also to investigate the expression pattern of these genes during a time course of hESC differentiation.

Figure 34A:
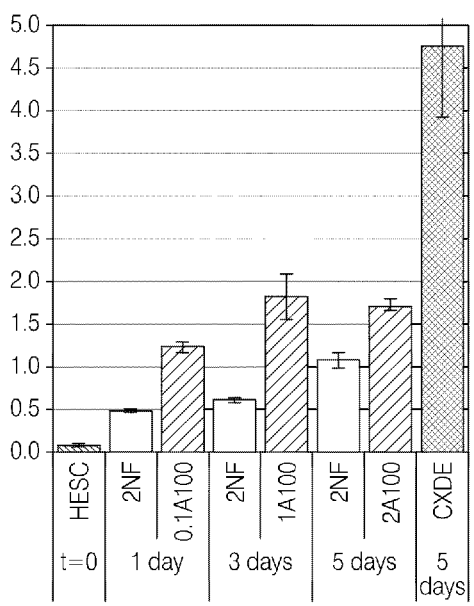
FIGS. 34A-M are bar charts showing the expression patterns of marker genes that can be used to identify definitive endoderm cells. The expression analysis of definitive endoderm markers, FGF17, VWF, CALCR, FOXQ1, CMKOR1 and CRIP1 is shown in panels G-L, respectively. The expression analysis of previously described lineage marking genes, SOX17, SOX7, SOX17/SOX7, TM, ZIC1, and MOX1 is shown in panels A-F, respectively. Panel M shows the expression analysis of CXCR4. With respect to each of panels A-M, the column labeled hESC indicates gene expression from purified human embryonic stem cells; 2NF indicates cells treated with 2% FBS, no activin addition; 0.1A100 indicates cells treated with 0.1% FBS, 100 ng/ml Activin A; 1A100 indicates cells treated with 1% FBS, 100 ng/ml Activin A; and 2A100 indicates cells treated with 2% FBS, 100 ng/ml Activin A.
Figure 34B:
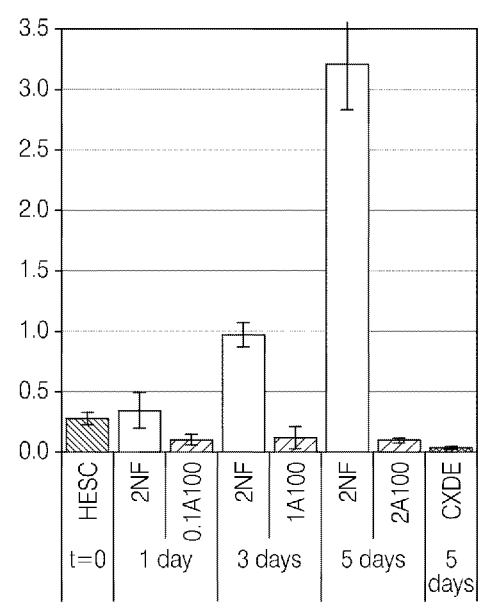
Figure 34C:
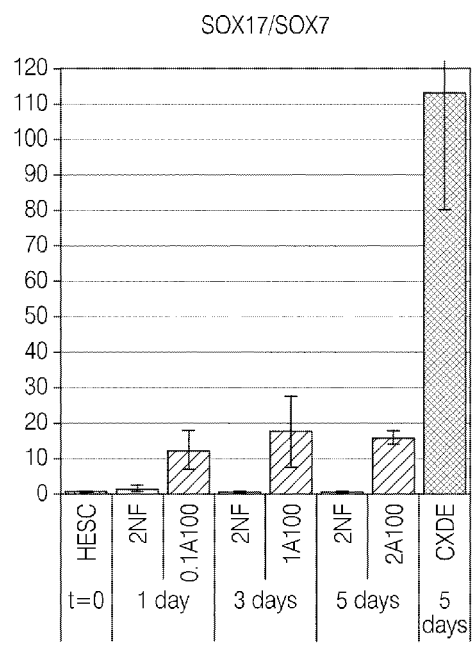
Figure 34D:
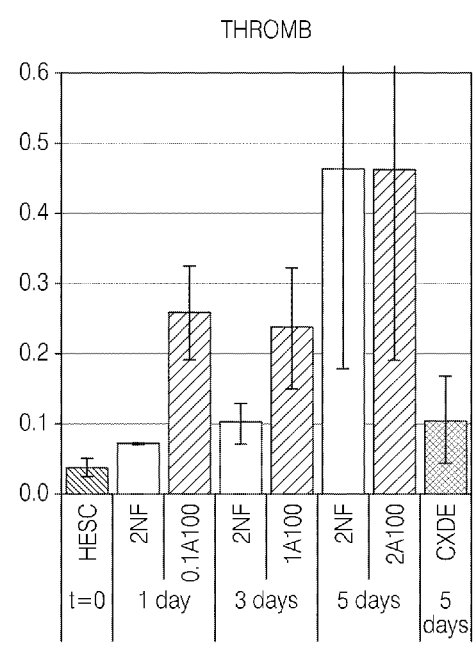
Figure 34E:
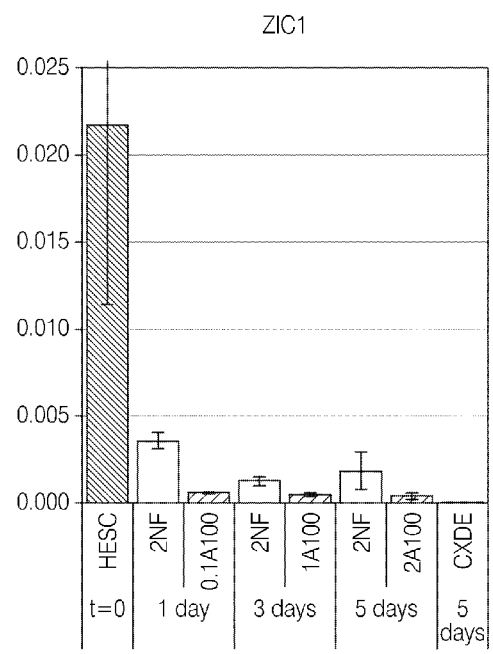
Figure 34F:
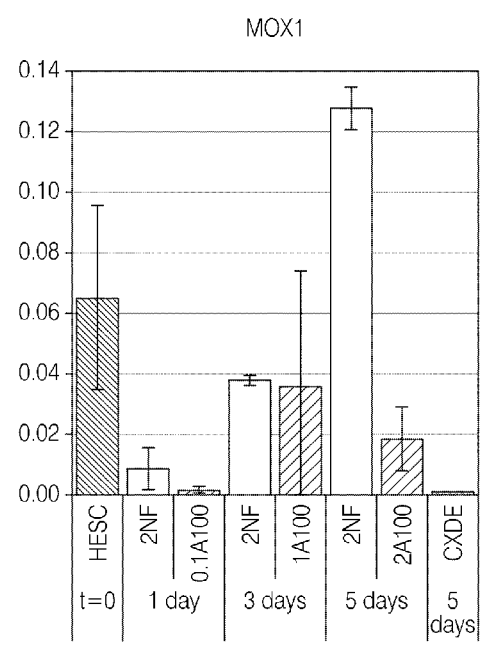
Figure 34G:
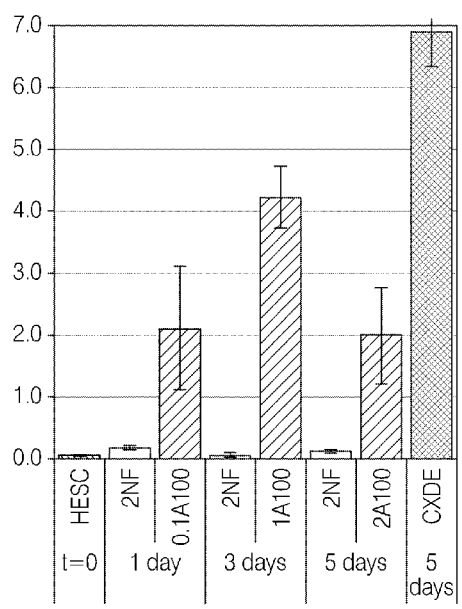
Figure 34H:
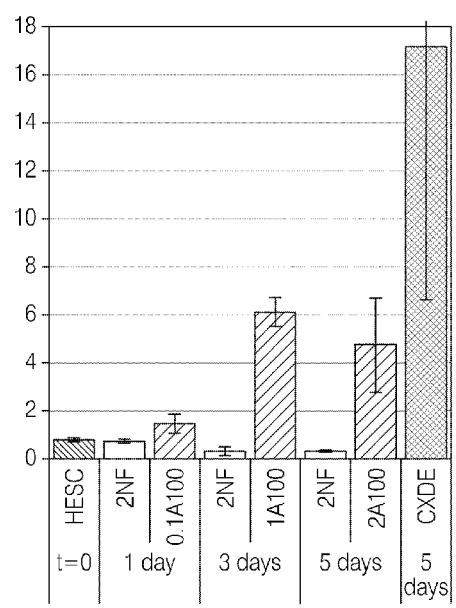
Figure 34I:
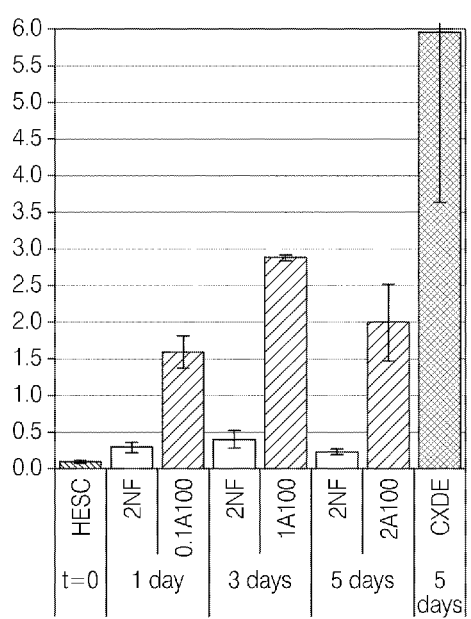
Figure 34J:
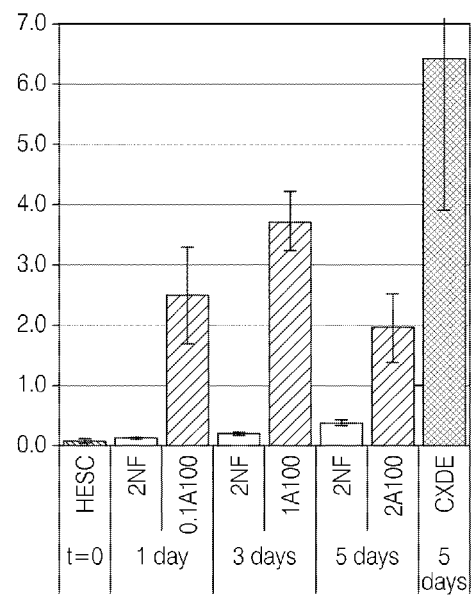
Figure 34K:
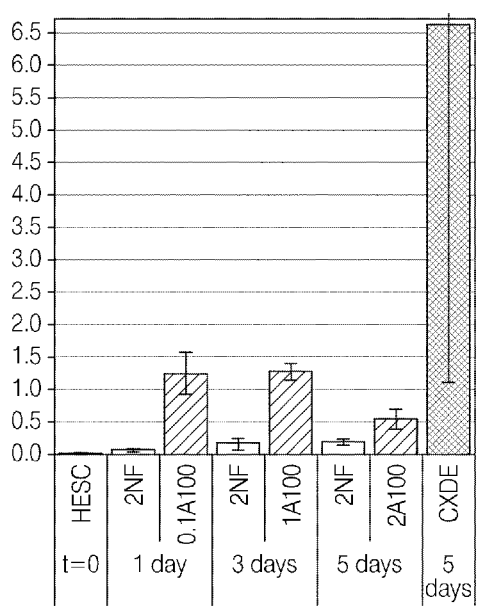
Figure 34L:
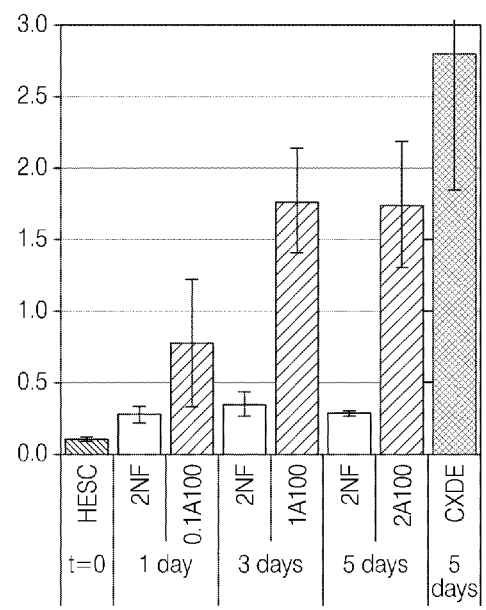
Figure 34M:
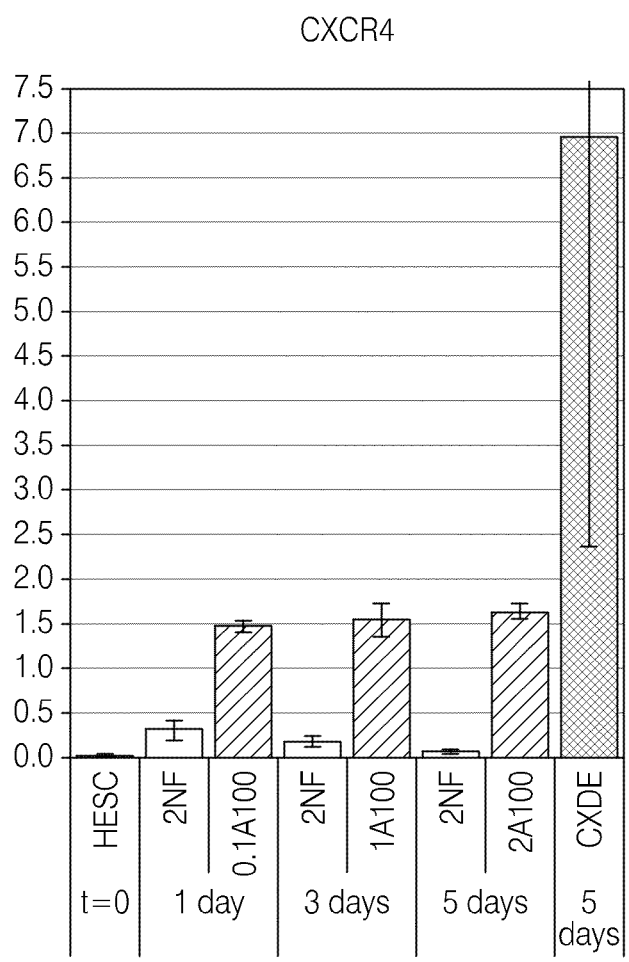

FIGS. 34A-M show the gene expression results for certain markers. Results are displayed for cell cultures analyzed 1, 3 and 5 days after the addition of 100 ng/ml activin A, CXCR4-expressing definitive endoderm cells purified at the end of the five day differentiation procedure (CXDE), and in purified human embryonic stem cells (hESC). A comparison of FIGS. 34C and G-M demonstrates that the six marker genes, FGF17, VWF, CALCR, FOXQ1, CMKOR1 and CRIP1, exhibit an expression pattern that is almost identical to each other and which is also identical to the pattern of expression of CXCR4 and SOX17/SOX7. As described previously, SOX17 is expressed in both the definitive endoderm as well as in the SOX7-expressing extra-embryonic endoderm. Since SOX7 is not expressed in the definitive endoderm, the ratio of SOX17/SOX7 provides a reliable estimate of definitive endoderm contribution to the SOX17 expression witnessed in the population as a whole. The similarity of panels G-L and M to panel C indicates that FGF17, VWF, CALCR, FOXQ1, CMKOR1 and CRIP1 are likely markers of definitive endoderm and that they are not significantly expressed in extra-embryonic endoderm cells.

It will be appreciated that the Q-PCR results described herein can be further confirmed by ICC.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

REFERENCES

Numerous literature and patent references have been cited in the present patent application. Each and every reference that cited in this patent application is incorporated by reference herein in its entirety.

For some references, the complete citation is in the body of the text. For other references the citation in the body of the text is by author and year, the complete citation being as follows:

Alexander, J., Rothenberg, M., Henry, G. L., and Stainier, D. Y. (1999). Casanova plays an early and essential role in endoderm formation in zebrafish. Dev Biol 215, 343-357.

Alexander, J., and Stainier, D. Y. (1999). A molecular pathway leading to endoderm formation in zebrafish. Curr Biol 9, 1147-1157.

Aoki, T. O., Mathieu, J., Saint-Etienne, L., Rebagliati, M. R., Peyrieras, N., and Rosa, F. M. (2002). Regulation of nodal signalling and mesendoderm formation by TARAM-A, a TGFbeta-related type I receptor. Dev Biol 241, 273-288.

Beck, S., Le Good, J. A., Guzman, M., Ben Haim, N., Roy, K., Beermann, F., and Constam, D. B. (2002). Extra-embryonic proteases regulate Nodal signalling during gastrulation. Nat Cell Biol 4, 981-985.

Beddington, R. S., Rashbass, P., and Wilson, V. (1992). Brachyury—a gene affecting mouse gastrulation and early organogenesis. Dev Suppl, 157-165.

Bongso, A., Fong, C. Y., Ng, S. C., and Ratnam, S. (1994). Isolation and culture of inner cell mass cells from human blastocysts. Hum Reprod 9, 2110-2117.

Chang, H., Brown, C. W., and Matzuk, M. M. (2002). Genetic analysis of the mammalian transforming growth factor-beta superfamily. Endocr Rev 23, 787-823.

Conlon, F. L., Lyons, K. M., Takaesu, N., Barth, K. S., Kispert, A., Herrmann, B., and Robertson, E. J. (1994). A primary requirement for nodal in the formation and maintenance of the primitive streak in the mouse. Development 120, 1919-1928.

Dougan, S. T., Warga, R. M., Kane, D. A., Schier, A. F., and Talbot, W. S. (2003). The role of the zebrafish nodal-related genes squint and cyclops in patterning of mesendoderm. Development 130, 1837-1851.

Feldman, B., Gates, M. A., Egan, E. S., Dougan, S. T., Rennebeck, G., Sirotkin, H. I., Schier, A. F., and Talbot, W. S. (1998). Zebrafish organizer development and germ-layer formation require nodal-related signals. Nature 395, 181-185.

Feng, Y., Broder, C. C., Kennedy, P. E., and Berger, E. A. (1996). HIV-1 entry cofactor: functional cDNA cloning of a seven-transmembrane, G protein-coupled receptor. Science 272, 872-877.

Futaki, S., Hayashi, Y., Yamashita, M., Yagi, K., Bono, H., Hayashizaki, Y., Okazaki, Y., and Sekiguchi, K. (2003). Molecular basis of constitutive production of basement membrane components: Gene expression profiles of engelbreth-holm-swarm tumor and F9 embryonal carcinoma cells. J Biol Chem.

Grapin-Botton, A., and Melton, D. A. (2000). Endoderm development: from patterning to organogenesis. Trends Genet 16, 124-130.

Harris, T. M., and Childs, G. (2002). Global gene expression patterns during differentiation of F9 embryonal carcinoma cells into parietal endoderm. Funct Integr Genomics 2, 105-119.

Hogan, B. L. (1996). Bone morphogenetic proteins in development. Curr Opin Genet Dev 6, 432-438.

Hogan, B. L. (1997). Pluripotent embryonic cells and methods of making same (U.S.A., Vanderbilt University).

Howe, C. C., Overton, G. C., Sawicki, J., Solter, D., Stein, P., and Strickland, S. (1988). Expression of SPARC/osteonectin transcript in murine embryos and gonads. Differentiation 37, 20-25.

Hudson, C., Clements, D., Friday, R. V., Stott, D., and Woodland, H. R. (1997). Xsox17alpha and -beta mediate endoderm formation in Xenopus. Cell 91, 397-405.

Imada, M., Imada, S., Iwasaki, H., Kume, A., Yamaguchi, H., and Moore, E. E. (1987). Fetomodulin: marker surface protein of fetal development which is modulatable by cyclic AMP. Dev Biol 122, 483-491.

Kanai-Azuma, M., Kanai, Y., Gad, J. M., Tajima, Y., Taya, C., Kurohmaru, M., Sanai, Y., Yonekawa, H., Yazaki, K., Tam, P. P., and Hayashi, Y. (2002). Depletion of definitive gut endoderm in Sox17-null mutant mice. Development 129, 2367-2379.

Katoh, M. (2002). Expression of human SOX7 in normal tissues and tumors. Int J Mol Med 9, 363-368.

Kikuchi, Y., Agathon, A., Alexander, J., Thisse, C., Waldron, S., Yelon, D., Thisse, B., and Stainier, D. Y. (2001). casanova encodes a novel Sox-related protein necessary and sufficient for early endoderm formation in zebrafish. Genes Dev 15, 1493-1505.

Kim, C. H., and Broxmeyer, H. E. (1999). Chemokines: signal lamps for trafficking of T and B cells for development and effector function. J Leukoc Biol 65, 6-15.

Kimelman, D., and Griffin, K. J. (2000). Vertebrate mesendoderm induction and patterning. Curr Opin Genet Dev 10, 350-356.

Kubo A, Shinozaki K, Shannon J M, Kouskoff V, Kennedy M, Woo S, Fehling H J, Keller G. (2004) Development of definitive endoderm from embryonic stem cells in culture. Development. 131, 1651-62.

Kumar, A., Novoselov, V., Celeste, A. J., Wolfman, N. M., ten Dijke, P., and Kuehn, M. R. (2001). Nodal signaling uses activin and transforming growth factor-beta receptor-regulated Smads. J Biol Chem 276, 656-661.

Labosky, P. A., Barlow, D. P., and Hogan, B. L. (1994a). Embryonic germ cell lines and their derivation from mouse primordial germ cells. Ciba Found Symp 182, 157-168; discussion 168-178.

Labosky, P. A., Barlow, D. P., and Hogan, B. L. (1994b). Mouse embryonic germ (EG) cell lines: transmission through the germline and differences in the methylation imprint of insulin-like growth factor 2 receptor (Igf2r) gene compared with embryonic stem (ES) cell lines. Development 120, 3197-3204.

Lickert, H., Kutsch, S., Kanzler, B., Tamai, Y., Taketo, M. M., and Kemler, R. (2002). Formation of multiple hearts in mice following deletion of beta-catenin in the embryonic endoderm. Dev Cell 3, 171-181.

Lu, C. C., Brennan, J., and Robertson, E. J. (2001). From fertilization to gastrulation: axis formation in the mouse embryo. Curr Opin Genet Dev 11, 384-392.

Ma, Q., Jones, D., and Springer, T. A. (1999). The chemokine receptor CXCR4 is required for the retention of B lineage and granulocytic precursors within the bone marrow microenvironment. Immunity 10, 463-471.

McGrath K E, Koniski A D, Maltby K M, McGann J K, Palis J. (1999) Embryonic expression and function of the chemokine SDF-1 and its receptor, CXCR4. Dev Biol. 213, 442-56.

Miyazono, K., Kusanagi, K., and Inoue, H. (2001). Divergence and convergence of TGF-beta/BMP signaling. J Cell Physiol 187, 265-276.

Nagasawa, T., Hirota, S., Tachibana, K., Takakura, N., Nishikawa, S., Kitamura, Y., Yoshida, N., Kikutani, H., and Kishimoto, T. (1996). Defects of B-cell lymphopoiesis and bone-marrow myelopoiesis in mice lacking the CXC chemokine PBSF/SDF-1. Nature 382, 635-638.

Niwa, H. (2001). Molecular mechanism to maintain stem cell renewal of ES cells. Cell Struct Funct 26, 137-148.

Ogura, H., Aruga, J., and Mikoshiba, K. (2001). Behavioral abnormalities of Zic1 and Zic2 mutant mice: implications as models for human neurological disorders. Behav Genet 31, 317-324.

Reubinoff, B. E., Pera, M. F., Fong, C. Y., Trounson, A., and Bongso, A. (2000). Embryonic stem cell lines from human blastocysts: somatic differentiation in vitro. Nat Biotechnol 18, 399-404.

Rodaway, A., and Patient, R. (2001). Mesendoderm. an ancient germ layer? Cell 105, 169-172.

Rodaway, A., Takeda, H., Koshida, S., Broadbent, J., Price, B., Smith, J. C., Patient, R., and Holder, N. (1999). Induction of the mesendoderm in the zebrafish germ ring by yolk cell-derived TGF-beta family signals and discrimination of mesoderm and endoderm by FGF. Development 126, 3067-3078.

Rohr, K. B., Schulte-Merker, S., and Tautz, D. (1999). Zebrafish zic1 expression in brain and somites is affected by BMP and hedgehog signalling. Mech Dev 85, 147-159.

Schier, A. F. (2003). Nodal signaling in vertebrate development. Annu Rev Cell Dev Biol 19, 589-621.

Schoenwolf, G. C., and Smith, J. L. (2000). Gastrulation and early mesodermal patterning in vertebrates. Methods Mol Biol 135, 113-125.

Shamblott, M. J., Axelman, J., Wang, S., Bugg, E. M., Littlefield, J. W., Donovan, P. J., Blumenthal, P. D., Huggins, G. R., and Gearhart, J. D. (1998). Derivation of pluripotent stem cells from cultured human primordial germ cells. Proc Natl Acad Sci USA 95, 13726-13731.

Shapiro, A. M., Lakey, J. R., Ryan, E. A., Korbutt, G. S., Toth, E., Warnock, G. L., Kneteman, N. M., and Rajotte, R. V. (2000). Islet transplantation in seven patients with type 1 diabetes mellitus using a glucocorticoid-free immunosuppressive regimen. N Engl J Med 343, 230-238.

Shapiro, A. M., Ryan, E. A., and Lakey, J. R. (2001a). Pancreatic islet transplantation in the treatment of diabetes mellitus. Best Pract Res Clin Endocrinol Metab 15, 241-264.

Shapiro, J., Ryan, E., Warnock, G. L., Kneteman, N. M., Lakey, J., Korbutt, G. S., and Rajotte, R. V. (2001b). Could fewer islet cells be transplanted in type 1 diabetes? Insulin independence should be dominant force in islet transplantation. Bmj 322, 861.

Shiozawa, M., Hiraoka, Y., Komatsu, N., Ogawa, M., Sakai, Y., and Aiso, S. (1996). Cloning and characterization of *Xenopus laevis* xSox7 cDNA. Biochim Biophys Acta 1309, 73-76.

Smith, J. (1997). Brachyury and the T-box genes. Curr Opin Genet Dev 7, 474-480.

Smith, J. C., Armes, N. A., Conlon, F. L., Tada, M., Umbhauer, M., and Weston, K. M. (1997). Upstream and downstream from Brachyury, a gene required for vertebrate mesoderm formation. Cold Spring Harb Symp Quant Biol 62, 337-346.

Takash, W., Canizares, J., Bonneaud, N., Poulat, F., Mattei, M. G., Jay, P., and Berta, P. (2001). SOX7 transcription factor: sequence, chromosomal localisation, expression, transactivation and interference with Wnt signalling. Nucleic Acids Res 29, 4274-4283.

Taniguchi, K., Hiraoka, Y., Ogawa, M., Sakai, Y., Kido, S., and Aiso, S. (1999). Isolation and characterization of a mouse SRY-related cDNA, mSox7. Biochim Biophys Acta 1445, 225-231.

Technau, U. (2001). Brachyury, the blastopore and the evolution of the mesoderm. Bioessays 23, 788-794.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Tremblay, K. D., Hoodless, P. A., Bikoff, E. K., and Robertson, E. J. (2000). Formation of the definitive endoderm in mouse is a Smad2-dependent process. Development 127, 3079-3090.

Vandesompele, J., De Preter, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol 3, RESEARCH0034.

Varlet, I., Collignon, J., and Robertson, E. J. (1997). nodal expression in the primitive endoderm is required for specification of the anterior axis during mouse gastrulation. Development 124, 1033-1044.

Vincent, S. D., Dunn, N. R., Hayashi, S., Norris, D. P., and Robertson, E. J. (2003). Cell fate decisions within the mouse organizer are governed by graded Nodal signals. Genes Dev 17, 1646-1662.

Weiler-Guettler, H., Aird, W. C., Rayburn, H., Husain, M., and Rosenberg, R. D. (1996). Developmentally regulated gene expression of thrombomodulin in postimplantation mouse embryos. Development 122, 2271-2281.

Weiler-Guettler, H., Yu, K., Soff, G., Gudas, L. J., and Rosenberg, R. D. (1992). Thrombomodulin gene regulation by cAMP and retinoic acid in F9 embryonal carcinoma cells. Proceedings Of The National Academy Of Sciences Of The United States Of America 89, 2155-2159.

Wells, J. M., and Melton, D. A. (1999). Vertebrate endoderm development. Annu Rev Cell Dev Biol 15, 393-410.

Wells, J. M., and Melton, D. A. (2000). Early mouse endoderm is patterned by soluble factors from adjacent germ layers. Development 127, 1563-1572.

Willison, K. (1990). The mouse Brachyury gene and mesoderm formation. Trends Genet 6, 104-105.

Zhao, G. Q. (2003). Consequences of knocking out BMP signaling in the mouse. Genesis 35, 43-56.

Zhou, X., Sasaki, H., Lowe, L., Hogan, B. L., and Kuehn, M. R. (1993). Nodal is a novel TGF-beta-like gene expressed in the mouse node during gastrulation. Nature 361, 543-547.

What is claimed is:

1. An in vitro cell culture comprising a medium human pluripotent cells and human definitive endoderm cells having been differentiated from said human pluripotent cells, wherein at least 1 human definitive endoderm cell is present for every 5 human pluripotent cells present in said cell culture, wherein said medium comprises a Wnt family member.

2. The cell culture of claim 1, wherein at least 1 human definitive endoderm cell is present for every 2 human pluripotent cells present in said cell culture.

3. The cell culture of claim 1, wherein at least 2 human definitive endoderm cells are present for every 1 human pluripotent cells present in said cell culture.

4. The cell culture of claim 1, wherein at least 5 human definitive endoderm cells are present for every 1 human pluripotent cells present in said cell culture.

5. The cell culture of claim 1, wherein at least 10 human definitive endoderm cells are present for every 1 human pluripotent cells present in said cell culture.

6. The cell culture of claim 1, wherein said human pluripotent cell comprises an embryonic stem cell.

7. The cell culture of claim 1, wherein said medium lacks B27.

8. The cell culture of claim 1, wherein said medium lacks serum replacement.

9. The cell culture of claim 1, wherein said medium comprises a growth factor of the Nodal/Activin subgroup of the TGFβ superfamily.

10. The cell culture of claim 9, further comprising a growth factor selected from the group consisting of Nodal, Activin A, Activin B and combinations thereof.

11. The cell culture of claim 1, wherein said medium comprises Nodal.

12. The cell culture of claim 1, wherein said medium comprises Activin B.

13. The cell culture of claim 1, which is substantially free of cells derived from the ectoderm lineage.

14. The cell culture of claim 1, wherein said human cells are nonrecombinant cells.

15. The cell culture of claim 1, wherein said human definitive endoderm cells adhere to a surface of a culture vessel.

16. The cell culture of claim 1, wherein said medium comprises Activin A.

17. The cell culture of claim 1, wherein said Wnt family member comprises Wnt3A.

* * * * *

UNITED STATES PATENT AND TRADEMARK OFFICE
CERTIFICATE OF CORRECTION

PATENT NO. : 8,623,645 B2
APPLICATION NO. : 12/414482
DATED : January 7, 2014
INVENTOR(S) : Kevin Allen D'Amour, Alan D. Agulnick and Emmanuel E. Baetge It is certified that error appears in the above-identified patent and that said Letters Patent is hereby corrected as shown below:

In the Specification:

Please correct the number "4" to "34" in column 5, line 28.

In the Claims:

Please correct Claim 1 to insert a --,-- between "medium" and "human" in column 45, line 23.

Signed and Sealed this
Ninth Day of September, 2014

Michelle K. Lee
*Deputy Director of the United States Patent and Trademark Office*

SEQUENCE LISTING

```
<160> NUMBER OF SEQ ID NOS: 2

<210> SEQ ID NO 1
<211> LENGTH: 1245
<212> TYPE: DNA
<213> ORGANISM: Homo sapiens

<400> SEQUENCE: 1
atgagcagcc cggatgcggg atacgccagt gacgaccaga gccagaccca gagcgcgctg      60
cccgcggtga tggccgggct gggcccctgc ccctgggccg agtcgctgag ccccatcggg     120
gacatgaagg tgaagggcga ggcgccggcg aacagcggag caccggccgg ggccgcgggc     180
cgagccaagg gcgagtcccg tatccggcgg ccgatgaacg ctttcatggt gtgggctaag     240
gacgagcgca agcggctggc gcagcagaat ccagacctgc acaacgccga gttgagcaag     300
atgctgggca agtcgtggaa ggcgctgacg ctggcggaga agcggcccct cgtggaggag     360
gcagagcggc tgcgcgtgca gcacatgcag gaccacccca actacaagta ccggccgcgg     420
cggcgcaagc aggtgaagcg gctgaagcgg gtggagggcg gcttcctgca cggcctggct     480
gagccgcagg cggccgcgct gggccccgag ggcggccgcg tggccatgga cggcctgggc     540
ctccagttcc ccgagcaggg cttccccgcc ggcccgcgc  tgctgcctcc gcacatgggc     600
ggccactacc gcgactgcca gagtctgggc gcgcctccgc tcgacggcta cccgttgccc     660
acgcccgaca cgtccccgct ggacgcgtg  gacccgacc  cggcttcctt cgccgcccg      720 atgcccgggg actgcccggc ggccggcacc tacagctacg cgcaggtctc ggactacgct     780
```

```
ggcccccgg agcctcccgc cggtcccatg cacccccgac tcggcccaga gcccgcgggt    840
ccctcgattc cgggcctcct ggcgccaccc agcgcccttc acgtgtacta cggcgcgatg    900
ggctcgcccg ggcgggcgg cgggcgcggc ttccagatgc agccgcaaca ccagcaccag    960
caccagcacc agcaccaccc ccgggcccc ggacagccgt cgcccctcc ggaggcactg   1020 ccctgccggg acggcacgga ccccagtcag cccgccgagc tcctcgggga ggtggaccgc   1080
acggaatttg aacagtatct gcacttcgtg tgcaagcctg agatgggcct ccctaccag   1140 gggcatgact ccggtgtgaa tctccccgac agccacgggg ccatttcctc ggtggtgtcc   1200
gacgccagct ccgcggtata ttactgcaac tatcctgacg tgtga                  1245
```

<210> SEQ ID NO 2
<211> LENGTH: 414
<212> TYPE: PRT
<213> ORGANISM: Homo sapiens

<400> SEQUENCE: 2

```
Met Ser Ser Pro Asp Ala Gly Tyr Ala Ser Asp Gln Ser Gln Thr
 1               5                  10                  15

Gln Ser Ala Leu Pro Ala Val Met Ala Gly Leu Gly Pro Cys Pro Trp
            20                  25                  30

Ala Glu Ser Leu Ser Pro Ile Gly Asp Met Lys Val Lys Gly Glu Ala
        35                  40                  45

Pro Ala Asn Ser Gly Ala Pro Ala Gly Ala Ala Gly Arg Ala Lys Gly
    50                  55                  60

Glu Ser Arg Ile Arg Arg Pro Met Asn Ala Phe Met Val Trp Ala Lys
65                  70                  75                  80

Asp Glu Arg Lys Arg Leu Ala Gln Gln Asn Pro Asp Leu His Asn Ala
                85                  90                  95

Glu Leu Ser Lys Met Leu Gly Lys Ser Trp Lys Ala Leu Thr Leu Ala
            100                 105                 110

Glu Lys Arg Pro Phe Val Glu Glu Ala Glu Arg Leu Arg Val Gln His
        115                 120                 125

Met Gln Asp His Pro Asn Tyr Lys Tyr Arg Pro Arg Arg Arg Lys Gln
    130                 135                 140

Val Lys Arg Leu Lys Arg Val Glu Gly Gly Phe Leu His Gly Leu Ala
145                 150                 155                 160

Glu Pro Gln Ala Ala Ala Leu Gly Pro Glu Gly Gly Arg Val Ala Met
                165                 170                 175

Asp Gly Leu Gly Leu Gln Phe Pro Glu Gln Gly Phe Pro Ala Gly Pro
            180                 185                 190

Pro Leu Leu Pro Pro His Met Gly Gly His Tyr Arg Asp Cys Gln Ser
        195                 200                 205

Leu Gly Ala Pro Pro Leu Asp Gly Tyr Pro Leu Pro Thr Pro Asp Thr
    210                 215                 220

Ser Pro Leu Asp Gly Val Asp Pro Asp Pro Ala Phe Phe Ala Ala Pro
225                 230                 235                 240

Met Pro Gly Asp Cys Pro Ala Ala Gly Thr Tyr Ser Tyr Ala Gln Val
                245                 250                 255

Ser Asp Tyr Ala Gly Pro Pro Glu Pro Pro Ala Gly Pro Met His Pro
            260                 265                 270

Arg Leu Gly Pro Glu Pro Ala Gly Pro Ser Ile Pro Gly Leu Leu Ala
        275                 280                 285

Pro Pro Ser Ala Leu His Val Tyr Tyr Gly Ala Met Gly Ser Pro Gly
    290                 295                 300
```

```
Ala Gly Gly Gly Arg Gly Phe Gln Met Gln Pro Gln His Gln His Gln
305                 310                 315                 320
His Gln His Gln His His Pro Pro Gly Pro Gly Gln Pro Ser Pro Pro
                325                 330                 335
Pro Glu Ala Leu Pro Cys Arg Asp Gly Thr Asp Pro Ser Gln Pro Ala
            340                 345                 350
Glu Leu Leu Gly Glu Val Asp Arg Thr Glu Phe Glu Gln Tyr Leu His
        355                 360                 365
Phe Val Cys Lys Pro Glu Met Gly Leu Pro Tyr Gln Gly His Asp Ser
    370                 375                 380
Gly Val Asn Leu Pro Asp Ser His Gly Ala Ile Ser Ser Val Val Ser
385                 390                 395                 400
Asp Ala Ser Ser Ala Val Tyr Tyr Cys Asn Tyr Pro Asp Val
                405                 410
```